(12) United States Patent
Deng et al.

(10) Patent No.: US 11,186,573 B2
(45) Date of Patent: Nov. 30, 2021

(54) INHIBITORS OF ROR GAMMA

(71) Applicant: Vitae Pharmaceuticals, LLC, Madison, NJ (US)

(72) Inventors: Chaoyi Deng, Shanghai (CN); Jun He, Shanghai (CN); Bo Xu, Shanghai (CN)

(73) Assignee: Vitae Pharmaceuticals, LLC, Madison, NJ (US)

( * ) Notice: Subject to any disclaimer, the term of this patent is extended or adjusted under 35 U.S.C. 154(b) by 0 days.

(21) Appl. No.: 16/633,334

(22) PCT Filed: Jul. 24, 2018

(86) PCT No.: PCT/US2018/043463
§ 371 (c)(1),
(2) Date: Jan. 23, 2020

(87) PCT Pub. No.: WO2019/023216
PCT Pub. Date: Jan. 31, 2019

(65) Prior Publication Data
US 2020/0165245 A1 May 28, 2020

(30) Foreign Application Priority Data
Jul. 24, 2017 (WO) ............... PCT/CN2017/094043

(51) Int. Cl.
*C07D 471/04* (2006.01)
(52) U.S. Cl.
CPC ........ *C07D 471/04* (2013.01); *C07B 2200/13* (2013.01)
(58) Field of Classification Search
CPC ...................... C07D 471/04; C07D 2200/13
USPC ......................................... 546/113; 514/300
See application file for complete search history.

(56) References Cited

U.S. PATENT DOCUMENTS

| | | | |
|---|---|---|---|
| 5,238,950 A | 8/1993 | Clader et al. | |
| 5,272,158 A | 12/1993 | Hartman et al. | |
| 5,326,760 A | 7/1994 | McElroy et al. | |
| 5,364,869 A | 11/1994 | De | |
| 5,389,631 A | 2/1995 | Claremon et al. | |
| 5,571,774 A | 11/1996 | Hamprecht et al. | |
| 5,719,144 A | 2/1998 | Hartman et al. | |
| 5,770,590 A | 6/1998 | Natsugari et al. | |
| 5,786,352 A | 7/1998 | Natsugari et al. | |
| 5,959,116 A | 9/1999 | Hamprecht et al. | |
| 6,103,659 A | 8/2000 | Pasenok et al. | |
| 6,166,219 A | 12/2000 | Yamasaki et al. | |
| 6,177,443 B1 | 1/2001 | Madsen et al. | |
| 6,348,032 B1 | 2/2002 | Sperl et al. | |
| 6,358,978 B1 | 3/2002 | Ritzeler et al. | |
| 6,417,207 B1 | 7/2002 | Garvey et al. | |
| 6,444,617 B1 | 9/2002 | Takaishi et al. | |
| 6,489,315 B1 | 12/2002 | Natsugari et al. | |
| 6,512,117 B1 | 1/2003 | Harclerode et al. | |
| 6,627,646 B2 * | 9/2003 | Bakale | A61P 37/08 514/322 |
| 6,770,666 B2 | 8/2004 | Hashimoto et al. | |
| 7,112,600 B1 | 9/2006 | Hashimoto et al. | |
| 7,115,752 B2 | 10/2006 | Lesieur et al. | |
| 7,183,318 B2 | 2/2007 | Lesieur et al. | |
| 7,244,730 B2 | 7/2007 | Suzuki et al. | |
| 7,732,616 B2 | 6/2010 | Marlow et al. | |
| 7,750,021 B2 | 7/2010 | Mi et al. | |
| 8,389,739 B1 | 3/2013 | Thacher et al. | |
| 8,399,477 B2 | 3/2013 | Alisi et al. | |
| 8,415,351 B2 | 4/2013 | Wagner et al. | |
| 9,266,886 B2 | 2/2016 | Lotesta et al. | |
| 9,481,674 B1 | 11/2016 | Claremon et al. | |
| 9,624,217 B2 | 4/2017 | Claremon et al. | |
| 9,663,515 B2 | 5/2017 | Claremon et al. | |
| 9,796,710 B2 | 10/2017 | Claremon et al. | |
| 9,868,748 B2 | 1/2018 | Claremon et al. | |
| 10,047,085 B2 | 8/2018 | Claremon et al. | |
| 10,087,184 B2 | 10/2018 | Claremon et al. | |
| 10,301,261 B2 | 5/2019 | Claremon et al. | |
| 10,399,976 B2 | 9/2019 | Claremon et al. | |
| 2002/0132817 A1 | 9/2002 | Natsugari et al. | |
| 2003/0050320 A1 | 3/2003 | Hashimoto et al. | |
| 2004/0002424 A1 | 1/2004 | Minn et al. | |
| 2004/0038973 A1 | 2/2004 | Nahra et al. | |
| 2005/0004204 A1 | 1/2005 | Suzuki et al. | |
| 2005/0020593 A1 | 1/2005 | Mailliet et al. | |
| 2005/0234065 A1 | 10/2005 | Hulin et al. | |
| 2006/0135557 A1 | 6/2006 | Nan et al. | |
| 2007/0032497 A1 | 2/2007 | Hashimoto et al. | |
| 2007/0112038 A1 | 5/2007 | Marlow et al. | |
| 2007/0258887 A1 | 11/2007 | Tamagnan et al. | |

(Continued)

FOREIGN PATENT DOCUMENTS

| | | | |
|---|---|---|---|
| CA | 2031684 A1 | 6/1991 | |
| CA | 2134192 A1 | 5/1995 | |

(Continued)

OTHER PUBLICATIONS

Bernstein, "Polymorphism in . . ." p. 115-118, 272. (Year: 2002).*
Davidovich et al., "Detection of polymorphism . . ." Am. Pharm. Rev. 7(1) p. 10, 12, 14, 16, 100 . . . (Year: 2004).*
Dean "Analytical Chem . . ." p. 10.24-10.26. (Year: 1995).*
Ivanisevic et al. "Use of X-ray . . ." Pharm. Sci. Encycl. p. 1-42 . . . (Year: 2010).*
Seddon "Pseudopolymorph . . ." Crystal Growth &amp; design v.4(6) p. 1087 (2 pages from internet). (Year: 2004).*
Rodriguez-Spong et al., "General principles, etc.," Adv. Drug Delivery Reviews 56 241-274. (Year: 2004).*

(Continued)

*Primary Examiner* — Patricia L Morris
(74) *Attorney, Agent, or Firm* — McCarter & English, LLP; Steven G. Davis; Michael J. DeGrazia

(57) ABSTRACT

The present disclosure relates to salts and crystalline forms of a compound having the formula (I): Also described are processes for the production of the salts and crystalline forms described herein.

6 Claims, 25 Drawing Sheets

(56) References Cited

U.S. PATENT DOCUMENTS

| | | |
|---|---|---|
| 2008/0277622 A1 | 11/2008 | Deshpande et al. |
| 2008/0287462 A1 | 11/2008 | Chessari et al. |
| 2009/0036423 A1 | 2/2009 | Pan et al. |
| 2009/0076275 A1 | 3/2009 | Bolin et al. |
| 2009/0233945 A9 | 9/2009 | Chessari et al. |
| 2009/0258871 A1 | 10/2009 | Jitsuoka et al. |
| 2009/0270405 A1 | 10/2009 | Cook, II et al. |
| 2010/0099684 A1 | 4/2010 | Cook, II et al. |
| 2011/0070193 A1 | 3/2011 | Wagner et al. |
| 2011/0189167 A1 | 8/2011 | Flynn et al. |
| 2011/0313003 A1 | 12/2011 | Shi et al. |
| 2012/0077840 A1 | 3/2012 | Turner et al. |
| 2012/0115903 A1 | 5/2012 | Frank et al. |
| 2012/0245163 A1 | 9/2012 | Gomtsyan et al. |
| 2012/0322837 A1 | 12/2012 | Maeba et al. |
| 2013/0143870 A1 | 6/2013 | Grauert et al. |
| 2013/0150347 A1 | 6/2013 | Rudolf et al. |
| 2014/0163001 A1 | 6/2014 | Yamamoto et al. |
| 2014/0228409 A1 | 8/2014 | Yamamoto et al. |
| 2019/0322687 A1 | 10/2019 | Claremon et al. |
| 2019/0352286 A1 | 11/2019 | Claremon et al. |
| 2020/0062707 A1 | 2/2020 | Claremon et al. |
| 2020/0079767 A1 | 3/2020 | Claremon et al. |
| 2020/0148677 A1 | 5/2020 | Duguid et al. |
| 2020/0165245 A1 | 5/2020 | Deng et al. |
| 2020/0172535 A1 | 6/2020 | Claremon et al. |
| 2020/0339566 A1 | 10/2020 | Claremon et al. |

FOREIGN PATENT DOCUMENTS

| | | |
|---|---|---|
| CA | 2352612 A1 | 6/2000 |
| CA | 2524027 A1 | 12/2004 |
| CN | 1424770 A | 6/2003 |
| CN | 1869036 A | 11/2006 |
| CN | 101225070 A | 7/2008 |
| CN | 101455661 A | 6/2009 |
| CN | 102180780 A | 9/2011 |
| CN | 104024239 A | 9/2014 |
| DE | 4343922 A1 | 6/1995 |
| DE | 4446396 A1 | 7/1995 |
| EP | 254951 A2 | 2/1988 |
| EP | 321368 A1 | 6/1989 |
| EP | 468187 A2 | 1/1992 |
| EP | 520277 A2 | 12/1992 |
| EP | 520573 A1 | 12/1992 |
| EP | 540334 A1 | 5/1993 |
| EP | 655439 A2 | 5/1995 |
| EP | 733632 A1 | 9/1996 |
| EP | 1178048 A1 | 2/2002 |
| EP | 2327704 A1 | 6/2011 |
| FR | 2725946 A1 | 4/1996 |
| FR | 2926554 A1 | 7/2009 |
| GB | 2276384 A | 9/1994 |
| JP | H06-236056 A | 8/1994 |
| JP | H11-43489 A | 2/1999 |
| JP | 2000-007661 A | 1/2000 |
| JP | 2003-171380 A | 6/2003 |
| JP | 2003-531894 A | 10/2003 |
| JP | 2004-203791 A | 7/2004 |
| JP | 2004-535404 A | 11/2004 |
| JP | 2015-124178 A | 7/2015 |
| WO | WO-1990/09787 A1 | 9/1990 |
| WO | WO-1994/00119 A1 | 1/1994 |
| WO | WO-1994/24712 A1 | 10/1994 |
| WO | WO-1995/11680 A1 | 5/1995 |
| WO | WO-1995/17397 A1 | 6/1995 |
| WO | WO-1996/26187 A1 | 8/1996 |
| WO | WO-1997/32832 A1 | 9/1997 |
| WO | WO-1998/40385 A1 | 9/1998 |
| WO | WO-1998/42666 A1 | 10/1998 |
| WO | WO-1999/47132 A2 | 9/1999 |
| WO | WO-1999/58495 A1 | 11/1999 |
| WO | WO-1999/58496 A1 | 11/1999 |
| WO | WO-2000/032192 A1 | 6/2000 |
| WO | WO-2000/067754 A1 | 11/2000 |
| WO | WO-2001/005790 A1 | 1/2001 |
| WO | WO-2001/09076 A2 | 2/2001 |
| WO | WO-2001/047883 A1 | 7/2001 |
| WO | WO-2001/051128 A1 | 7/2001 |
| WO | WO-2001/83438 A2 | 11/2001 |
| WO | WO-2001/083445 A1 | 11/2001 |
| WO | WO-2001/85722 A1 | 11/2001 |
| WO | WO-2002/024650 A2 | 3/2002 |
| WO | WO-2002/38107 A2 | 5/2002 |
| WO | WO-2002/081443 A1 | 10/2002 |
| WO | WO-2002/081447 A1 | 10/2002 |
| WO | WO-2002/081463 A1 | 10/2002 |
| WO | WO-2002/085855 A1 | 10/2002 |
| WO | WO-2002/094833 A1 | 11/2002 |
| WO | WO-2003/008421 A1 | 1/2003 |
| WO | WO-2003/029252 A1 | 4/2003 |
| WO | WO-2003/029254 A1 | 4/2003 |
| WO | WO-2003/043991 A1 | 5/2003 |
| WO | WO-2003/062241 A1 | 7/2003 |
| WO | WO-2003/066055 A1 | 8/2003 |
| WO | WO-2003/070710 A1 | 8/2003 |
| WO | WO-2003/076440 A1 | 9/2003 |
| WO | WO-2003/104216 A1 | 12/2003 |
| WO | WO-2004/014365 A1 | 2/2004 |
| WO | WO-2004/026871 A1 | 4/2004 |
| WO | WO-2004/042029 A2 | 5/2004 |
| WO | WO-2004/065351 A1 | 8/2004 |
| WO | WO-2004/089897 A1 | 10/2004 |
| WO | WO-2004/103309 A2 | 12/2004 |
| WO | WO-2004/108133 A2 | 12/2004 |
| WO | WO-2004/111010 A1 | 12/2004 |
| WO | WO-2004/113330 A1 | 12/2004 |
| WO | WO-2005/005392 A1 | 1/2005 |
| WO | WO-2005/011601 A2 | 2/2005 |
| WO | WO-2005/023806 A2 | 3/2005 |
| WO | WO-2005/025504 A2 | 3/2005 |
| WO | WO-2005/028480 A2 | 3/2005 |
| WO | WO-2005/039564 A1 | 5/2005 |
| WO | WO-2005/051301 A2 | 6/2005 |
| WO | WO-2005/060958 A1 | 7/2005 |
| WO | WO-2005/063296 A2 | 7/2005 |
| WO | WO-2005/097129 A2 | 10/2005 |
| WO | WO-2005/100334 A1 | 10/2005 |
| WO | WO-2005/117890 A2 | 12/2005 |
| WO | WO-2006/032631 A1 | 3/2006 |
| WO | WO-2006/062981 A2 | 6/2006 |
| WO | WO-2006/065842 A2 | 6/2006 |
| WO | WO-2006/074428 A2 | 7/2006 |
| WO | WO-2006/082001 A1 | 8/2006 |
| WO | WO-2006/092731 A1 | 9/2006 |
| WO | WO-2006/109085 A1 | 10/2006 |
| WO | WO-2007/007054 A1 | 1/2007 |
| WO | WO-2007/022280 A1 | 2/2007 |
| WO | WO-2007/036733 A1 | 4/2007 |
| WO | WO-2007/036734 A1 | 4/2007 |
| WO | WO-2007/050124 A1 | 5/2007 |
| WO | WO-2007/084451 A1 | 7/2007 |
| WO | WO-2007/084455 A1 | 7/2007 |
| WO | WO-2007/084815 A2 | 7/2007 |
| WO | WO-2007/087231 A2 | 8/2007 |
| WO | WO-2007/097931 A2 | 8/2007 |
| WO | WO-2007/101224 A2 | 9/2007 |
| WO | WO-2007/107545 A1 | 9/2007 |
| WO | WO-2007/109596 A2 | 9/2007 |
| WO | WO-2007/131982 A2 | 11/2007 |
| WO | WO-2008/006479 A1 | 1/2008 |
| WO | WO-2008/010964 A1 | 1/2008 |
| WO | WO-2008/013963 A2 | 1/2008 |
| WO | WO-2008/044027 A2 | 4/2008 |
| WO | WO-2008/044029 A1 | 4/2008 |
| WO | WO-2008/044041 A1 | 4/2008 |
| WO | WO-2008/044045 A1 | 4/2008 |
| WO | WO-2008/044054 A2 | 4/2008 |
| WO | WO-2008/048991 A2 | 4/2008 |
| WO | WO-2008/073865 A2 | 6/2008 |
| WO | WO-2008/083070 A1 | 7/2008 |
| WO | WO-2008/086161 A1 | 7/2008 |
| WO | WO-2008/132155 A2 | 11/2008 |
| WO | WO-2008/135524 A2 | 11/2008 |

(56) References Cited

FOREIGN PATENT DOCUMENTS

| | | |
|---|---|---|
| WO | WO-2008/135526 A1 | 11/2008 |
| WO | WO-2008/149163 A2 | 12/2008 |
| WO | WO-2009/004496 A2 | 1/2009 |
| WO | WO-2009/013299 A2 | 1/2009 |
| WO | WO-2009/026248 A2 | 2/2009 |
| WO | WO-2009/049154 A1 | 4/2009 |
| WO | WO-2009/050228 A2 | 4/2009 |
| WO | WO-2009/052319 A1 | 4/2009 |
| WO | WO-2009/052320 A1 | 4/2009 |
| WO | WO-2009/068463 A2 | 6/2009 |
| WO | WO-2009/073788 A1 | 6/2009 |
| WO | WO-2009/083526 A1 | 7/2009 |
| WO | WO-2009/097972 A1 | 8/2009 |
| WO | WO-2009/112445 A1 | 9/2009 |
| WO | WO-2009/112678 A2 | 9/2009 |
| WO | WO-2009/112826 A1 | 9/2009 |
| WO | WO-2009/112839 A1 | 9/2009 |
| WO | WO-2009/124755 A1 | 10/2009 |
| WO | WO-2009/131926 A1 | 10/2009 |
| WO | WO-2009/144450 A1 | 12/2009 |
| WO | WO-2010/003022 A1 | 1/2010 |
| WO | WO-2010/021878 A1 | 2/2010 |
| WO | WO-2010/033350 A1 | 3/2010 |
| WO | WO-2010/056194 A1 | 5/2010 |
| WO | WO-2010/056195 A1 | 5/2010 |
| WO | WO-2010/077680 A2 | 7/2010 |
| WO | WO-2010/086311 A1 | 8/2010 |
| WO | WO-2011/078143 A1 | 6/2011 |
| WO | WO-2011/090473 A1 | 7/2011 |
| WO | WO-2011/094545 A2 | 8/2011 |
| WO | WO-2011/107248 A1 | 9/2011 |
| WO | WO-2011/140936 A1 | 11/2011 |
| WO | WO-2011/146358 A1 | 11/2011 |
| WO | WO-2011/159297 A1 | 12/2011 |
| WO | WO-2012/019015 A2 | 2/2012 |
| WO | WO-2012/027965 A1 | 3/2012 |
| WO | WO-2012/028100 A1 | 3/2012 |
| WO | WO-2012/031197 A1 | 3/2012 |
| WO | WO-2012/043505 A1 | 4/2012 |
| WO | WO-2012/062462 A1 | 5/2012 |
| WO | WO-2012/064744 A2 | 5/2012 |
| WO | WO-2012/100732 A1 | 8/2012 |
| WO | WO-2012/100734 A1 | 8/2012 |
| WO | WO-2012/106995 A1 | 8/2012 |
| WO | WO-2012/125521 A1 | 9/2012 |
| WO | WO-2012/136296 A1 | 10/2012 |
| WO | WO-2012/139775 A1 | 10/2012 |
| WO | WO-2013/000994 A1 | 1/2013 |
| WO | WO-2013/019621 A1 | 2/2013 |
| WO | WO-2013/019626 A1 | 2/2013 |
| WO | WO-2013/019635 A1 | 2/2013 |
| WO | WO-2013/019653 A1 | 2/2013 |
| WO | WO-2013/019682 A1 | 2/2013 |
| WO | WO-2013/029338 A1 | 3/2013 |
| WO | WO-2013/045431 A1 | 4/2013 |
| WO | WO-2013/064231 A1 | 5/2013 |
| WO | WO-2013/067036 A1 | 5/2013 |
| WO | WO-2013/078233 A1 | 5/2013 |
| WO | WO-2013/078240 A1 | 5/2013 |
| WO | WO-2013/079223 A1 | 6/2013 |
| WO | WO-2013/083741 A1 | 6/2013 |
| WO | WO-2013/087739 A1 | 6/2013 |
| WO | WO-2013/092460 A1 | 6/2013 |
| WO | WO-2013/092939 A1 | 6/2013 |
| WO | WO-2013/092941 A1 | 6/2013 |
| WO | WO-2013/096496 A2 | 6/2013 |
| WO | WO-2013/100027 A1 | 7/2013 |
| WO | WO-2013/159235 A1 | 10/2013 |
| WO | WO-2013/160418 A1 | 10/2013 |
| WO | WO-2013/160419 A1 | 10/2013 |
| WO | WO-2013/166013 A1 | 11/2013 |
| WO | WO-2013/169588 A1 | 11/2013 |
| WO | WO-2013/169704 A2 | 11/2013 |
| WO | WO-2013/169864 A2 | 11/2013 |
| WO | WO-2013/171729 A2 | 11/2013 |
| WO | WO-2013/178362 A1 | 12/2013 |
| WO | WO-2014/008214 A1 | 1/2014 |
| WO | WO-2014/009447 A1 | 1/2014 |
| WO | WO-2014/026327 A1 | 2/2014 |
| WO | WO-2014/026328 A1 | 2/2014 |
| WO | WO-2014/026329 A1 | 2/2014 |
| WO | WO-2014/026330 A1 | 2/2014 |
| WO | WO-2014/028589 A2 | 2/2014 |
| WO | WO-2014/028591 A2 | 2/2014 |
| WO | WO-2014/028597 A2 | 2/2014 |
| WO | WO-2014/028600 A2 | 2/2014 |
| WO | WO-2014/028669 A1 | 2/2014 |
| WO | WO-2014/044738 A1 | 3/2014 |
| WO | WO-2014/062938 A1 | 4/2014 |
| WO | WO-2014/086894 A1 | 6/2014 |
| WO | 2014/110442 A1 | 7/2014 |
| WO | WO-2014/179564 A1 | 11/2014 |
| WO | 2015/017335 A1 | 2/2015 |
| WO | 2015/035032 A1 | 3/2015 |
| WO | WO-2015/038503 A1 | 3/2015 |
| WO | 2015/067575 A1 | 5/2015 |
| WO | WO-2015/083130 A1 | 6/2015 |
| WO | WO-2015/100420 A1 | 7/2015 |
| WO | WO-2015/101928 A1 | 7/2015 |
| WO | WO-2015/114157 A1 | 8/2015 |
| WO | WO-2015/116904 A1 | 8/2015 |
| WO | WO-2015/144480 A1 | 10/2015 |
| WO | WO-2015/144605 A1 | 10/2015 |
| WO | WO-2015/144609 A1 | 10/2015 |
| WO | WO-2015/144803 A1 | 10/2015 |
| WO | WO-2015/159233 A1 | 10/2015 |
| WO | WO-2016/061160 A1 | 4/2016 |
| WO | WO-2016/064970 A1 | 4/2016 |
| WO | WO-2016/144351 A1 | 9/2016 |
| WO | WO-2017/024018 A1 | 2/2017 |
| WO | WO-2017/087608 A1 | 5/2017 |
| WO | WO-2017/132432 A1 | 8/2017 |

OTHER PUBLICATIONS

Kirk-Othmer Encyclopedia of Chemical Technology, 8, pp. 95-147. (Year: 2002).*
Vippagunta et al., "Crystalline Solids", Advanced Drug Delivery Reviews 48 .3-26. (Year: 2001).*
Guillory (in Brittain ed.), "Polymorphism in Pharmaceutical Solids.," NY: Marcel Dekker, Inc., 1-2, 183-226. (Year: 1999).*
Braga et al., "Making crystals from . . . " J. Royal Soc. Chem. Commun. p. 3635-3645. (Year: 2005).*
CMU Pharmaceutical polymorphism, internet p. 1-3 printout Apr. 3, 2008. (Year: 2002).*
Singhal et al., "Drug Polymorphism, etc.," Advanced Drug Delivery reviews 56, p. 335-347. (Year: 2004).*
Concise Encyclopedia Chemistry, NY: Walter de Gruyter, 872-873. (Year: 1993).*
Jain et al., "Polymorphism in Pharmacy", Indian Drugs, 23(6) 315-329. (Year: 1986).*
Muzaffar et al., "Polymorphism and Drug Availability, etc.," J of Pharm. (Lahore), 1(1), 59-66. (Year: 1979).*
U.S. Pharmacopia #23, National Formulary #18,1843-1844. (Year: 1995).*
Doelker, english translation of S.T.P, Pratiques, 9(5), 399-409, pp. 1-33. (Year: 1999).*
Doelker, english translation of Ann. Pharm. Fr.,60: 161-176, pp. 1-39. (Year: 2002).*
Taday et al., "Using Terahertz, etc.," J of Pharm. Sci., 92(4), 831-838. (Year: 2003).*
Otuska et al., "Effect of Polymorphic, etc.," Chem. Pharm. Bull., 47(6) 852-8569. (Year: 1999).*
Babu et al., Emerging therapeutic strategies in COPD. Drug Discov Today. Mar. 2015;20(3):371-9.
Bendele et al., Animal models of arthritis: relevance to human disease. Toxicol Pathol. Jan.-Feb. 1999;27(1):134-42.
Bendele, Animal models of rheumatoid arthritis. J Musculoskelet Neuronal Interact. Jun. 2001;1(4):377-85.
Campochiaro, The complexity of animal model generation for complex diseases. JAMA. Feb. 17, 2010;303(7):657-8.

(56) References Cited

OTHER PUBLICATIONS

Center for Disease Control, Classification of Diseases and Injuries. ICD-9-CM Tabular List of Diseases (FY03). 748 pages, accessed online Sep. 10, 2015.

Chaichian et al., Targeted Therapies in Systemic Lupus Erythematosus: A State-of-the-Art Review. J Clin Cell Immunol. 2013;S6:8 pages.

Chiba, Emerging Therapeutic Strategies in Alzheimer's Disease. InTech, retrieved online at: http://dx.doi.org/10.5772/55293. Chapter 9, pp. 181-225, (2013).

Cyr et al., Recent progress on nuclear receptor RORgamma modulators. Bioorganic & Medicinal Chemistry Letters. 2016;26:4387-4393.

Damia et al., Contemporary pre-clinical development of anticancer agents—What are the optimal preclinical models? European Journal of Cancer. 2009;45:2768-2781.

Edwards et al., Molecular genetics of AMD and current animal models. Angiogenesis. 2007;10(2):119-32.

Elborn, Cystic fibrosis. The Lancet. Retrieved online at: http://dx.doi.org/10.1016/S0140-6736(16)00576-6. 13 pages. Apr. 29, 2016.

Flowers et al., How we treat chronic graft-versus-host disease. Blood. Jan. 22, 2015;125(4):606-15.

Fries et al., O-divinylbenzene and naphthalene. Ber Dtsch Chem Ges B. 1936;69:715-22.

Fries et al., o-Divinylbenzol und Naphtalin. Annalen der Chemie. 1937;533:72-92.

Galié et al., Guidelines for the diagnosis and treatment of pulmonary hypertension: the Task Force for the Diagnosis and Treatment of Pulmonary Hypertension of the European Society of Cardiology (ESC) and the European Respiratory Society (ERS), endorsed by the International Society of Heart and Lung Transplantation (ISHLT). Eur Heart J. Oct. 2009;30(20):2493-537.

Hackam et al., Translation of research evidence from animals to humans. JAMA. Oct. 11, 2006;296(14):1731-2.

Healthline, Overview. Retrieved online at: http://www.healthline.com/health/inflammatory-bowel-disease. 7 pages. (2005-2015).

Hynes et al., The discovery of (R)-2-(sec-butylamino)-N-(2-methyl-5-(methylcarbamoyl)phenyl) thiazole-5-carboxamide (BMS-640994)-A potent and efficacious p38alpha MAP kinase inhibitor. Bioorg Med Chem Lett. Mar. 15, 2008;18(6):1762-7.

Ito et al., A medium-term rat liver bioassay for rapid in vivo detection of carcinogenic potential of chemicals. Cancer Sci. Jan. 2003;94(1):3-8.

Johnson et al., Relationships between drug activity in NCl preclinical in vitro and in vivo models and early clinical trials. Br J Cancer. May 18, 2001;84(10):1424-31.

Jordan, Tamoxifen: a most unlikely pioneering medicine. Nat Rev Drug Discov. Mar. 2003;2(3):205-13.

Lamotte et al., Discovery of novel indazole derivatives as dual angiotensin II antagonists and partial PPAR? agonists. Bioorg Med Chem Lett. Feb. 15, 2014;24(4):1098-103.

Ledford, US cancer institute to overhaul tumour cell lines. Nature. Feb. 25, 2016;530(7591):391.

Lim et al., Age-related macular degeneration. Lancet. May 5, 2012;379(9827):1728-38.

Lutz et al., Overview of Animal Models of Obesity. Curr Protoc Pharmacol. Sep. 2012. Chapter: Unit 5.61. 22 pages.

Maddur et al., Th17 cells: biology, pathogenesis of autoimmune and inflammatory diseases, and therapeutic strategies. Am J Pathol. Jul. 2012;181(1):8-18.

Makrilakis, Pathophysiology of Type 2 diabetes. Diabetes in Clinical Practice: Questions and Answers from Case Studies. John Wiley & Sons, Ltd. Chapter 3, pp. 43-58, (2006).

Marcoux et al., Annulation of ketones with vinamidinium hexafluorophosphate salts: an efficient preparation of trisubstituted pyridines. Org Lett. Jul. 27, 2000;2(15):2339-41.

Ocana et al., Preclinical development of molecular-targeted agents for cancer. Nat Rev Clin Oncol. 2011;8:200-209.

Pilz et al., Modern multiple sclerosis treatment—what is approved, what is on the horizon. Drug Discov Today. Dec. 2008;13(23-24):1013-25.

Quinby, Conventional Therapy. Psoriasis and Psoriatic Arthritism. An Integrated Approach. Kenneth B. Gordon (Ed.), Springer-Verlag, Berlin Heidelberg. Chapter 9, pp. 134-184, (2005).

Sangshetti et al., Antileishmanial drug discovery: comprehensive review of the last 10 years. RSC Adv. 2015;5:32376-32415.

Schlecker et al., Regioselective Metalation of Pyridinylcarbamates and Pyridinecarboxamides with (2,2,6,6-Tetramethylpiperidino)magnesium Chloride. J Org Chem. 1995;60:8414-8416.

Schlecker et al., Regioselective Monometalation of 2,5-Pyridinedicarboxamides with (2,2,6,6-Tetramethylpiperidino)magnesium Chloride (TMPMgCl). Liebigs Ann. 1995;8:1441-1446.

Schonherr et al., Profound Methyl Effects in Drug Discovery and a Call for New C—H Methylation Reactions. Angew Chem Int Ed. 2013;52:12256-67.

Sharma et al., Cell line-based platforms to evaluate the therapeutic efficacy of candidate anticancer agents. Nat Rev Cancer. Apr. 2010;10(4):241-53.

Sime et al., Discovery of GSK1997132B a novel centrally penetrant benzimidazole PPAR? partial agonist. Bioorg Med Chem Lett. Sep. 15, 2011;21(18):5568-72.

STN Registry No. 1030136-78-7, 2H-Indazole-6-carboxamide, 1 page, (2020).

STN Registry No. 1030136-78-7. 2H-Indazole-6-carboxamide, N-[(4-chlorophenyl)methyl]-2-[{4-methoxyphenyl)methyl]. Jun. 24, 2008.

STN Registry No. 1115530-36-3, Thieno[2,3-d]pyrimidine-6-carboxamide, N-[(2-bromophenyl)methyl]-4-(4-ethyl-1-piperazinyl)-5-methyl. Mar. 4, 2009.

STN Registry No. 1141899-39-9, 6-Isoquinolinecarboxamide, N-((2,4-dichlorophenyl)methyl)-1,2,3,4-tetrahydro-2-(4-(methylamino)-6-phenyl-1,3,5-triazine-2-yl). May 1, 2009.

STN Registry No. 1346976-76-8, 2H-Indazole-6-carboxamide, 2-[2-[5-(aminocarbonyl)-1H-pyrazol-1-yl]ethyl]-N-[(3-chlorophenyl)methyl]. Dec. 1, 2011.

STN Registry No. 926926-48-9, 6-Isoquinolinecarboxamide, N-(cyclopropylmethyl)-2-(6,7-dimethoxy-4-quinazolinyl)-1,2,3,4-tetrahydro. Mar. 18, 2007.

University of Cambridge, Alzheimer's disease and tauopathy. John van Geest Centre for Brain Repair, School of Clinical Medicine. 1 page, (2016).

Vickers et al., The utility of animal models to evaluate novel anti-obesity agents. Br J Pharmacol. Oct. 2011;164(4):1248-62.

Vourloumis et al., Solid-phase synthesis of benzimidazole libraries biased for RNA targets. Tetrahedron Letters. 2003;44:2807-2811.

Wang et al., Structure-Based Design of Tetrahydroisoquinoline-7-carboxamides as Selective Discoidin Domain Receptor 1 (DDR1) Inhibitors. J Med Chem. Jun. 23, 2016;59(12):5911-6.

Yan et al., Quality control in combinatorial chemistry: determination of the quantity, purity, and quantitative purity of compounds in combinatorial libraries. J Comb Chem. Sep.-Oct. 2003;5(5):547-59.

European Office Action for Application No. 16816023.2, dated Jun. 27, 2019, 6 pages.

Copending U.S. Appl. No. 16/751,739, filed Jan. 24, 2020.

Chauhan et al., Autoimmunity in Dry Eye is due to Resistance of Th17 to Treg Suppression. J Immunol. Feb. 1, 2009;182(3):1247-52.

Chauhan et al., Role of Th17 Cells in the Immunopathogenesis of Dry Eye Disease. Mucosal Immunol. 2009;2(4):375-6.

STN Registry No. 434289-52-8, Thieno[2,3-d]pyrimidine-6-carboxamide, N-](4-fluorophenyl)methyl]-2,5-dimethyl-4-(1-piperidinyl), 1 page, Jun. 27, 2002.

Co-pending U.S. Appl. No. 17/015,825, filed Sep. 9, 2020.

Co-pending U.S. Appl. No. 17/032,428, filed Sep. 25, 2020.

Co-pending U.S. Appl. No. 17/023,871, filed Sep. 17, 2020.

\* cited by examiner

INHIBITORS OF ROR GAMMA

RELATED APPLICATIONS

This application is a 35 U.S.C. § 371 national stage filing of international application No. PCT/US2018/043463, filed Jul. 24, 2018, which claims the benefit of priority to international application No. PCT/CN2017/094043, filed Jul. 24, 2017, the entire contents of each of which are incorporated herein by reference.

BACKGROUND

Retinoic acid receptor-related orphan receptors (RORs) are a subfamily of transcription factors in the steroid hormone nuclear receptor superfamily (Jetten & Joo (2006) Adv. Dev. Biol. 2006, 16, 313-355). The ROR family consists of ROR alpha (RORα), ROR beta (RORβ) and ROR gamma (RORγ), each encoded by a separate gene (in human: RORA, RORB and RORC, respectively; in mouse: rora, rorb and rorc, respectively). RORs contain four principal domains shared by the majority of nuclear receptors: an N-terminal domain, a highly conserved DNA-binding domain (DBD) consisting of two zinc finger motifs, a hinge domain, and a ligand binding domain (LBD). RORγ has two isoforms: RORγ1 and RORγ2 (also known as RORγt). RORγ1 is expressed in a variety of tissues including thymus, muscle, kidney and liver, while RORγt is exclusively expressed in the cells of the immune system. RORγt has a critical role in thymopoiesis and the development of several secondary lymphoid tissues, and is a key regulator of Th17 cell differentiation (Jetten, 2009, Nucl. Recept. Signal., 7:e003, doi:10.1621/nrs.07003, Epub 2009 Apr. 3). Th17 cells are a subset of T helper cells which preferentially produce the pro-inflammatory cytokines IL-17A, IL-17F, IL-21 and IL-22. Th17 cells and their effector molecules, such as IL-17, IL-21, IL-22, GM-CSF and CCL20, are associated with the pathogenesis of several autoimmune and inflammatory diseases, such as rheumatoid arthritis, systemic lupus erythematosus, multiple sclerosis, psoriasis, inflammatory bowel disease, allergy and asthma (Maddur et al., 2012, Am. J. Pathol., 181:8-18). They are also important in the pathogenesis of acne (Thiboutot et al., 2014, J. Invest. Dermatol., 134(2):307-10, doi: 10.1038/jid.2013.400; Agak et al., 2014, J. Invest. Dermatol., 134(2):366-73, doi: 10.1038/jid.2013.334, Epub 2013 Aug. 7), inflammation associated with endometriosis (Hirata et al., 2010, Endocrinol., 151:5468-5476; Hirata et al., 2011, Fertil Steril., July; 96(1):113-7, doi: 10.1016/j.fertnstert.2011.04.060, Epub 2011 May 20), and many other conditions such as multiple sclerosis, rheumatoid arthritis, cancer, metabolic syndrome, obesity hepatosteatosis, insulin resistance, and diabetes (Meissburger et al., 2011, EMBO Mol. Med., 3:637-651; Tosolini et al., 2011, Cancer Res., 71:1263-1271, doi: 10.1158/0008-5472.CAN-10-2907, Epub 2011 Feb. 8; Su et al., 2014, Immunol. Res., 58:118-124, doi: 10.1007/s12026-013-8483-y, Epub 2014 Jan. 9; Carmi et al., 2011, J. Immunol., 186:3462-3471, doi: 10.4049/jimmunol.1002901, Epub 2011 Feb. 7; Chen et al., 2013, Histopathology, 63:225-233, doi: 10.1111/his.12156, Epub 2013 Jun. 6).

Compound 1 is an inhibitor of RORγ and has therapeutic properties against a number of RORγ mediated diseases. Compound 1 is exemplified in U.S. Pat. No. 9,266,886 and has the formula:

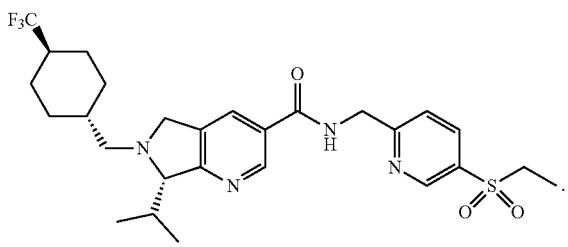 [SMILES: CCS(=O)(=O)c1ccc(CNC(=O)c2cnc3c(c2)CN(C[C@H]2CC[C@H](C(F)(F)F)CC2)[C@H]3C(C)C)nc1]

Despite its potential for commercialization, Compound 1 is susceptible to oxidation, particularly in solution. This makes it difficult to formulate pharmaceutically acceptable salts and polymorphs which are amendable to large scale manufacturing and formulating. Thus, the need to generate alternative forms for this potent inhibitor remains.

SUMMARY

In one aspect, provided herein are stable hydrogen bromide salt forms of Compound 1. Unlike other salt forms, the disclosed HBr salts can be prepared with minimal concern for degradation or minimal need for special precautions such as working in oxygen free atmospheres. See e.g., the Exemplification section below.

In another aspect, specific mono- and bis-hydrogen bromide crystalline salts of Compound 1 are disclosed, as well as methods for their preparation. Of the five characterized crystalline salt forms, Form D was found to have significantly less moisture update than other solid forms and to be more reproducible at large scale syntheses, thus making this form an attractive option for commercial processing.

During production of the bis-hydrogen bromide salt, initial attempts employed a two-step process started from Compound 1. This process involved the formation and isolation of a mono-hydrogen bromide salt by treatment with hydrobromic acid followed by a second independent treatment step with hydrobromic acid to form a bis-hydrogen bromide salt of Compound 1. This two-step method was utilized because initial attempts to produce a purified version of the bis-hydrogen bromide salt directly (i.e., without first isolating the mono-bromide salt) did not afford the desired level of purity required for large batch processing. The disclosed two-step method required the use of HBr and MeOH during the final steps of the synthesis. This transformation led to contamination of the product from production of MeBr. This problem was subsequently solved by slurrying the product in a mixture of isopropyl acetate and water. Thus, in addition to the two step method and the formation of the mono- and bis-hydrogen bromide salt, disclosed herein are methods of removing methyl bromide from a composition comprising methyl bromide and crystalline form D bis-hydrogen bromide salt of Compound 1.

A one step process of forming the disclosed bis-hydrogen bromide salt directly from Compound 1 was also found. In this aspect, neutralizing the reductive amination reaction mixture, thereby resulting in precipitation, provided Compound 1 as a free base in high purity and good yield, particularly on a larger scale. For example, reactions were effective at >3 kg scale with 98% yield and in >99 area % purity. See e.g., the Exemplification section. From this, treatment with a sufficient amount of hydrobromic acid afforded the desired bis-hydrogen bromide salt without the need to use MeOH. While no detectable contamination from MeBr was observed, this process led to the formation of a mixture of crystalline forms: Form E, Form F, and Form G. This problem, however, was solved by slurrying the product in a mixture of isopropyl acetate and water to afford a single bis-hydrogen bromide crystal form of Compound 1, i.e., Form D. Thus, in addition to the one-step process, provided herein are methods of converting crystalline Forms E, F and G of a bis-hydrogen bromide salt of Compound 1 to Form D crystalline bis-hydrogen bromide salt of Compound 1.

Also provided herein are methods of using the disclosed forms such treat a disease or disorder mediated by RORγ.

DETAILED DESCRIPTION

Figure 1:
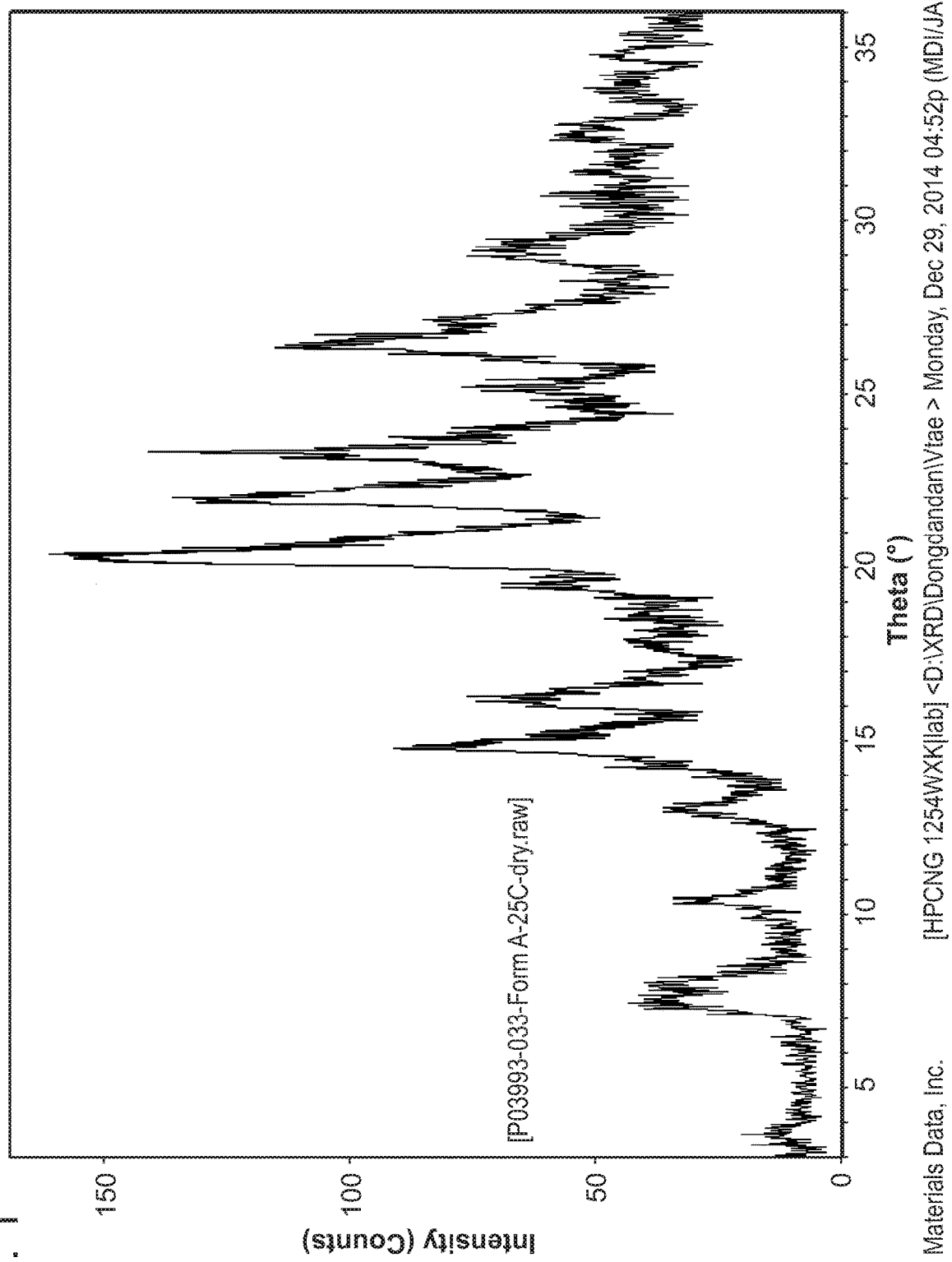
FIG. 1. depicts an X-ray powder diffraction pattern (XRPD) for Form A of Compound 1.

In one aspect, provided herein is a mono-hydrogen bromide salt having the formula:

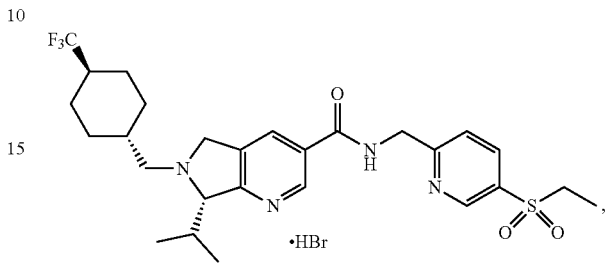

wherein the mono-hydrogen bromide salt has a purity of >95% such as, e.g., >96%, >97%, >98%, or >99%, or 99.5% or greater.

In another aspect, provided herein is a bis-hydrogen bromide salt having the formula:

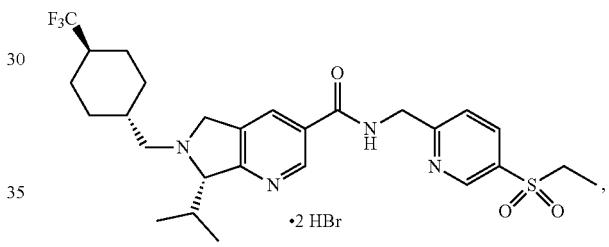

wherein the bis-hydrogen bromide salt has a purity of >95% such as, e.g., >96%, >97%, >98%, >99%, or 99.5% or greater.

In other aspects, provided herein are crystalline Forms A, B, C, D, and E of Compound 1.

In yet other aspects, provided herein are methods of manufacturing one or more of the salt and crystalline forms described herein.

1. Definitions

When used alone, the term "Form A" refers to the crystalline polymorph Form A of Compound 1. The terms "Form A", "Form A of Compound 1", and "crystalline Form A of Compound 1" are used interchangeably. Similarly, when used alone, the term "Form B" refers to the crystalline polymorph Form B of Compound 1. The terms "Form B", "Form B of Compound 1", and "crystalline Form B of Compound 1" are used interchangeably. Similarly, when used alone, the term "Form C" refers to the crystalline polymorph Form C of Compound 1. The terms "Form C", "Form C of Compound 1", and "crystalline Form C of Compound 1" are used interchangeably. Similarly, when used alone, the term "Form D" refers to the crystalline polymorph Form D of Compound 1. The terms "Form D", "Form D of Compound 1", and "crystalline Form D of Compound 1" are used interchangeably. Similarly, when used alone, the term "Form E" refers to the crystalline polymorph Form E of Compound 1. The terms "Form E", "Form E of Compound 1", and "crystalline Form E of Compound 1" are used interchangeably.

The term "amorphous" means a solid that is present in a non-crystalline state or form. Amorphous solids are disordered arrangements of molecules and therefore possess no distinguishable crystal lattice or unit cell and consequently have no definable long range ordering. Solid state ordering of solids may be determined by standard techniques known in the art, e.g., by X-ray powder diffraction (XRPD) or differential scanning calorimetry (DSC). Amorphous solids can also be differentiated from crystalline solids e.g., by birefringence using polarized light microscopy.

When used in reference to the mono- and bis-hydrogen bromide salt forms of Compound 1, as well as the polymorphic forms described herein, but not including solvated forms of these compounds, "purity" is expressed in terms of percentage and can be calculated by dividing the mass of the mono- and bis-hydrogen bromide salt forms of Compound 1 by the total mass of the sample, and then multiplying this number by 100. Thus, 90% pure or has a purity of 90% means that the designated mono- or bis-hydrogen bromide salt form of Compound 1, or designated polymorphic form makes up 90% by weight of the sample. In one aspect, the purity of the salt and crystalline forms described herein are >90%, >95%, >97%, and >99% pure (e.g., >99.1%, 99.2%, 99.3%, 99.4%, 99.5%, 99.6%, 99.7%, 99.8%, and 99.9%) by weight. In one aspect, the purity of the salt and crystalline forms described herein are >90%, >95%, >97%, and >99% pure (e.g., >99.1%, 99.2%, 99.3%, 99.4%, 99.5%, 99.6%, 99.7%, 99.8%, and 99.9%) by weight and free from other salt or polymorphic forms.

When purity is defined in terms of area such as >99% area, it will be understood that this refers to the purity of the identified compound as determined by the HPLC peak area percentage.

The term "pharmaceutically acceptable carrier" refers to a non-toxic carrier, adjuvant, or vehicle that does not adversely affect the pharmacological activity of the compound with which it is formulated, and which is also safe for human use. Pharmaceutically acceptable carriers, adjuvants or vehicles that may be used in the compositions of this disclosure include, but are not limited to, ion exchangers, alumina, aluminum stearate, magnesium stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances (e.g., microcrystalline cellulose, hydroxypropyl methylcellulose, lactose monohydrate, sodium lauryl sulfate, and crosscarmellose sodium), polyethylene glycol, sodium carboxymethylcellulose, polyacrylates, waxes, polyethylene-polyoxypropylene-block polymers, polyethylene glycol and wool fat.

The terms "treatment," "treat," and "treating" refer to reversing, alleviating, delaying the onset of, or inhibiting the progress of a disease or disorder, or one or more symptoms thereof, as described herein. In one embodiment, treatment may be administered after one or more symptoms have developed, i.e., therapeutic treatment. In other embodiments, treatment may be administered in the absence of symptoms. For example, treatment may be administered to a susceptible individual prior to the onset of symptoms (e.g., in light of a history of symptoms and/or in light of genetic or other susceptibility factors), i.e., prophylactic treatment. Treatment may also be continued after symptoms have resolved, for example to reduce the likelihood of obtaining or to delay recurrence.

The 2-theta values of the X-ray powder diffraction patterns for the crystalline forms described herein may vary slightly from one instrument to another and also depending on variations in sample preparation and batch to batch variation. Therefore, the XRPD patterns/assignments recited herein are not to be construed as absolute and can vary ±0.2 degrees.

"Substantially the same XRPD pattern" means that for comparison purposes, at least 90% of the peaks shown are present. It is to be further understood that for comparison purposes some variability in peak intensities from those shown are allowed, such as ±0.2 degrees.

2. Compounds

In one aspect, the present disclosure provides crystalline Form A, crystalline Form B, crystalline Form C, crystalline Form D, and crystalline Form E of Compound 1.

Figure 2:
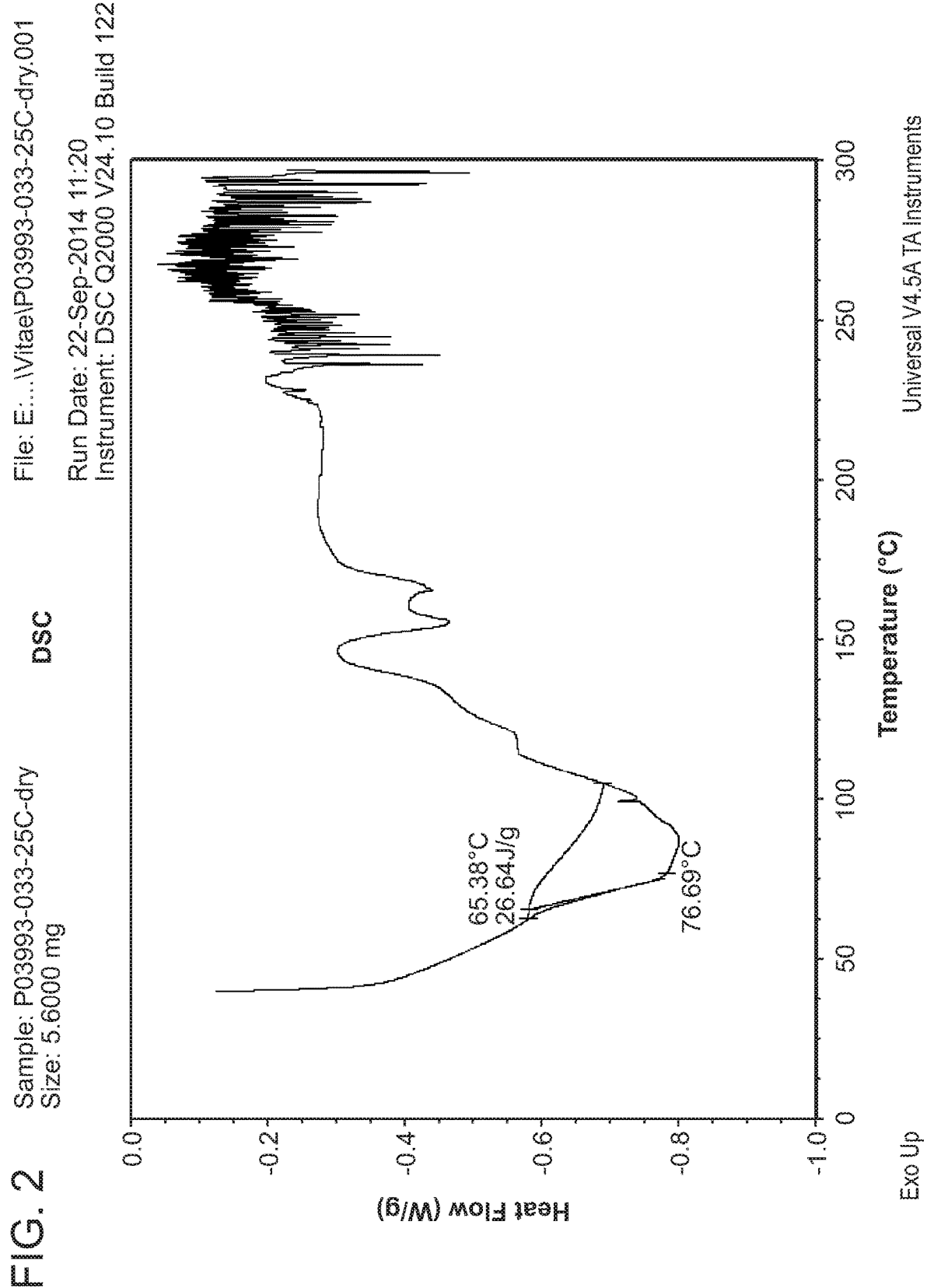
FIG. 2. depicts a Differential Scanning calorimetry (DSC) spectrum for Form A of Compound 1.
Figure 3:
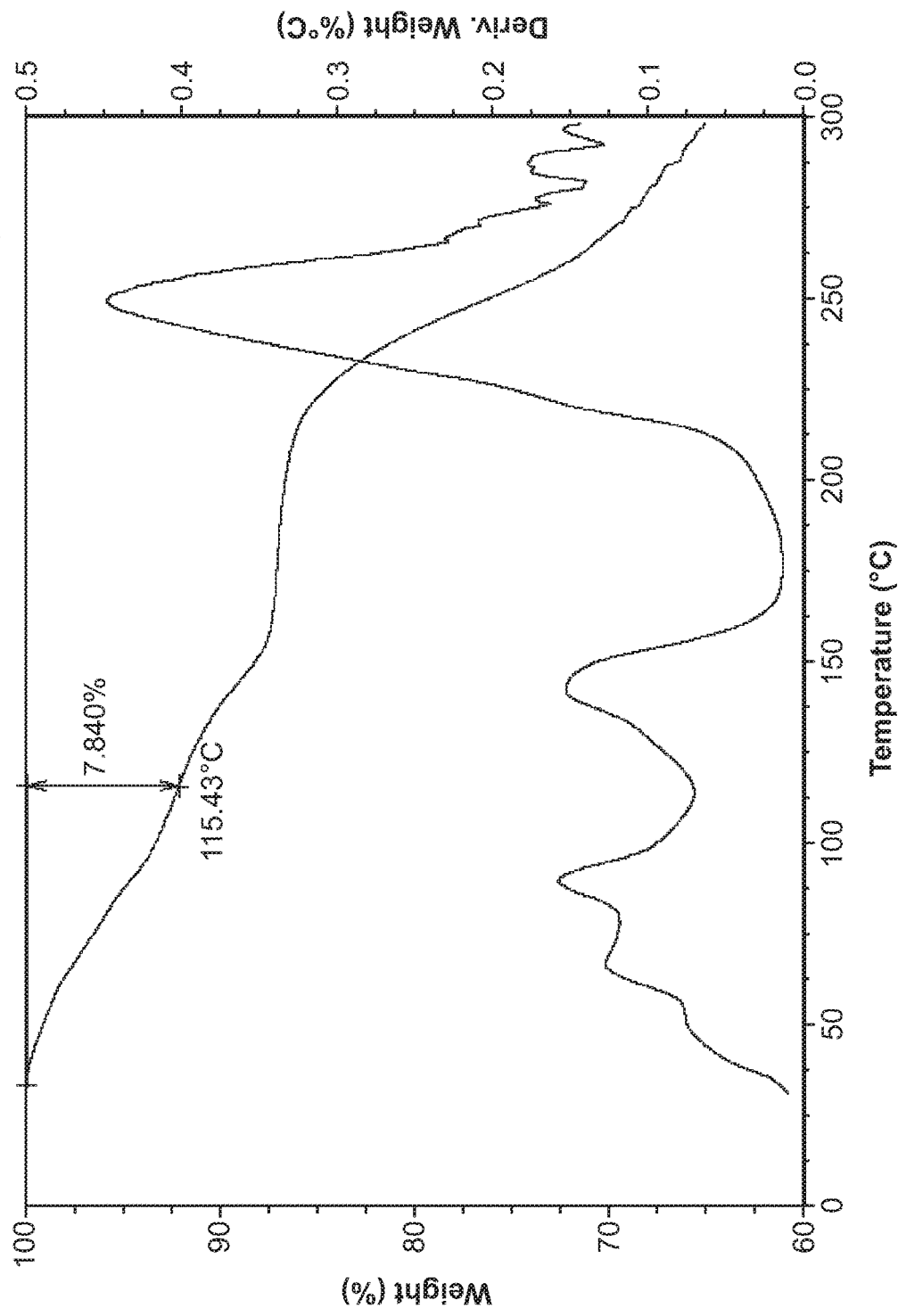
FIG. 3. depicts a thermal gravimetric analysis (TGA) pattern for Form A of Compound 1.

In one aspect, crystalline Form A of Compound 1 is characterized by at least three, at least four, or at least five x-ray powder diffraction peaks at 2Θ angles selected from 14.90°, 20.28°, 20.70°, 22.00°, 23.34°, and 26.46°. Alternatively, crystalline Form A of Compound 1 is characterized by x-ray powder diffraction peaks at 2Θ angles 14.90°, 20.28°, 20.70°, 22.00°, 23.34°, and 26.46. In another alternative, crystalline Form A of Compound 1 is characterized by at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least twenty-one, at least twenty-two, at least twenty-three, at least twenty-four, at least twenty-five, at least twenty-six, at least twenty-seven, at least twenty-eight, at least twenty-nine, at least thirty, at least thirty-one, at least thirty-two, at least thirty-three, at least thirty-four, at least thirty-five, at least thirty-six, at least thirty seven or at least thirty-eight x-ray powder diffraction peaks at 2Θ angles selected from Table 4. In another alternative, crystalline Form A of compound 1 is characterized by x-ray powder diffraction peaks at 7.54°, 8.04°, 14.24°, 14.90°, 16.32°, 20.28°, 20.70°, 22.00°, 23.34°, and 26.46°. In another alternative, crystalline Form A of Compound 1 is characterized by x-ray powder diffraction peaks in Table 4. In another aspect, crystalline Form A of Compound 1 has an XRPD pattern that is substantially the same XRPD pattern shown in FIG. 1. In another aspect, crystalline Form A of Compound 1 has a DSC pattern that is substantially the same DSC pattern shown in FIG. 2. In another aspect, crystalline Form A of Compound 1 has a TGA pattern that is substantially the same TGA pattern shown in FIG. 3. In one aspect, the crystalline Form A of Compound 1 is a bis-hydrogen bromide salt having one or more of the XRPD peaks defined above.

Figure 5:
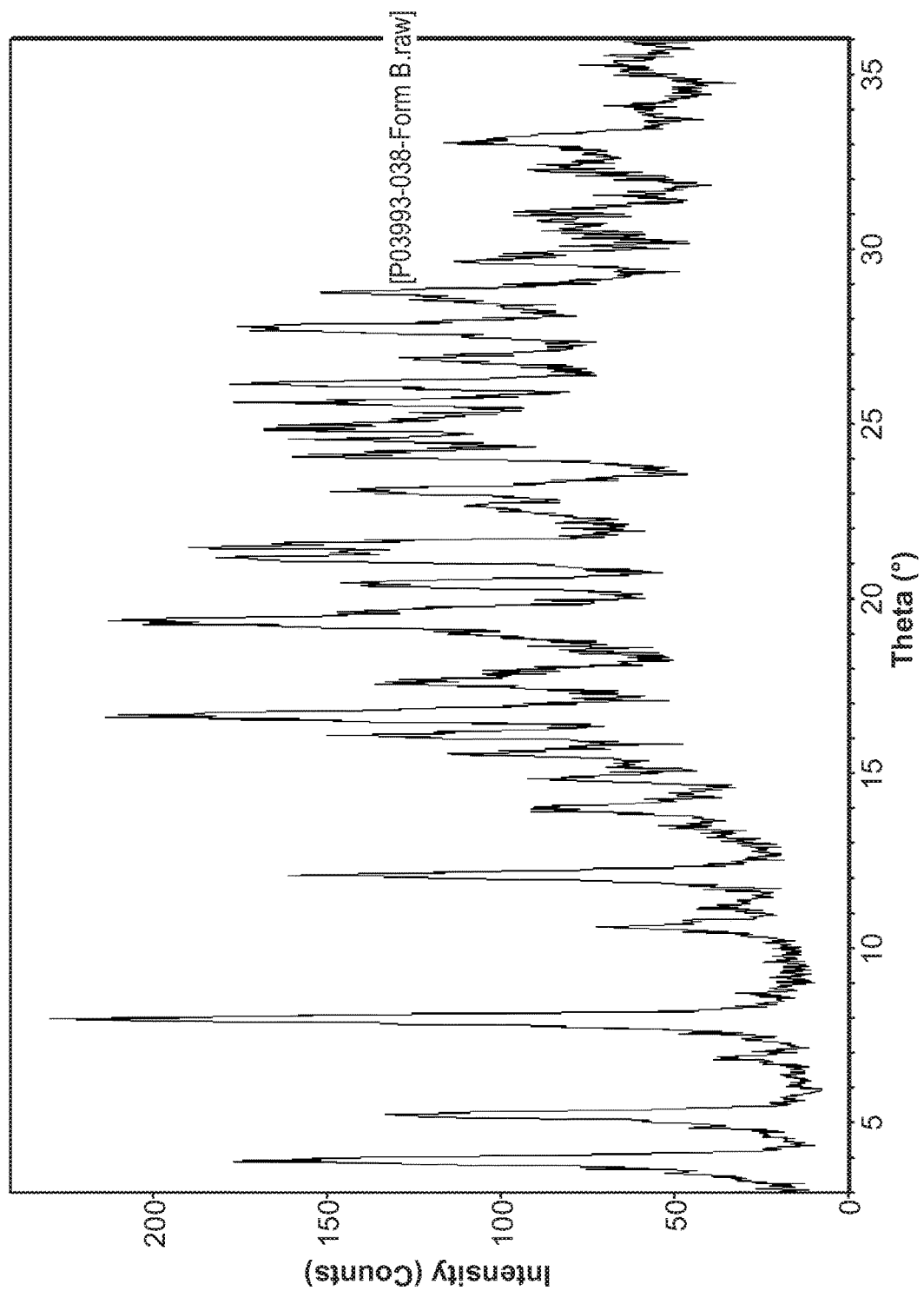
FIG. 5. depicts an X-ray powder diffraction pattern (XRPD) for Form B of Compound 1.
Figure 6:
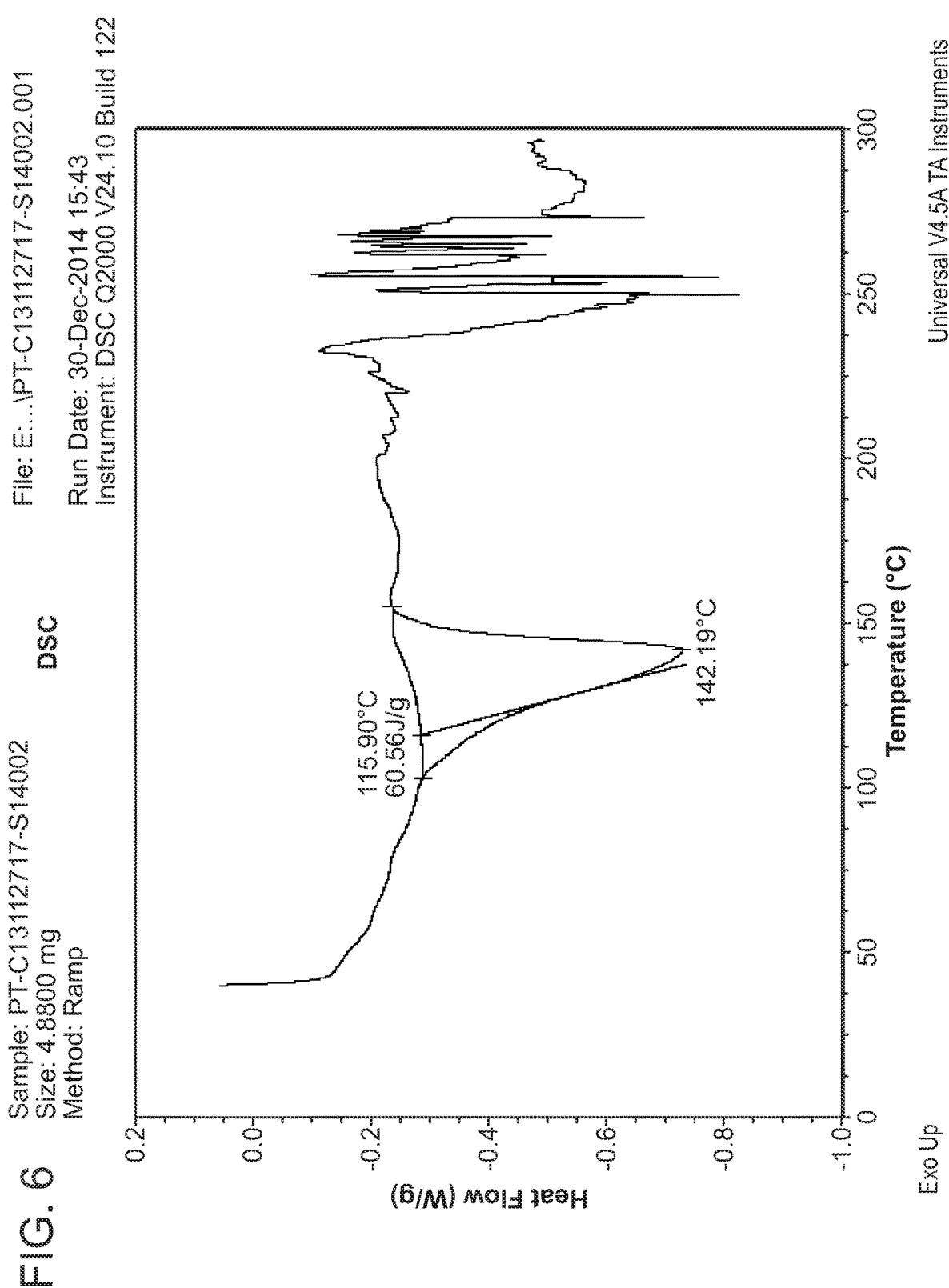
FIG. 6. depicts a Differential Scanning calorimetry (DSC) spectrum for Form B of Compound 1.
Figure 7:
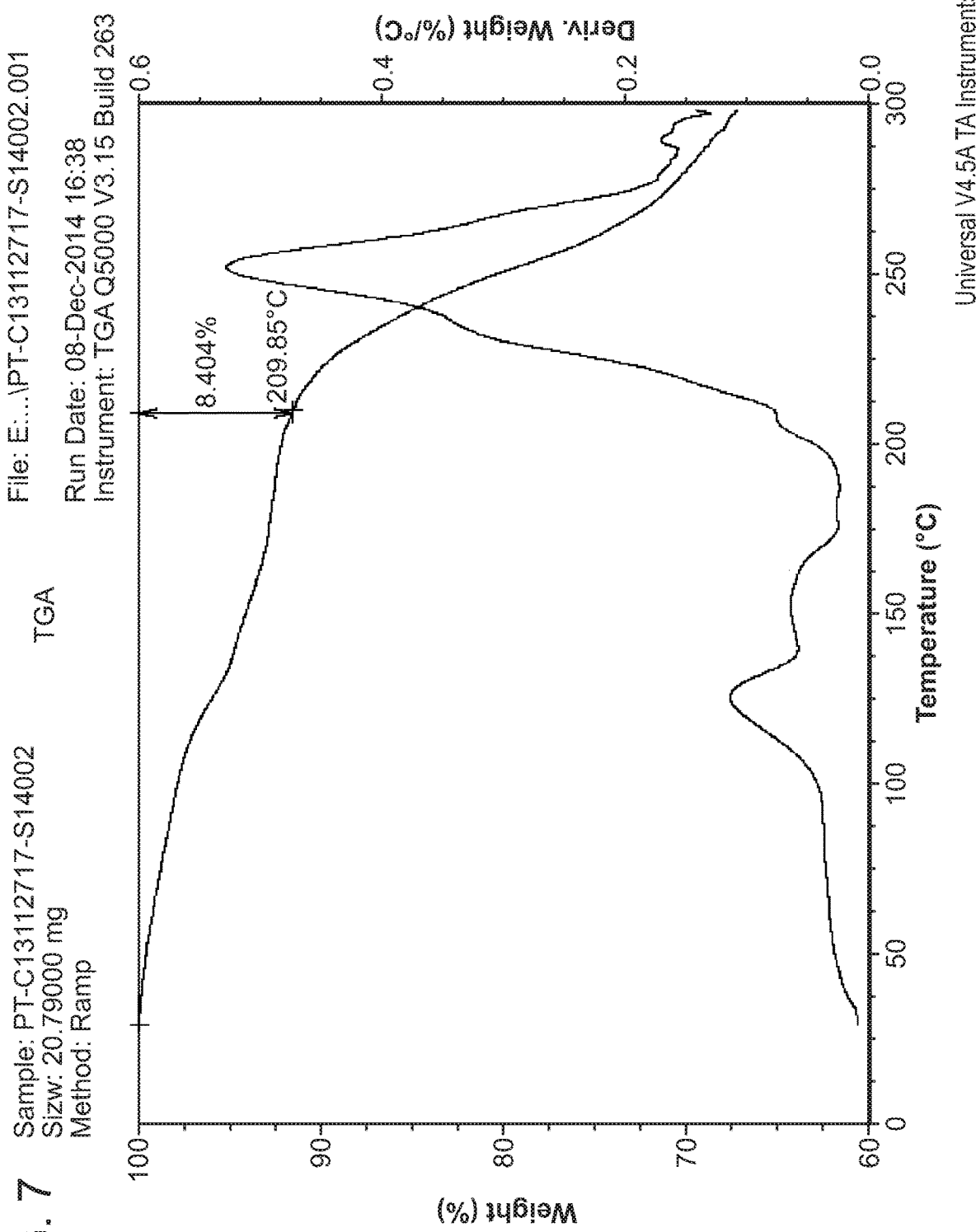
FIG. 7. depicts a thermal gravimetric analysis (TGA) pattern for Form B of Compound 1.

In one aspect, crystalline Form B of Compound 1 is characterized by at least three, at least four, or at least five x-ray powder diffraction peaks at 2Θ angles selected from 5.24°, 7.98°, 12.12°, 19.42°, 21.18°, and 21.52°. Alternatively, crystalline Form B of Compound 1 is characterized by x-ray powder diffraction peaks at 2Θ angles 5.24°, 7.98°, 12.12°, 19.42°, 21.18°, and 21.52°. In another alternative, crystalline Form B of Compound 1 is characterized by at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least twenty-one, at least twenty-two, at least twenty-three, at least twenty-four, at least twenty-five, at least twenty-six, at least twenty-seven, at least twenty-eight, at least twenty-nine, at least thirty, at least thirty-one, at least thirty-two, at least thirty-three, at least thirty-four, at least thirty-five, at least thirty-six, at least thirty seven, at least thirty-eight, at least thirty-nine, at least forty, or at least forty-one x-ray powder diffraction peaks at 2Θ angles selected from Table 5. In another alternative, crystalline Form B of compound 1 is characterized by x-ray powder diffraction peaks at 3.94°, 5.24°, 7.98°, 12.12°, 16.64°, 19.42°, 21.18°, and 21.52°, 26.18°, and 27.80°. In another alternative, crystalline Form B of Compound 1 is characterized by x-ray powder diffraction peaks in Table 5. In another aspect, crystalline Form B of Compound 1 has an XRPD pattern that is substantially the same XRPD pattern shown in FIG. 5. In another aspect, crystalline Form B of Compound 1 has a DSC pattern that is substantially the same DSC pattern shown in FIG. 6. In another aspect, crystalline Form B of Compound 1 has a TGA pattern that is substantially the same TGA pattern shown in FIG. 7. In one aspect, the crystalline Form B of Compound 1 is a mono-hydrogen bromide salt having one or more of the XRPD peaks defined above. In one aspect, the crystalline Form B of Compound 1 is a solvate having one or more of the XRPD peaks defined above. In another aspect, the crystalline Form B of Compound 1 is an isopropanol solvate having one or more of the XRPD peaks defined above. In yet another aspect, the crystalline Form B of Compound 1 is a mono-hydrogen bromide salt isopropanol solvate having one or more of the XRPD peaks defined above.

Figure 9:
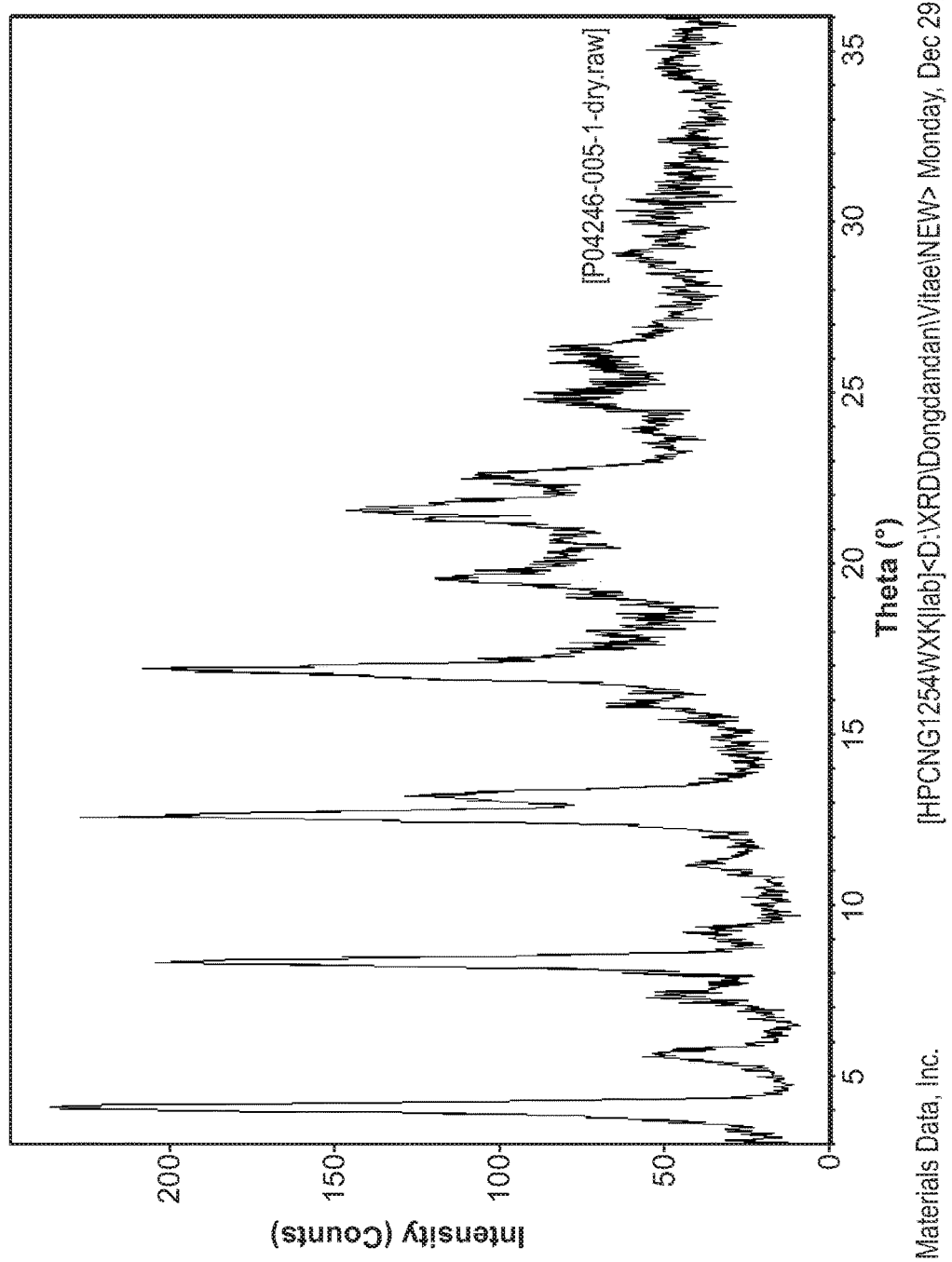
FIG. 9. depicts an X-ray powder diffraction pattern (XRPD) for Form C of Compound 1.
Figure 10:
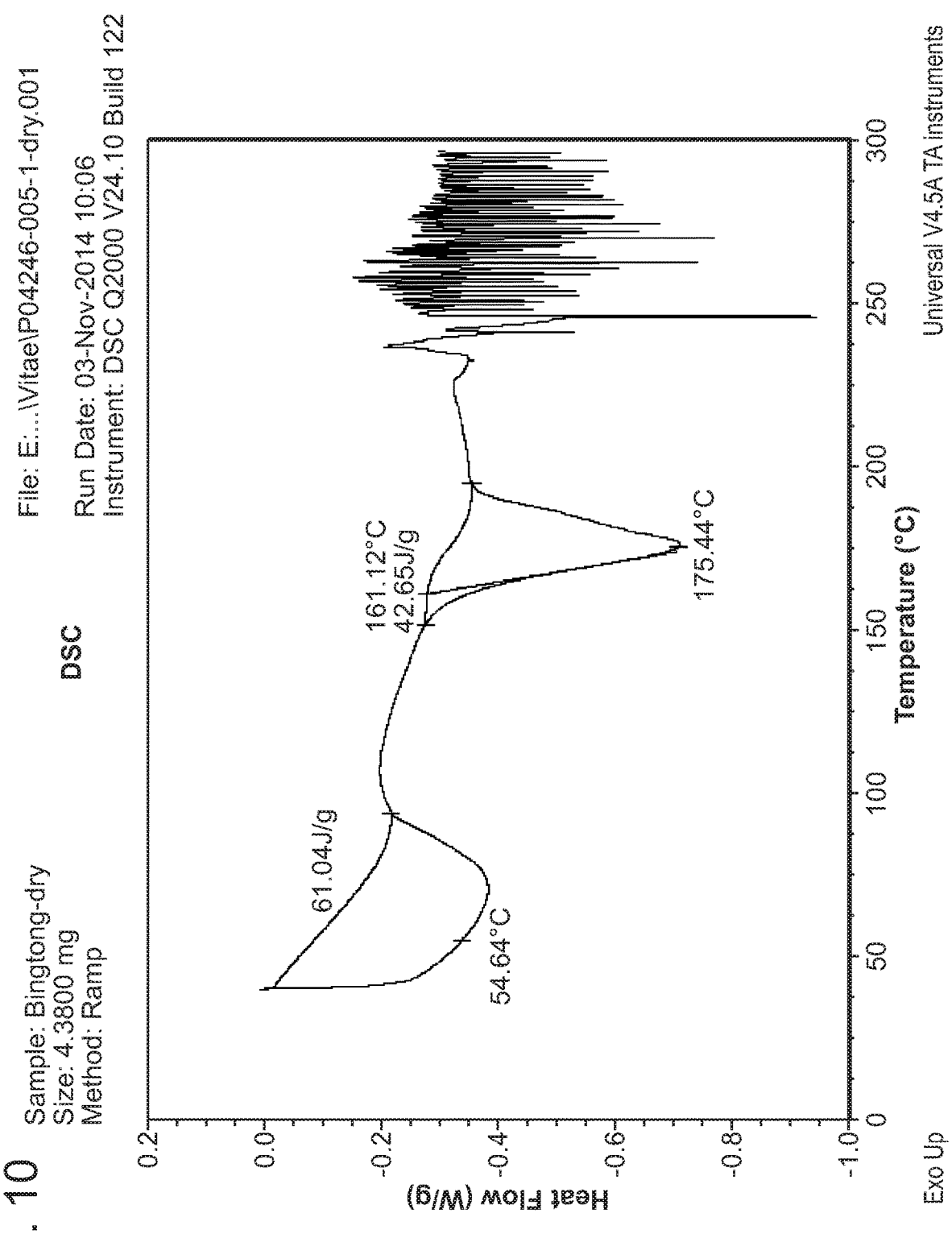
FIG. 10. depicts a Differential Scanning calorimetry (DSC) spectrum for Form C of Compound 1.
Figure 11:
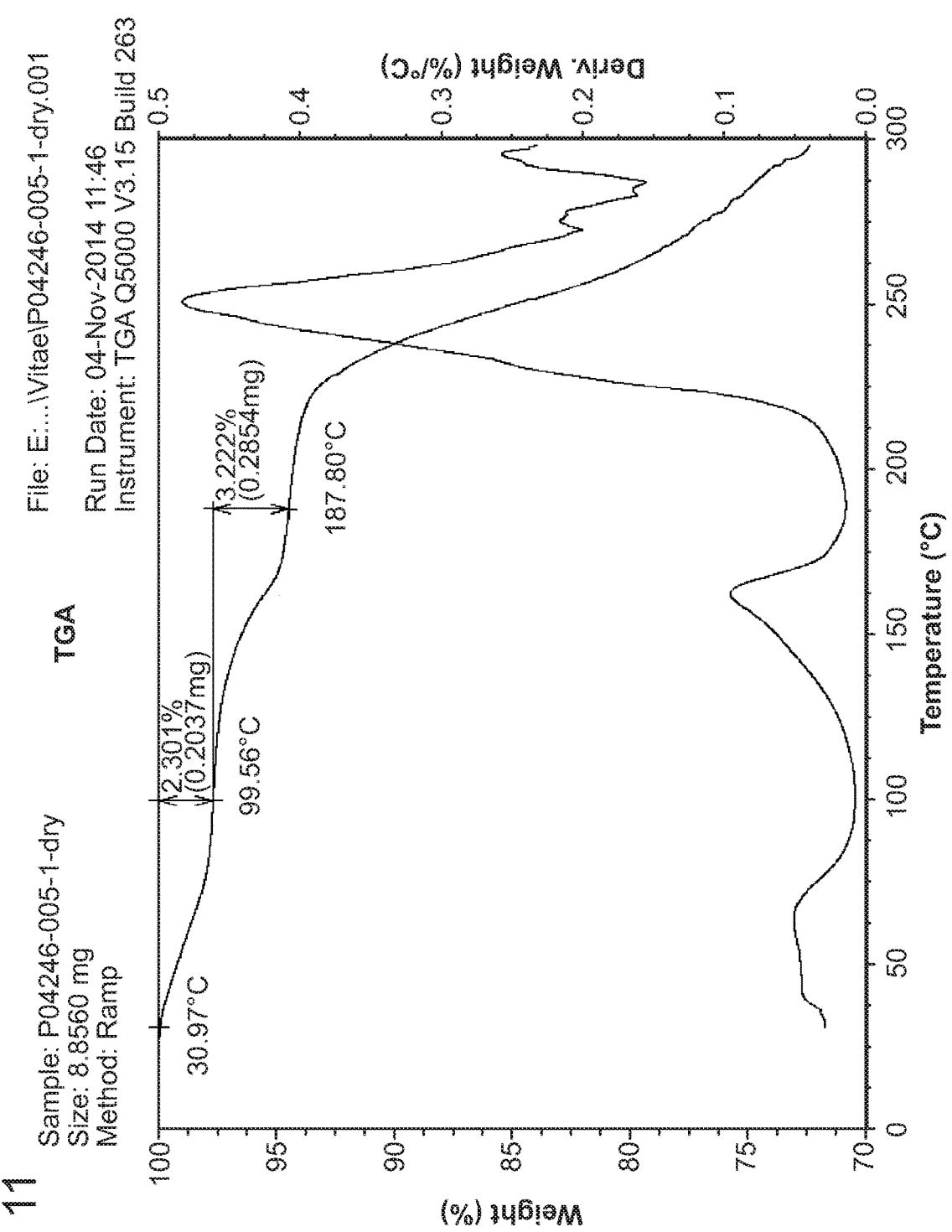
FIG. 11. depicts a thermal gravimetric analysis (TGA) pattern for Form C of Compound 1.

In one aspect, crystalline Form C of Compound 1 is characterized by at least three, at least four, or at least five x-ray powder diffraction peaks at 2Θ angles selected from 20.28°, 20.70°, 23.18°, 23.34°, 25.24°, and 26.46. Alternatively, crystalline Form C of Compound 1 is characterized by x-ray powder diffraction peaks at 2Θ angles 20.28°, 20.70°, 23.18°, 23.34°, 25.24°, and 26.46. In another aspect, crystalline Form C of Compound 1 has an XRPD pattern that is substantially the same XRPD pattern shown in FIG. 9. In another aspect, crystalline Form C of Compound 1 has a DSC pattern that is substantially the same DSC pattern shown in FIG. 10. In another aspect, crystalline Form C of Compound 1 has a TGA pattern that is substantially the same TGA pattern shown in FIG. 11. In one aspect, the crystalline Form C of Compound 1 is a bis-hydrogen bromide salt having one or more of the XRPD peaks defined above.

Figure 13:
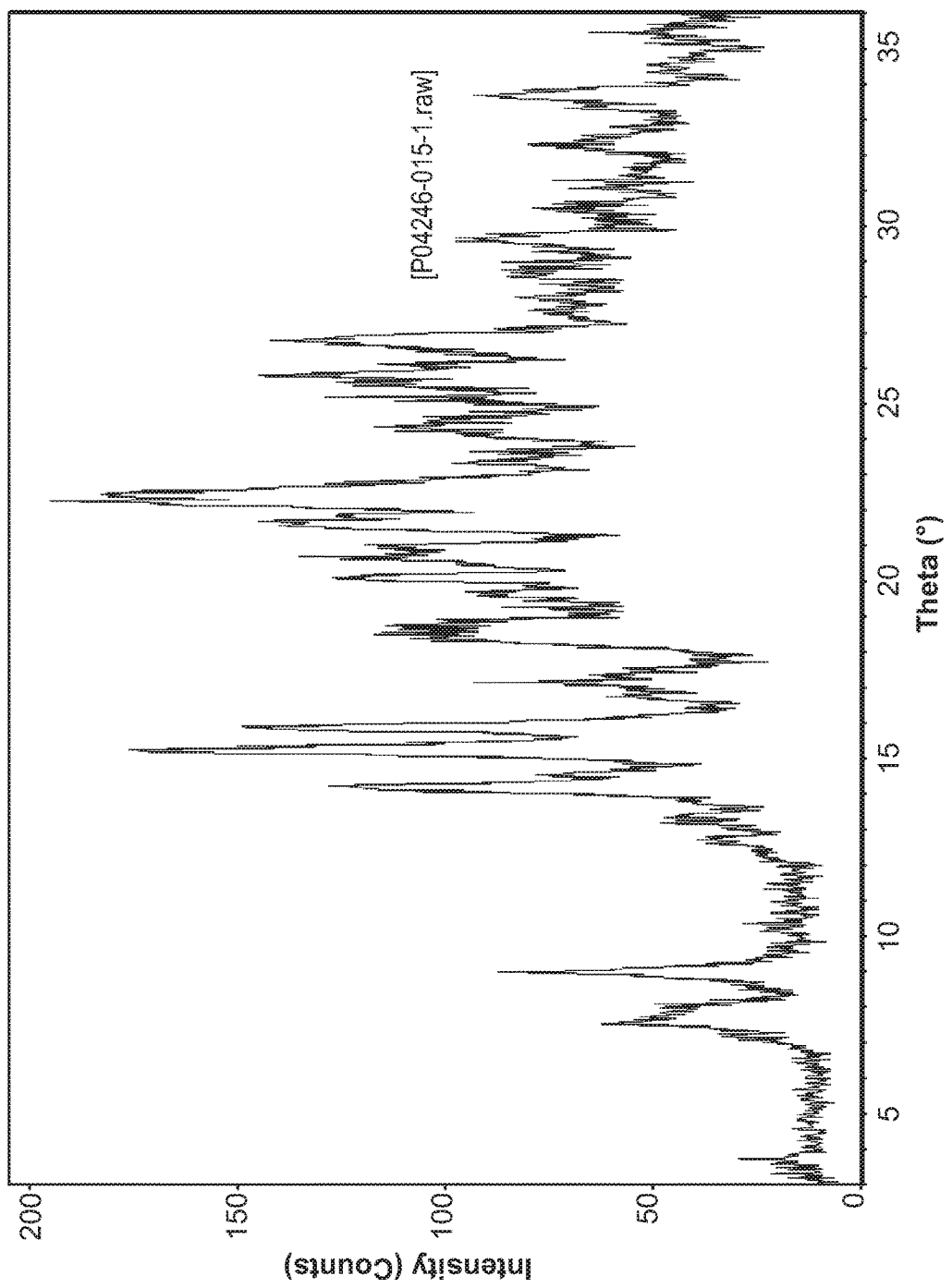
FIG. 13. depicts an X-ray powder diffraction pattern (XRPD) for Form D of Compound 1.
Figure 14:
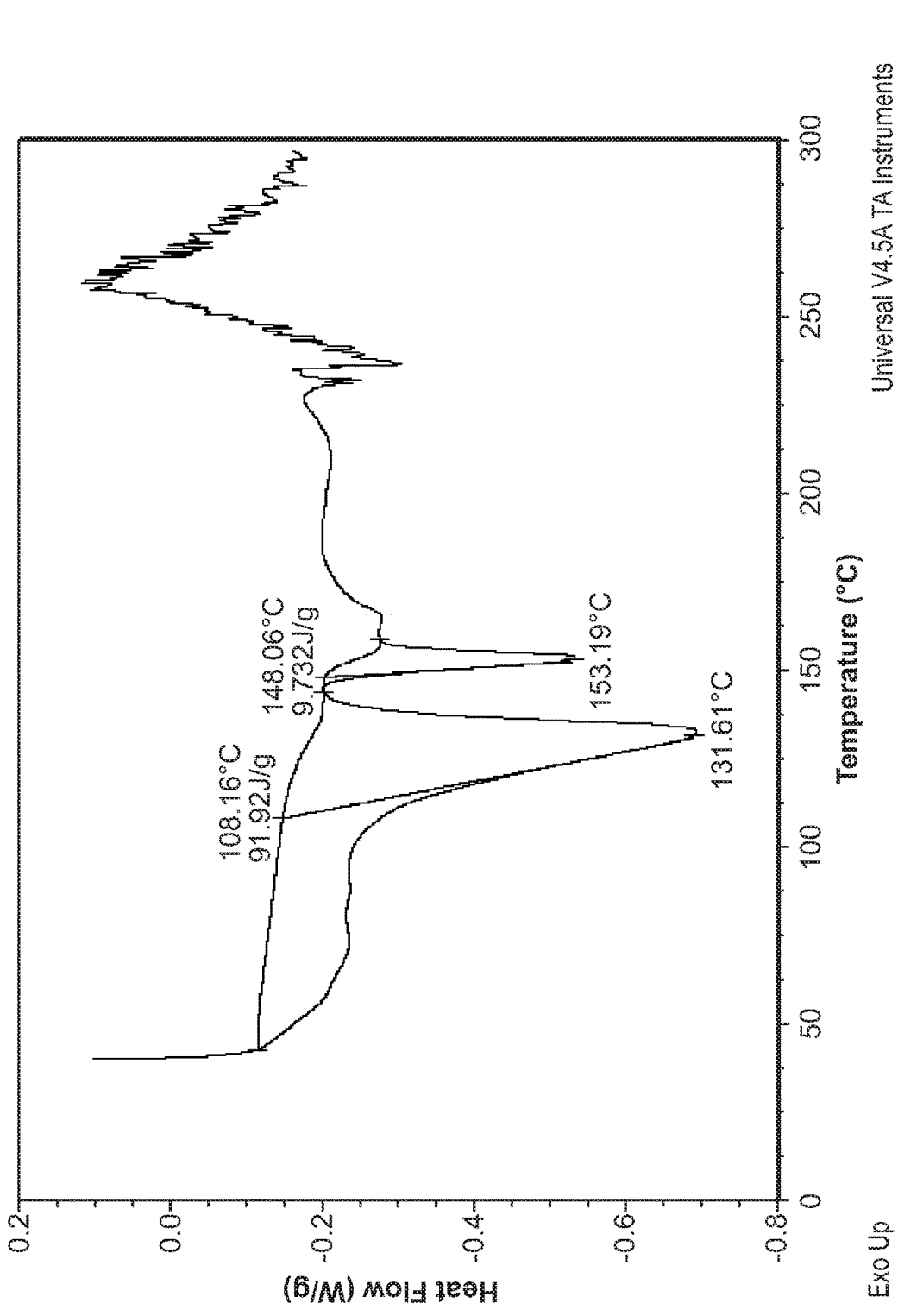
FIG. 14. depicts a Differential Scanning calorimetry (DSC) spectrum for Form D of Compound 1.
Figure 15:
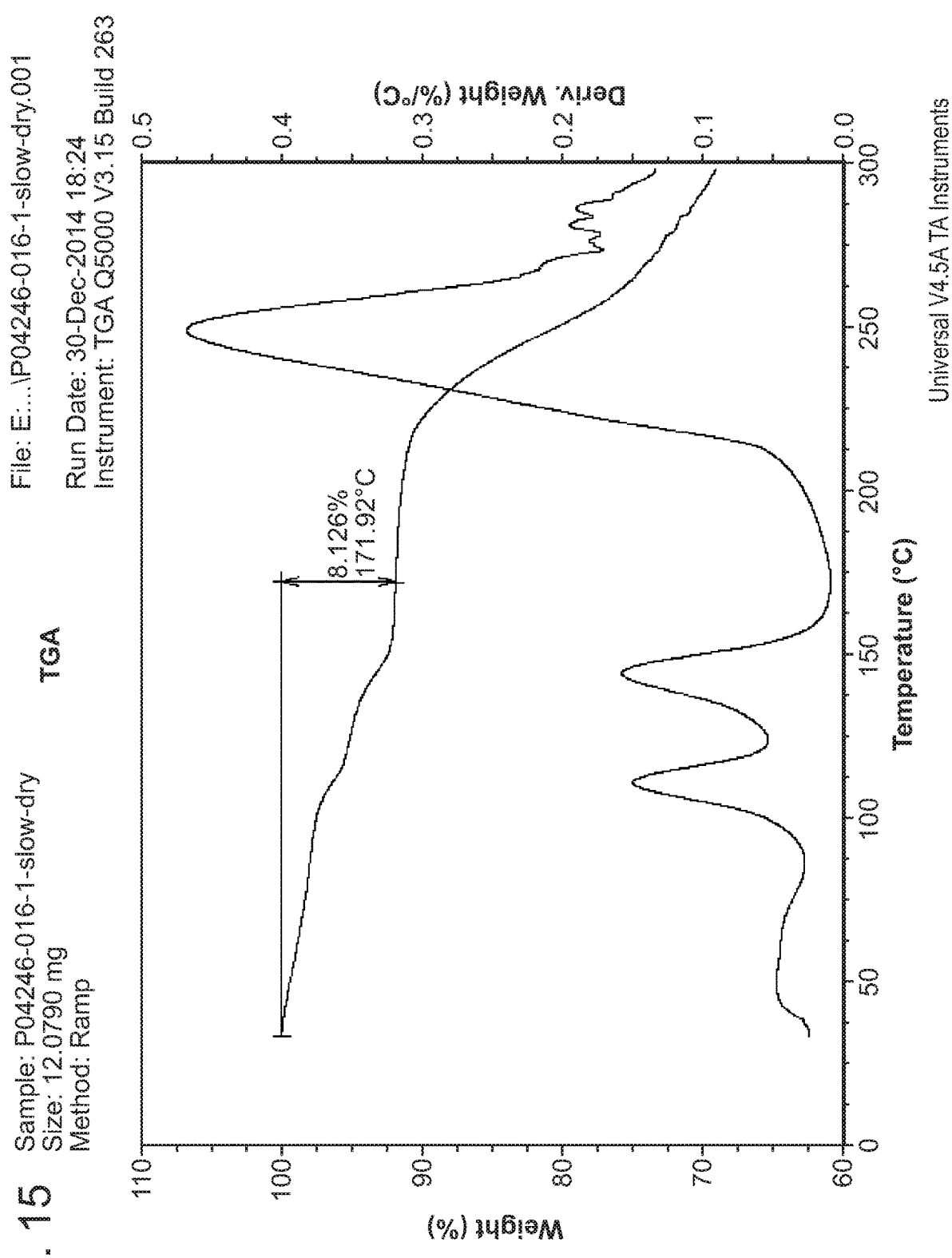
FIG. 15. depicts a thermal gravimetric analysis (TGA) pattern for Form D of Compound 1.

In one aspect, crystalline Form D of Compound 1 is characterized by at least three, at least four, or at least five x-ray powder diffraction peaks at 2Θ angles selected from 14.24°, 15.24°, 15.90°, 18.54°, 18.82°, and 22.46°. Alternatively, crystalline Form D of Compound 1 is characterized by x-ray powder diffraction peaks at 2Θ angles 14.24°, 15.24°, 15.90°, 18.54°, 18.82°, and 22.46°. In another alternative, crystalline Form D of Compound 1 is characterized by at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least twenty-one, at least twenty-two, at least twenty-three, at least twenty-four, at least twenty-five, at least twenty-six, at least twenty-seven, at least twenty-eight, at least twenty-nine, at least thirty, at least thirty-one, at least thirty-two, at least thirty-three, at least thirty-four, at least thirty-five, or at least thirty-six x-ray powder diffraction peaks at 2Θ angles selected from Table 12. In another alternative, crystalline Form D of compound 1 is characterized by x-ray powder diffraction peaks at 7.58°, 9.02°, 14.56°, 14.24°, 15.24°, 15.90°, 17.16°, 18.54°, 18.82°, 20.14°, and 22.46°. In another alternative, crystalline Form D of compound 1 is characterized by x-ray powder diffraction peaks at 7.58°, 9.02°, 14.56°, 14.24°, 15.24°, 15.90°, 17.16°, 18.54°, 18.82°, 20.14°, 22.46°, 20.70°, 21.02°, 21.70°, 24.36°, and 24.58°. In another alternative, crystalline Form D of compound 1 is characterized by x-ray powder diffraction peaks at 7.58°, 9.02°, 14.56°, 14.24°, 15.24°, 15.90°, 17.16°, 18.54°, 18.82°, 20.14°, 22.46°, 20.70°, 21.02°, 21.70°, 24.36°, 24.58°, 25.66°, 25.82°, 26.51°, 26.82°, 29.68°, and 33.70°. In another alternative, crystalline Form D of Compound 1 is characterized by x-ray powder diffraction peaks in Table 12. In another aspect, crystalline Form D of Compound 1 has an XRPD pattern that is substantially the same XRPD pattern shown in FIG. 13. In another aspect, crystalline Form D of Compound 1 has a DSC pattern that is substantially the same DSC pattern shown in FIG. 14. In another aspect, crystalline Form D of Compound 1 has a TGA pattern that is substantially the same TGA pattern shown in FIG. 15. In one aspect, the crystalline Form D of Compound 1 is a bis-hydrogen bromide salt having one or more of the XRPD peaks defined above. In one aspect, Form D of Compound 1 is a hydrate (e.g., a dihydrate) having one or more of the XRPD peaks defined above. In another aspect, Form D of Compound 1 is a bis-hydrogen bromide salt that is a dihydrate and has one or more of the XRPD peaks defined above.

Figure 17:
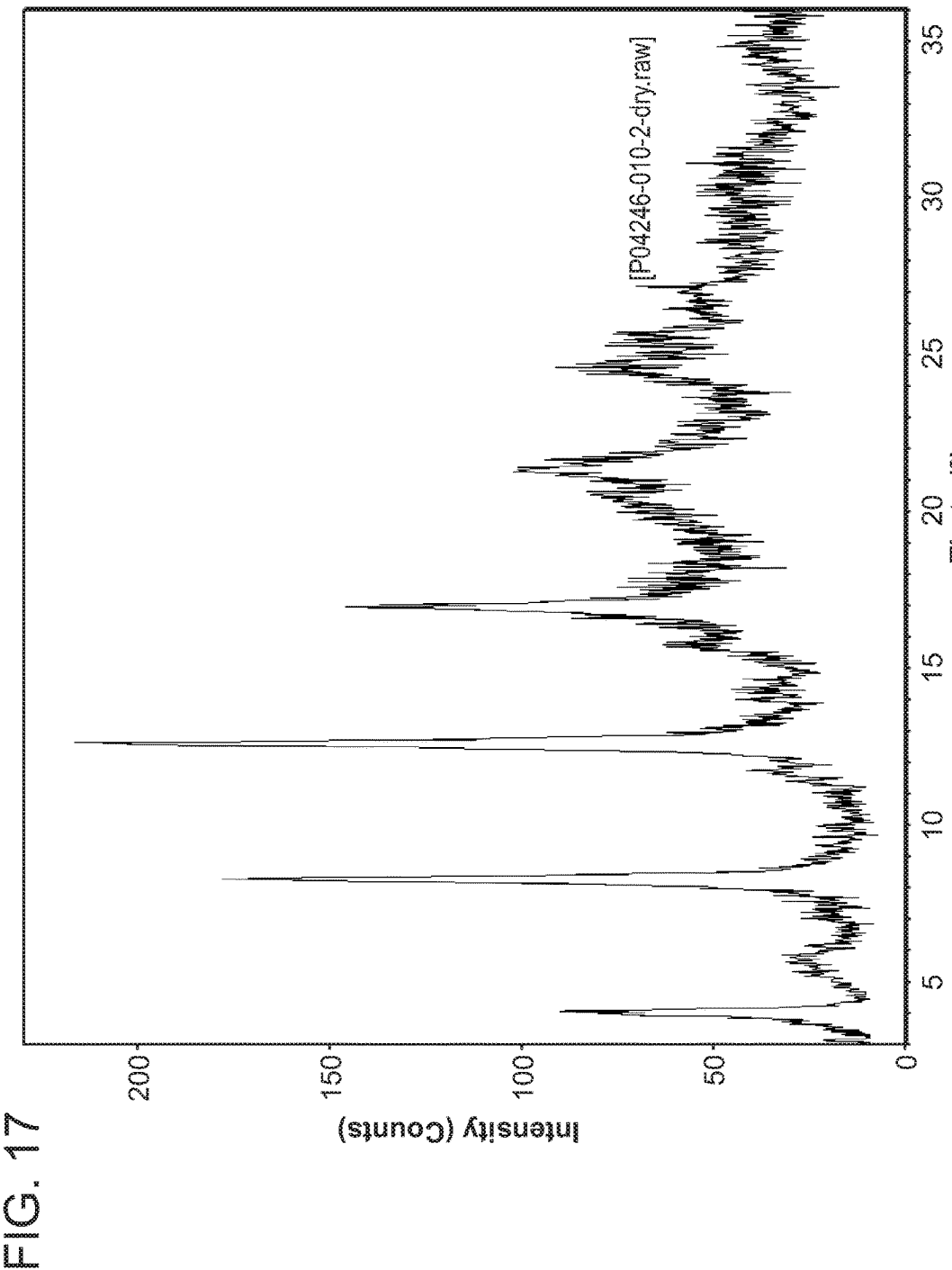
FIG. 17. depicts an X-ray powder diffraction pattern (XRPD) for Form E of Compound 1.
Figure 18:
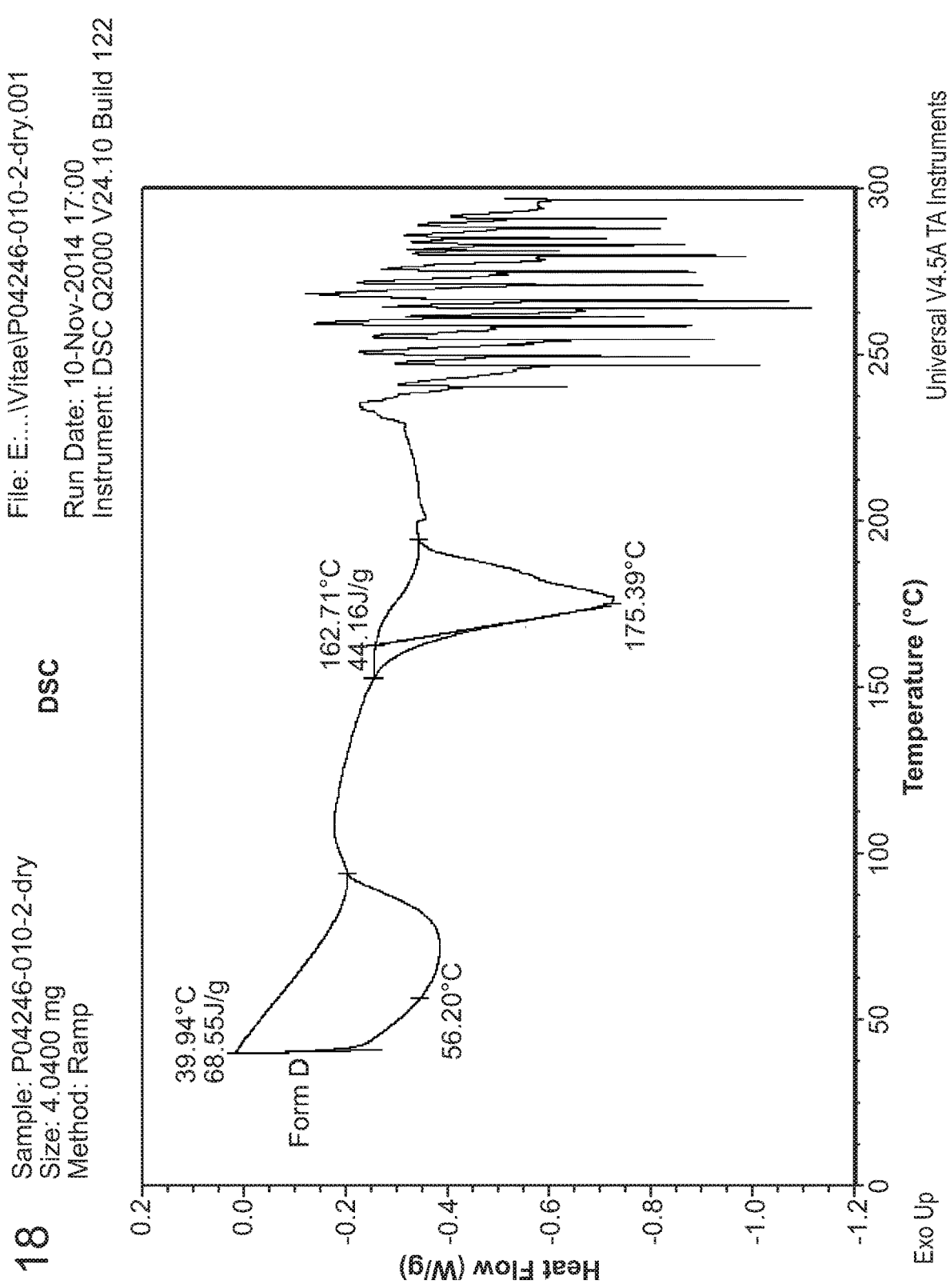
FIG. 18. depicts a Differential Scanning calorimetry (DSC) spectrum for Form E of Compound 1.
Figure 19:
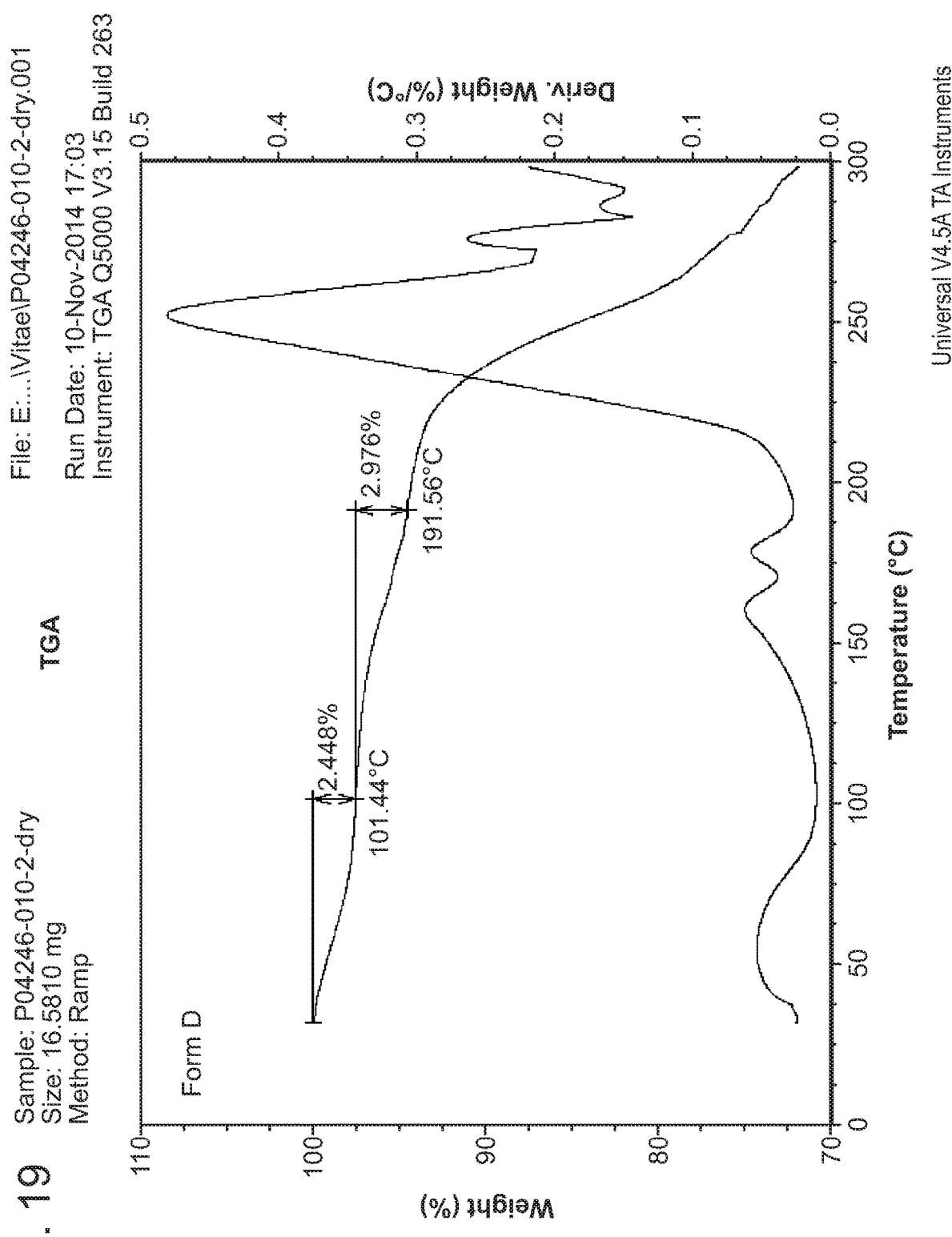
FIG. 19. depicts a thermal gravimetric analysis (TGA) pattern for Form E of Compound 1.

In one aspect, crystalline Form E of Compound 1 is characterized by at least three, at least four, or at least five x-ray powder diffraction peaks at 2Θ angles selected from 4.1°, 8.3°, 12.70°, 16.64°, 16.98°, and 21.32°. Alternatively, crystalline Form E of Compound 1 is characterized by x-ray powder diffraction peaks at 2Θ angles 4.1°, 8.3°, 12.70°, 16.64°, 16.98°, and 21.32°. In another alternative, crystalline Form E of Compound 1 is characterized by at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least twenty-one, at least twenty-two, at least twenty-three, at least twenty-four, at least twenty-five, at least twenty-six, at least twenty-seven, at least twenty-eight, at least twenty-nine, at least thirty, at least thirty-one, at least thirty-two, at least thirty-three, at least thirty-four, at least thirty-five, or at least thirty-six x-ray powder diffraction peaks at 2Θ angles selected from Table 10. In another alternative, crystalline Form E of Compound 1 is characterized by x-ray powder diffraction peaks in Table 10. In another aspect, crystalline Form E of Compound 1 has an XRPD pattern that is substantially the same XRPD pattern shown in FIG. 17. In another aspect, crystalline Form E of Compound 1 has a DSC pattern that is substantially the same DSC pattern shown in FIG. 18. In another aspect, crystalline Form E of Compound 1 has a TGA pattern that is substantially the same TGA pattern shown in FIG. 19. In one aspect, the crystalline Form E of Compound 1 is a bis-hydrogen bromide salt having one or more of the XRPD peaks defined above.

Figure 20:
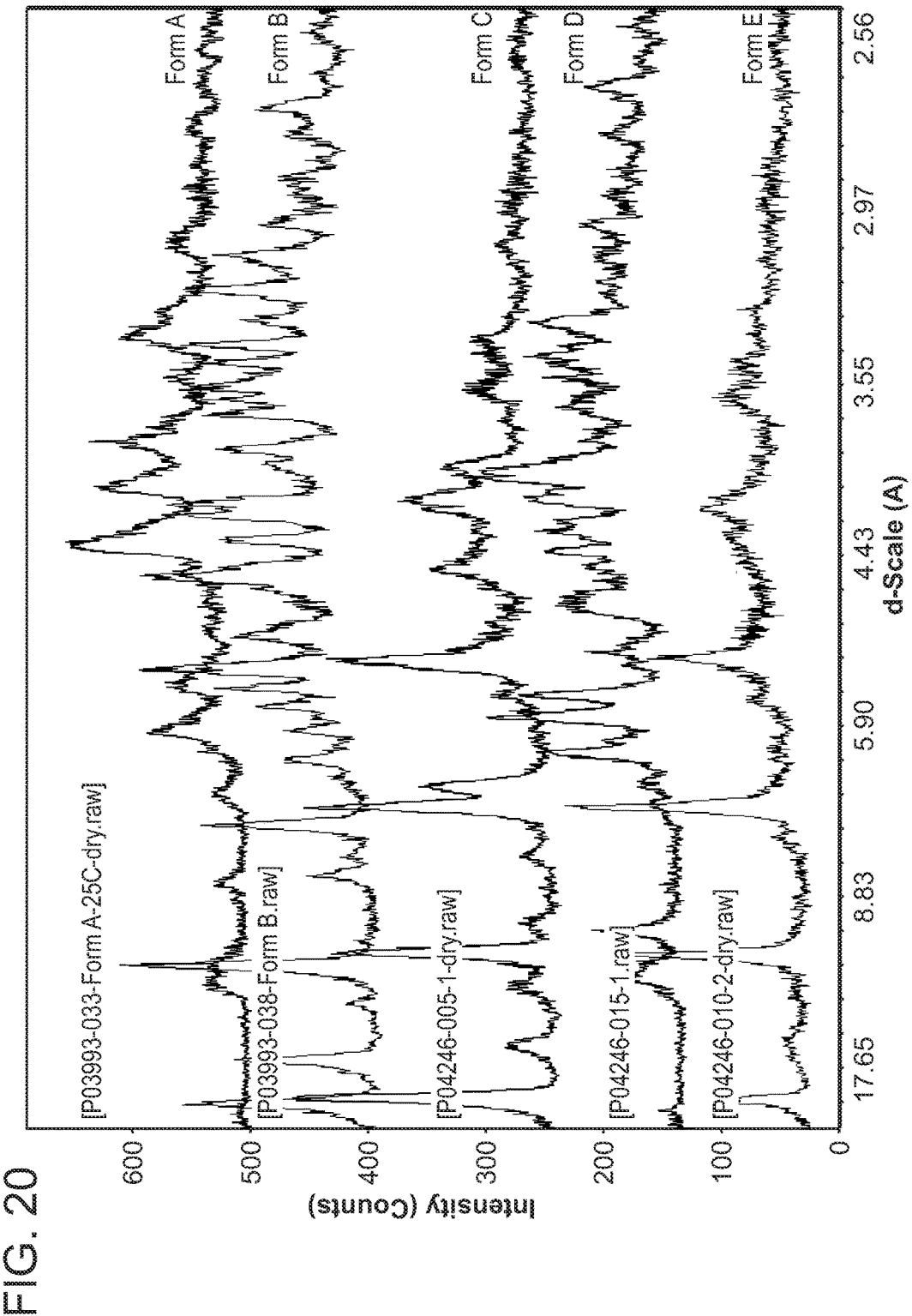
FIG. 20. depicts an X-ray powder diffraction pattern (XRPD) overlay of Form A, Form B, Form C, Form D, and Form E of Compound 1.
Figure 21:
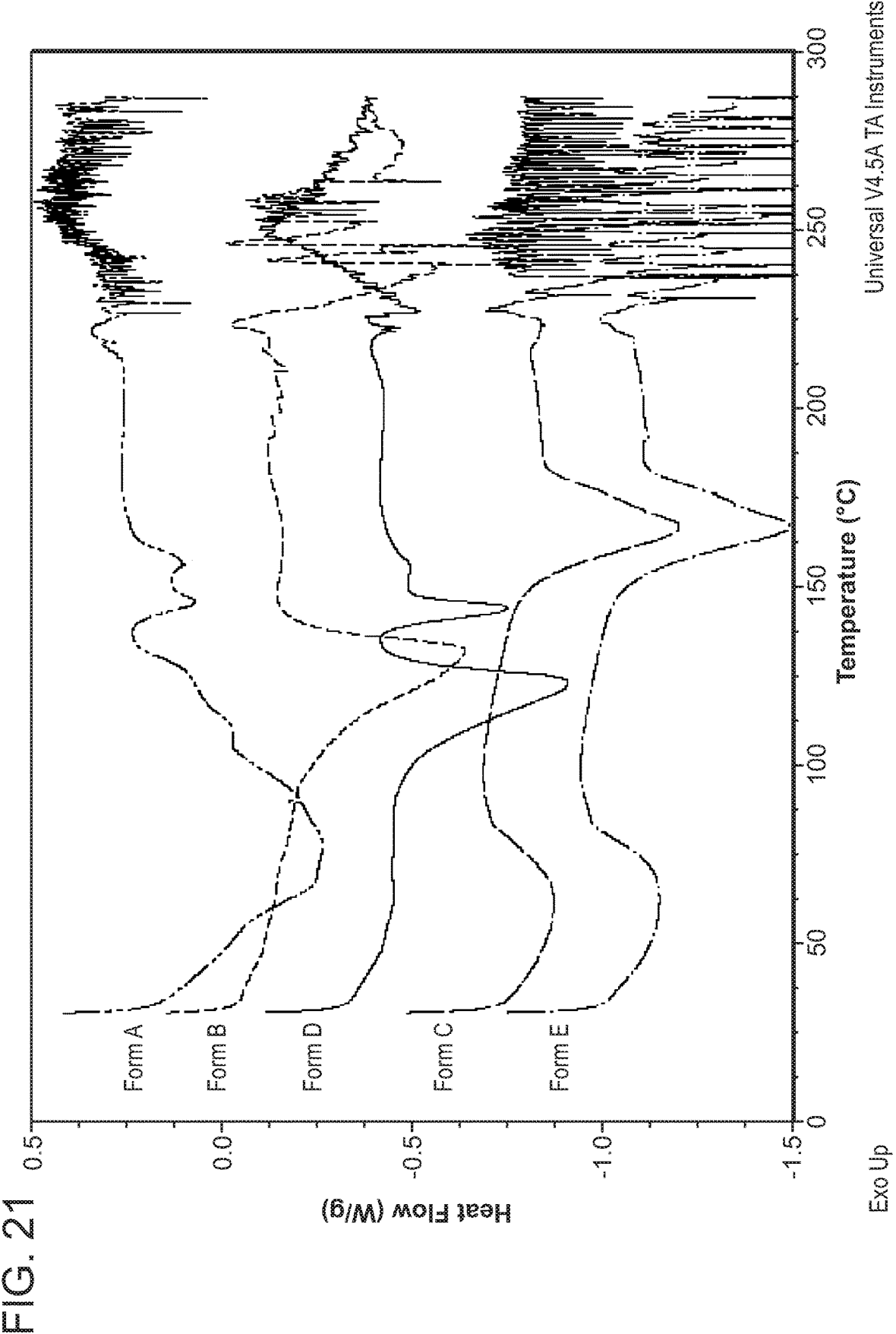
FIG. 21. depicts a Differential Scanning calorimetry (DSC) spectrum overlay of Form A, Form B, Form C, Form D, and Form E of Compound 1.
Figure 22:
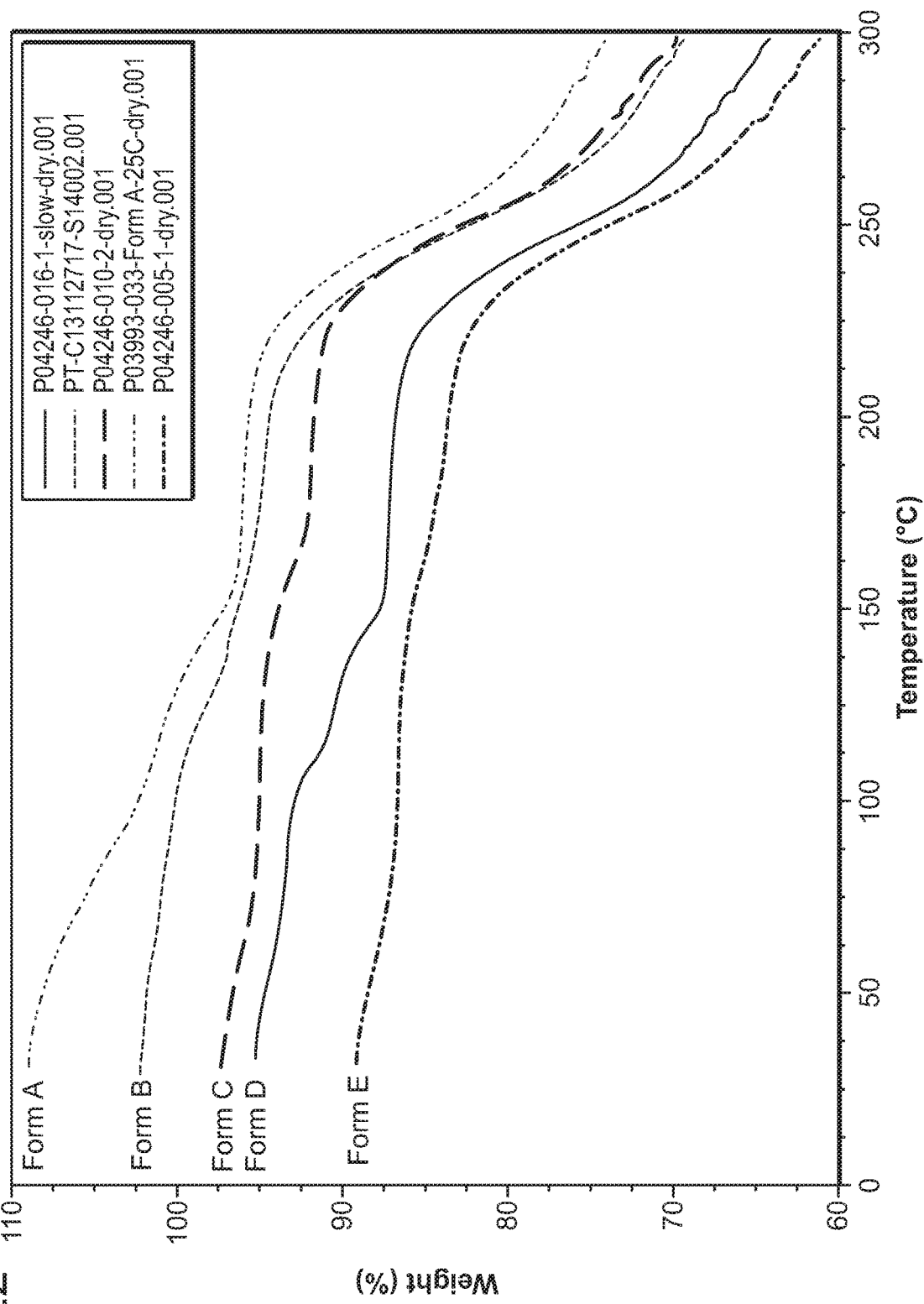
FIG. 22. depicts a thermal gravimetric analysis (TGA) pattern overlay of Form A, Form B, Form C, Form D, and Form E of Compound 1.

For ease of comparison, XRPD, DSC, and TGA overlays of the polymorphic forms are shown in FIGS. 20-22.

In one aspect, crystalline Form A, C, D, or E may each independently be a solvate such as e.g., solvated with water (i.e., a hydrate).

3. Uses, Formulation and Administration

In one aspect, provided are methods of treating a subject (e.g., a human) with a disease or disorder mediated by RORγ using one of more of the disclosed forms of Compound 1; or a composition comprising one of more of the disclosed forms of Compound 1 and a pharmaceutically acceptable carrier. In one aspect, the amount of a disclosed form is such that it is effective as an inverse agonist or antagonist to RORγ in a biological sample or in a subject. In certain aspects, a provided composition is formulated for administration to a subject in need of such composition. In some aspects, a provided composition is formulated for oral administration to a subject.

Compositions described herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

A specific dosage and treatment regimen for any particular subject will depend upon a variety of factors, including age, body weight, general health, sex, diet, time of administration, rate of excretion, drug combination, the judgment of the treating physician, and the severity of the particular disease being treated. The amount of a provided compound in the composition will also depend upon the particular compound in the composition.

Diseases and disorders treatable using one of more of the disclosed forms of Compound 1 include, but are not limited to, inflammatory, metabolic and autoimmune conditions mediated by RORγ. These conditions include, for example, asthma, chronic obstructive pulmonary disease (COPD), bronchitis, allergic rhinitis, atopic dermatitis, contact dermatitis, acne, cystic fibrosis, allograft rejection, multiple sclerosis, scleroderma, arthritis, rheumatoid arthritis, juvenile rheumatoid arthritis, osteoarthritis, ankylosing spondylitis, systemic lupus erythematosus (SLE), psoriasis, Hashimoto's disease, pancreatitis, autoimmune diabetes, type I diabetes, autoimmune ocular disease, ulcerative colitis, Crohn's disease, regional enteritis, inflammatory bowel disease (IBD), inflammatory bowel syndrome (IBS), Sjögren's syndrome, optic neuritis, obesity, hepatosteatosis, adipose tissue-associated inflammation, insulin resistance, type II diabetes, neuromyelitis optica, myasthenia gravis, age related macular degeneration, dry eye, uveitis, Guillain-Barrésyndrome, psoriasis, psoriatic arthritis (PsA), steroid resistant asthma, Graves' disease, scleritis, endometriosis, obstructive sleep apnea syndrome (OSAS), Behçet's disease, dermatomyositis, polymyocitis, graft versus host disease, primary biliary cirrhosis, liver fibrosis, non-alcoholic fatty liver disease (NAFLD), sarcoidosis, primary sclerosing cholangitis, autoimmune thyroid disease, autoimmune polyendocrine syndrome type I, autoimmune polyendocrine syndrome type II, celiac disease, neuromyelitis, juvenile idiopathic arthritis, systemic sclerosis, myocardial infarction, pulmonary hypertension, osteoarthritis, cutaneous leishmaniasis, sinonasal polyposis, and cancer, including but not limited to lung cancer, gastric cancer, breast cancer and colon cancer.

Also included are conditions which are implicated by the regulation of the circadian rhythm of individuals and include, e.g., major depression, seasonal affective disorder, post-traumatic stress disorder (PTSD), bipolar disorder, autism, epilepsy, Alzheimer's disease and other central nervous system (CNS) disorders associated with altered sleep and/or circadian rhythms.

In one aspect, the diseases and disorders treated by a disclosed form of Compound 1 include, e.g., asthma, atopic dermatitis, acne, Crohn's disease, regional enteritis, ulcerative colitis, Sjögren's syndrome, uveitis, Behçet's disease, dermatomyositis, multiple sclerosis, ankylosing spondylitis, systemic lupus erythematosus (SLE), scleroderma, psoriasis, psoriatic arthritis (PsA), steroid resistant asthma and rheumatoid arthritis in the patient.

In one aspect, a human subject is treated with a disclosed form of Compound 1, wherein said form is present in an amount to treat one or more of the diseases and disorders recited above.

In one aspect, a human subject is treated with a composition comprising a disclosed form of Compound 1, wherein said form is present in an amount to treat one or more of the diseases and disorders recited above.

In one aspect, the use of a disclosed form of Compound 1 for the manufacture of a medicament for treating one or more of the diseases and disorders recited above is provided.

In one aspect, a disclosed form of Compound 1 for use in treating one or more of the diseases and disorders recited above is provided.

The amount of provided form of Compound 1 form that may be combined with carrier materials to produce dosage form will vary depending upon the patient to be treated and the particular mode of administration. Provided compositions may be formulated such that a dosage of between 0.001-100 mg/kg body weight/day of the inhibitor can be administered to a patient receiving these compositions.

A specific dosage and treatment regimen for any particular patient will depend upon a variety of factors, including age, body weight, general health, sex, diet, time of administration, rate of excretion, drug combination, the judgment of the treating physician, and the severity of the particular disease being treated.

4. General Preparation Methods

Provided herein are processes for preparing mono- and bis-hydrogen bromide salts of Compound 1. Starting materials and synthetic methods for preparing Compound 1 and precursor materials can be found in e.g., General Procedure B of U.S. Pat. No. 9,266,886, the contents of which are incorporated herein by reference.

A. Two Step Method

A two-step process was initially developed to form the bis-hydrogen bromide salt of Compound 1. See e.g., Scheme 5 in the Exemplification section, a portion of which is depicted here as Scheme 1. This process comprised first forming and isolating a mono-hydrogen bromide salt of Compound 1 followed by conversion of the mono-hydrogen bromide salt to the bis-hydrogen bromide salt of Compound 1.

Scheme 1

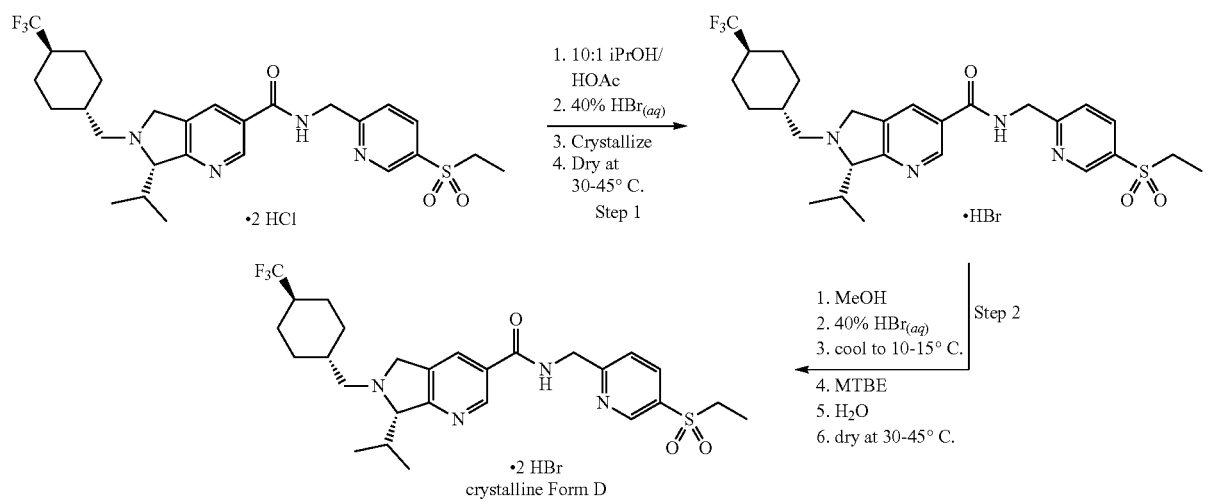

Provided herein, therefore are methods of forming a mono-hydrogen bromide salt of Compound 1, comprising the steps of i) reductively aminating an aldehyde compound represented by the following structural formula:

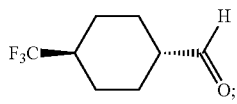

with an amine compound represented by the following structural formula:

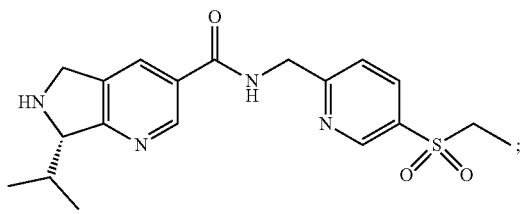 [SMILES: CCS(=O)(=O)c1ccc(CNC(=O)c2cnc3c(c2)CN[C@H]3C(C)C)nc1]

wherein the reductive amination is carried out in the presence of an imine reducing agent to form Compound 1; ii) adding after the formation of Compound 1, sufficient hydrobromic acid to form the mono-hydrogen bromide salt of Compound 1 having the formula:

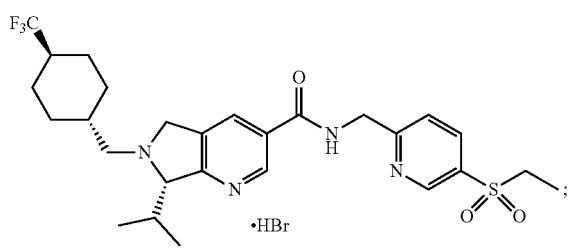

and iii) isolating the mono-hydrogen bromide salt of Compound 1. In some instances, the mono-hydrogen bromide salt of Compound 1 is amorphous. In one aspect, in step ii) Compound 1 is dissolved in a mixture of isopropanol and acetic acid prior to the addition of hydrobromic acid. In another aspect, in step ii) the mono-hydrogen bromide salt of Compound 1 is precipitated via the addition of hydrobromic acid. In one aspect, the amine compound is formed in situ from treating an acid salt form (e.g., a hydrochloric acid salt such as a di-hydrochloric acid salt) of the amine with a tertiary amine base (e.g., trimethylamine or diisopropylethylamine). In one aspect, the above method further comprises the step of iv) dissolving the isolated mono-hydrogen bromide salt of Compound 1 in solvent (e.g., in MeOH) and adding to the solution MTBE and a sufficient amount of hydrobromic acid to form crystalline Form D bis-hydrogen bromide salt of Compound 1 having the formula:

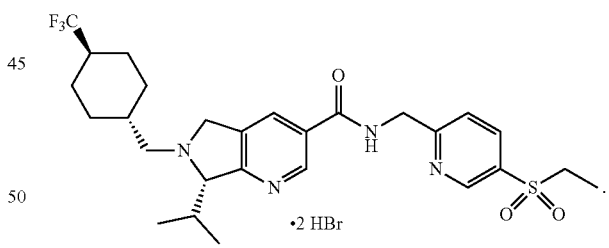

In one aspect, the solution is step iv) is seeded. In one aspect, crystalline Form D bis-hydrogen bromide salt of Compound 1 precipitates from the solution is step iv) upon cooling (e.g., to 5° C. in 30 min/5 to 6 hrs) and is filtered.

Reducing agents for performing reductive aminations are known and include, but are not limited to, sodium triacetoxyborohydride ($NaBH(OAc)_3$), sodium borohydride ($NaBH_4$), palladium on carbon with $H_2$, and platinum on carbon with $H_2$. See e.g., March's Advanced Organic Chemistry, fifth edition, John Wiley & Sons 2001. In one instance, the reducing agent is $NaBH(OAc)_3$.

The amount and concentration of hydrobromic acid that is sufficient to form the mono- or bis-hydrogen bromide salt can vary. For example, 35% to 55% hydrobromic acid can be used, 37% to 53% hydrobromic acid can be used, or 40% to 48% hydrobromic acid can be used. In one aspect, 40% or 48% hydrobromic acid is used. Amounts of hydrobromic acid can range from 0.8 equivalents to 1.4 equivalents. For example, 0.9 to 1.3 equivalents, 1.0 to 1.3 equivalents, or 1.0 to 1.2 equivalents can be used. In one aspect, 1.0 or 1.2 equivalents of hydrobromic acid is used. In one aspect, 1.2 equivalents of 40% hydrobromic acid is used. In another aspect, 1.0 equivalents of 48% hydrobromic acid is used. These amounts and concentrations apply independently for both the mono- and bis-hydrogen bromide salt formation steps. In one aspect, the concentration and amount of hydrobromic acid that is sufficient to form both the mono- and bis-hydrogen bromide salts of Compound 1 are the same and include e.g., 1.2 equivalents of 40% hydrobromic acid or 1.0 equivalents of 48% hydrobromic acid is use for both steps. In one aspect, the hydrobromic acid is a mixture of hydrogen bromide in acetic acid or aqueous hydrobromic acid.

While this process initially proved useful in forming the desired product, the combination of HBr and MeOH resulted in product contamination, i.e., excess methyl bromide was present in the initially isolated product. It was not until after significant efforts, that slurrying the product in a mixture of isopropyl acetate and water was found to effectively remove the excess methyl bromide. Although a mixture of heptane and water was also found to be effective, the solubility of the bis-hydrogen bromide crystalline Form D salt was greater in the isopropyl acetate/water mixture, and therefore this mixture was chosen for scale up purposes. A schematic representation of this process is shown below as Scheme 2.

In one aspect, removing methyl bromide from a composition comprising methyl bromide and a bis-hydrogen bromide salt of Compound 1 comprises slurrying the composition in a mixture of isopropyl acetate comprising 0.25% to 2.5% v/v of water; and ii) separating the bis-hydrogen bromide salt of the compound from the mixture of isopropyl acetate/water. In one aspect, the mixture comprises isopropyl acetate comprising 0.5% to 2.0% v/v of water, 0.7% to 1.7% v/v of water, 0.8% to 1.5% v/v of water, 0.9% to 1.3% v/v of water, 0.9% to 1.1% v/v of water, 0.5%, 0.6%, 0.7%, 0.8%, 0.9%, 1.0%, 1.1%, 1.2%, 1.3%, 1.4%, or 1.5%.

In some aspects, prior to slurrying the composition, the methyl bromide present in the composition is greater than 45 ppm, greater than 50 ppm, greater than 55 ppm, or greater than 60 ppm. For example, the amount of methyl bromide present in the composition may be from 50 ppm to 1000 ppm. The amounts of methyl bromide present in the composition prior to slurrying refers to the amount present in a dried composition, e.g., prior to slurrying the composition is dried (e.g., at approximately 15 to 50° C. such as 20 to 25° C.) under approximately –0.096 MPa vacuum for 20 hours or more. In a further aspect, prior to slurrying the composition, the methyl bromide present in the composition is greater than 45 ppm, greater than 50 ppm, greater than 55 ppm, greater than 60 ppm, or from 50 ppm to 1000 ppm; and the mixture comprises isopropyl acetate comprising 0.5% to 2.0% v/v of water, 0.7% to 1.7% v/v of water, 0.8% to 1.5% v/v of water, 0.9% to 1.3% v/v of water, 0.9% to 1.1% v/v of water, 0.5%, 0.6%, 0.7%, 0.8%, 0.9%, 1.0%, 1.1%, 1.2%, 1.3%, 1.4%, or 1.5%.

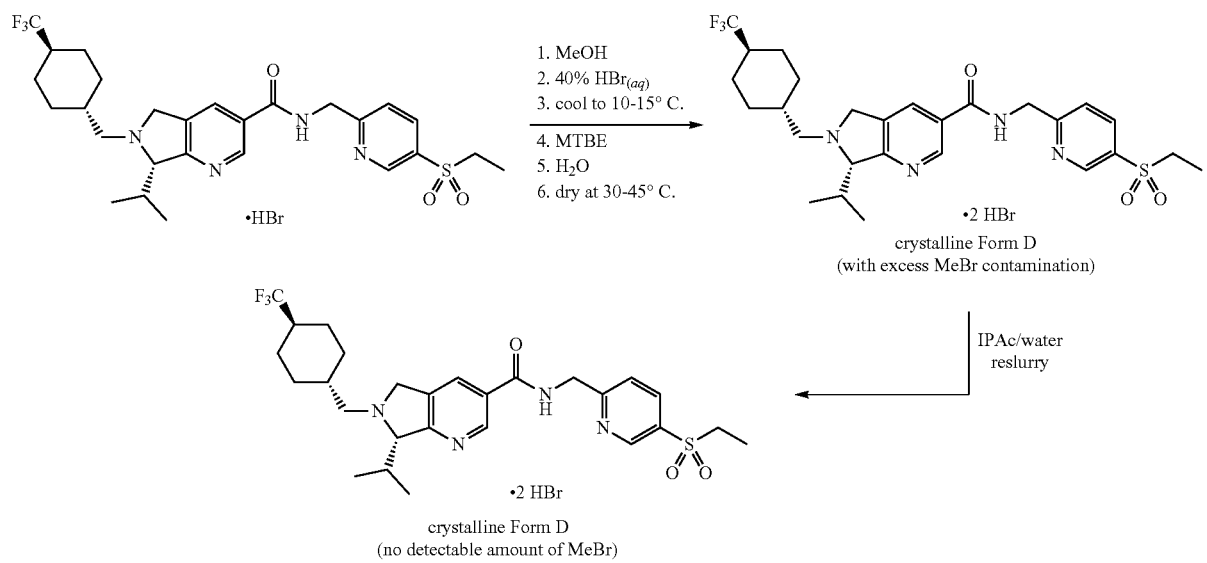

Scheme 2

Provided herein, therefore is a method of removing methyl bromide from a composition comprising methyl bromide and a bis-hydrogen bromide salt of Compound 1 (e.g., crystalline Form D of the bis-hydrogen bromide salt of Compound 1) comprising i) slurrying the composition in a mixture of isopropyl acetate/water or a mixture of heptane/water; and ii) separating the bis-hydrogen bromide salt of the compound from the mixture of isopropyl acetate/water or the mixture of heptane/water.

In some aspects, separating the crystalline form D bis-hydrogen bromide salt from the mixture results in a crystalline form D bis-hydrogen bromide salt having less than 45 ppm of methyl bromide present. For example, in certain instances, separating the crystalline form D bis-hydrogen bromide salt from the mixture results in a crystalline form D bis-hydrogen bromide salt having is less than 40 ppm, less than 30 ppm, less than 20 ppm, less than 10 ppm, less than 5 ppm, or less than 1 ppm of methyl bromide present. In one aspect, separating the crystalline form D bis-hydrogen bromide salt from the mixture results in a crystalline form D bis-hydrogen bromide salt having an amount of methyl bromide present that is below the level of detection.

In some aspects, separating the crystalline form D bis-hydrogen bromide salt from the mixture results in a crystalline form D bis-hydrogen bromide salt having less than 45 ppm, less than 40 ppm, less than 30 ppm, less than 20 ppm, less than 10 ppm, less than 5 ppm, or less than 1 ppm of methyl bromide present, or an amount of methyl bromide that is below the level of detection; and wherein prior to slurrying the composition, the methyl bromide present in the composition is greater than 45 ppm, greater than 50 ppm, greater than 55 ppm, greater than 60 ppm, or from 50 ppm to 1000 ppm. In some aspects, separating the crystalline form D bis-hydrogen bromide salt from the mixture results in a crystalline form D bis-hydrogen bromide salt having less than 45 ppm, less than 40 ppm, less than 30 ppm, less than 20 ppm, less than 10 ppm, less than 5 ppm, or less than 1 ppm of methyl bromide present, or an amount of methyl bromide that is below the level of detection; wherein prior to slurrying the composition, the methyl bromide present in the composition is greater than 45 ppm, greater than 50 ppm, greater than 55 ppm, greater than 60 ppm, or from 50 ppm to 1000 ppm; and wherein the mixture comprises isopropyl acetate comprising 0.5% to 2.0% v/v of water, 0.7% to 1.7% v/v of water, 0.8% to 1.5% v/v of water, 0.9% to 1.3% v/v of water, 0.9% to 1.1% v/v of water, 0.5%, 0.6%, 0.7%, 0.8%, 0.9%, 1.0%, 1.1%, 1.2%, 1.3%, 1.4%, or 1.5%.

Further detailed procedures on this two-step method are provided in the Exemplification section below.

B. One Step Method

A one-step method for preparing bis-hydrogen bromide salt of Compound 1 was also identified. In this instance, it was found that switching the solvent from $CH_2Cl_2$ to EtOH in the reductive amination reaction followed by neutralizing the reductive amination mixture, and precipitating the resulting free base afforded a highly purified free-base product, or at least in pure enough form such that it could be directly converted to the bis-hydrogen bromide salt without the separate step of isolating the mono-hydrogen bromide salt. This method is depicted in Scheme 6 below, a portion of which is represented here as Scheme 3.

Scheme 3

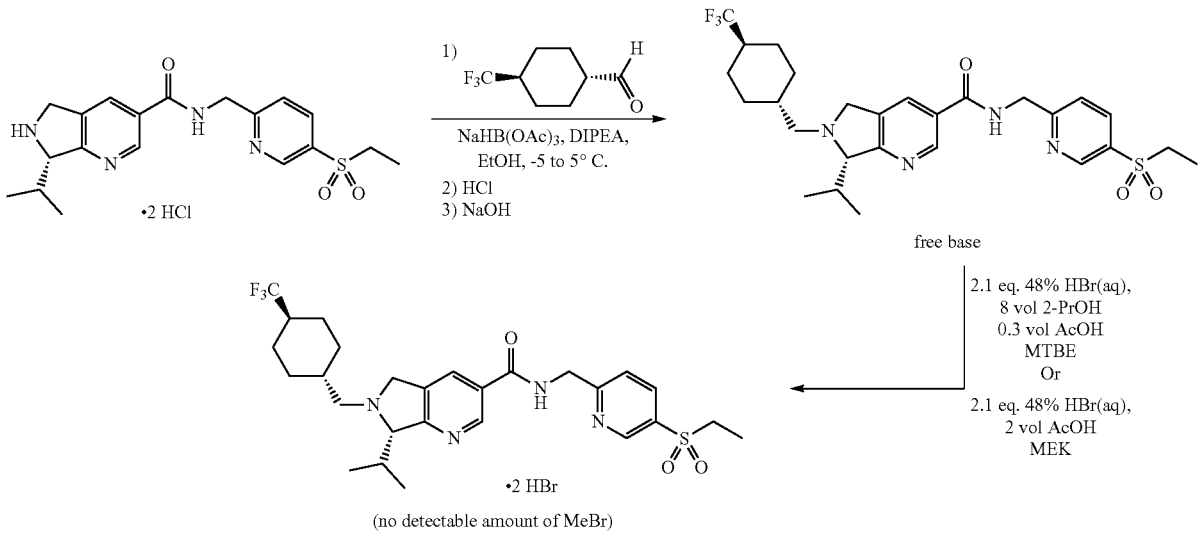

Thus, in one aspect, provided herein are alternative methods for preparing a free base form of Compound 1, the method comprising i) reductively aminating an aldehyde compound represented by the following structural formula:

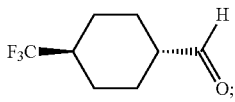

with an amine compound represented by the following structural formula:

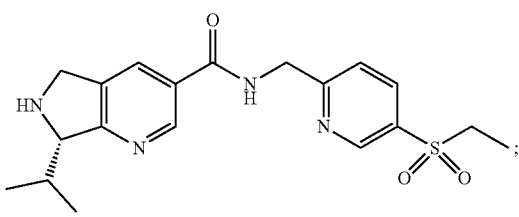 [SMILES: CCS(=O)(=O)c1ccc(CNC(=O)c2cnc3c(c2)CN[C@H]3C(C)C)nc1]

wherein the reductive amination is carried out in the presence of ethanol, and in the presence of an imine reducing agent; ii) quenching the reductive amination mixture with acid; iii) neutralizing the resulting solution with base, thereby precipitating the free base form of the compound; and iv) isolating the precipitated free-based form of the compound from the solution. In one aspect, a solution of the aldehyde compound in isopropyl acetate is added to a slurry of the imine reducing agent in a solution of the trialkyl amine and the amine compound in ethanol. In one aspect, the acid used for quenching is hydrochloric acid. In one aspect, the base used is an aqueous base such as a solution of aqueous sodium hydroxide. In one aspect, the solution is neutralized in step iii) to pH 5 to 7. In one aspect, the amine compound is formed in situ from treating an acid salt form (e.g., a hydrochloric acid salt such as a di-hydrochloric acid salt) of the amine with a tertiary amine base.

Again, tertiary amines for performing reductive aminations are known and include, but are not limited to, trialkylamines such as diisopropylethylamine (DIPEA or iPr$_2$NEt) and trimethylamine (TEA). See e.g., March's Advanced Organic Chemistry, fifth edition, John Wiley & Sons 2001. In one instance, the amine used is DIPEA.

Again, reducing agents for performing reductive aminations are known and include, but are not limited to, sodium triacetoxyborohydride (NaBH(OAc)$_3$), sodium borohydride (NaBH$_4$), palladium on carbon with H$_2$, and platinum on carbon with H$_2$. See e.g., March's Advanced Organic Chemistry, fifth edition, John Wiley & Sons 2001. In one instance, the reducing agent is NaBH(OAc)$_3$.

From the free-base, the bis-hydrogen bromide salt can then be prepared directly (i.e., without first isolating the mono-hydrogen bromide salt) by adding sufficient hydrobromic acid to the free-base to form the bis-hydrogen bromide salt. In one aspect, formation of the bis-hydrogen bromide salt from the free-based further comprises the addition of a mixture of isopropanol, MTBE, and acetic acid. In another aspect, formation of the bis-hydrogen bromide salt from the free-based further comprises the addition of a mixture of acetic acid and MEK.

Here, the amount and concentration of hydrobromic acid that is sufficient to form the bis-hydrogen bromide salt can vary, but is typically from 2 to 5 equivalents of, for example, 35% to 55% hydrobromic acid, 37% to 53% hydrobromic acid, or 40% to 48% hydrobromic acid. In one aspect, 40% or 48% hydrobromic acid is used. In one aspect, 2 to 4 equivalents, 2 to 3 equivalents, 2 to 2.5 equivalents or 2.1 equivalents of 40% or 48% hydrobromic acid is used.

Although the need to isolate the mono-hydrogen bromide salt first prior to forming the bis-hydrogen bromide salt was eliminated with this one-step method, and contamination of product from methyl bromide was absent because of the avoidance of MeOH, the initial bis-hydrogen bromide salt formed was determined to be existed as a mixture of crystalline Forms E, F, and G. Forms F and G were not characterized further. To overcome this problem, it was found that slurrying the mixture of crystalline forms in isopropyl acetate/water resulted in the formation of single crystalline Form D bis-hydrogen bromide salt. See e.g., Scheme 4 below.

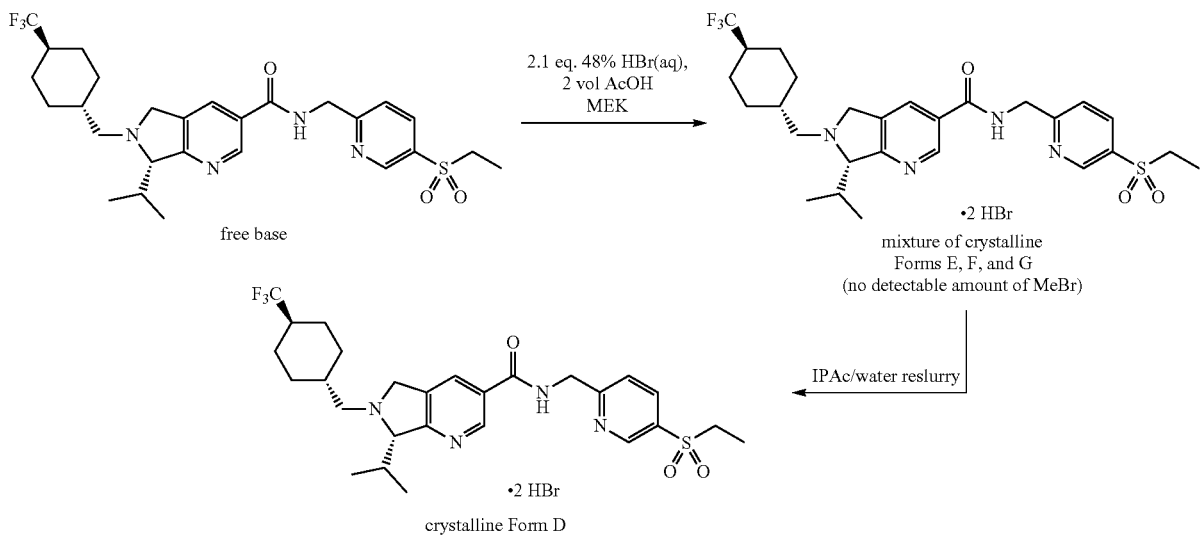

Thus, in one aspect, provided herein is a method of converting crystalline Forms E, F and G of the bis-hydrogen bromide salt of Compound 1 to crystalline Form D bis-hydrogen bromide salt, comprising i) slurrying a composition comprising one or more of crystalline forms E, F and G in a mixture of isopropyl acetate/water containing between 0.25%-2.5% v/v; and ii) separating (e.g., via filtration) the crystalline form D of the bis-hydrogen bromide salt of the compound from the mixture of isopropyl acetate/water.

In one aspect, the mixture comprises isopropyl acetate comprising 0.5% to 2.0% v/v of water, 0.7% to 1.7% v/v of water, 0.8% to 1.5% v/v of water, 0.9% to 1.3% v/v of water, 0.9% to 1.1% v/v of water, 0.5%, 0.6%, 0.7%, 0.8%, 0.9%, 1.0%, 1.1%, 1.2%, 1.3%, 1.4%, or 1.5%.

In one aspect, the amount of Form E, F, and G present in the composition is greater than 90% by weight, such as greater than 91%, greater than 92%, greater than 93%, greater than 94%, greater than 95%, greater than 96%, greater than 97%, or greater than 98%, greater than 99%.

In one aspect, in the methods described herein, when the product formed is crystalline Form D bis-hydrogen bromide salt, that product may be further characterized by the XRPD peaks and data described herein e.g., by at least three, at least four, or at least five x-ray powder diffraction peaks at 2Θ angles selected from 14.24°, 15.24°, 15.90°, 18.54°, 18.82°, and 22.46°; or by x-ray powder diffraction peaks at 2Θ angles 14.24°, 15.24°, 15.90°, 18.54°, 18.82°, and 22.46°; or by at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least twenty-one, at least twenty-two, at least twenty-three, at least twenty-four, at least twenty-five, at least twenty-six, at least twenty-seven, at least twenty-eight, at least twenty-nine, at least thirty, at least thirty-one, at least thirty-two, at least thirty-three, at least thirty-four, at least thirty-five, or at least thirty-six, x-ray powder diffraction peaks at 2Θ angles selected from Table 12; or by x-ray powder diffraction peaks in Table 12.

Similarly, crystalline Forms E, F and G referred to in the methods described herein may be further characterized by the XRPD peaks and data described herein for each of these forms.

Other processes, compounds, and compositions are described below in the Exemplification section and are included herein.

EXEMPLIFICATION

The following non-limiting examples are provided to further illustrate the present disclosure.

Materials/Methods

Differential Scanning Calorimetry (DSC)

DSC was performed using a TA Instruments 2920 differential scanning calorimeter. Temperature calibration was performed using NIST-traceable indium metal. The sample was placed into an aluminum Tzero crimped pan (T0C) and the weight was accurately recorded. A weighed aluminum pan configured as the sample pan was placed on the reference side of the cell. The data acquisition parameters and pan configuration for each thermogram are displayed in the image in the figure. The method code on the thermogram is an abbreviation for the start and end temperature as well as the heating rate; e.g., (−30)-250-10 means "from −30° C. to 250° C., at 10° C./min".

Thermal Gravimetric Analysis (TG)

TG analyses were performed using a TA Instruments Q5000 IR thermogravimetric analyzer. Temperature calibration was performed using nickel and Alumel™. Each sample was placed in a platinum pan. The sample was hermetically sealed, the lid pierced, then inserted into the TG furnace. The furnace was heated under nitrogen. The data acquisition parameters for each thermogram are displayed in the in the figure. The method code on the thermogram is an abbreviation for the start and end temperature as well as the heating rate; e.g., 00-350-10 means "from ambient ° C. to 350° C., at 10° C./min".

X-ray Powder Diffraction (XRPD)

XRPD patterns were collected with a PANalytical X'Pert PRO MPD diffractometer using an incident beam of Cu radiation produced using an Optix long, fine-focus source. An elliptically graded multilayer mirror was used to focus Cu Kα X-rays through the specimen and onto the detector. Prior to the analysis, a silicon specimen (NIST SRM 640e) was analyzed to verify the observed position of the Si 111 peak is consistent with the NIST-certified position. A specimen of the sample was sandwiched between 3-μm-thick films and analyzed in transmission geometry. A beam-stop, short antiscatter extension, antiscatter knife edge were used to minimize the background generated by air. Soller slits for the incident and diffracted beams were used to minimize broadening from axial divergence. Diffraction patterns were collected using a scanning position-sensitive detector (X'Celerator) located 240 mm from the specimen and Data Collector software v. 2.2b. The data acquisition parameters for each pattern are displayed above the image in the Data section of this report including the divergence slit (DS) before the mirror.

Formation and Analysis of Salt Forms

Because Compound 1 is highly susceptible to oxidation, particularly in solution, it was significantly difficult to produce a stable salt form of this compound.

A salt/co-crystal screening was conducted under 127 conditions with 20 salt/co-crystal co-formers and seven solvent systems. For each condition, approximately 20 mg of Compound 1 was dispersed in the selected solvent in a glass vial and then salt/co-crystal co-former was added. Observation of slurries were followed by isolation and analysis of the resulting solids. Even though some crystalline solids were isolated and analyzed by XRPD, discoloration, possibly associated with decomposition was also observed (Table 1). Salt-screening experiments yielding a unique XRPD pattern were analyzed by HPLC-UV and were all determined to be primarily composed of degradants. A re-preparation and scale up of the adipic acid prepared under strictly nitrogen atmosphere still yielded primarily degradants and was not pursued further.

TABLE 1

| Exp # | Acids, molar ratio (API/acid) | A EtOH | B ACN | C Acetone | D THF | E THF/water 3:1 | F THF/water 1:1 | G EtOH/Water 9:1 |
|---|---|---|---|---|---|---|---|---|
| 0 | control | YS | WS | OS | YS | OS | YD | WS |
| 1 | hydrochloric acid (1:1) | YS | RD | RS | RG | OS | YE | YD |
| 2 | hydrochloric acid (2:1) | OS | BS | OS | BG | RG | YE | YD |
| 3 | sulfuric acid (1:1) | YS | YD | RG | OG | OG | YE | YD |
| 4 | sulfuric acid (2:1) | YD | YG | RG | OG | OG | YE | YD |
| 5 | phosphoric acid (1:1) | YS | YG | RD | BG | BG | YE | WS |
| 6 | phosphoric acid (2:1) | YS | OG | RD | OG | BD | YE | YD |
| 7 | $CH_3SO_3H$ (1:1) | YS | YD | YD | YG | YG | NT | YD |
| 8 | toluene sulfonic acid*H2O (1:1) | YS | YD | YD | YG | YG | NT | OD |
| 9 | fumaric acid (1:1) | YS | YS | OS | YS | BG | NT | OD |
| 10 | L-tartaric acid (1:1) | YS | BD | RD | YS | WS | NT | OD |
| 11 | maleic acid (1:1) | RS | RD | BD | BG | BG | NT | OD |
| 12 | adipic acid (1:1) | YS | YS | YS | OS | OD | NT | OD |
| 13 | gentisic acid (1:1) | YD | RD | BD | BG | RD | NT | OD |
| 14 | Glutamic acid | YS | YS | OS | OS | BS | NT | WS |
| 15 | citric acid (1:1) | YS | OD | OD | OG | BD | NT | OD |
| 16 | L-malic acid (1:1) | YS | YD | YS | YS | OS | NT | OD |
| 17 | DL-lactic acid (1:1) | OS | RD | OD | OS | WS | NT | OD |
| 18 | succinic acid (1:1) | YS | YS | WS | YS | OG | NT | OD |
| 19 | benzoic acid (1:1) | YS | YD | OD | OS | OG | NT | OD |
| 20 | L-ascorbic acid (1:1) | YS | OD | BS | OS | BG | NT | OD |

Key
Colors: (W)hite, (Y)ellow, (O)range, (R)ed, B(rown)
Physical Form: (S)olid, (G)el, (D)issolved, (E)mulsion; NT = not tested With the exception of the HBr salt, salt screening was unsuccessful in identifying further options for new forms of Compound 1 because of degradation. While the HCl and sulfate salts, having less degradation than others, did initially prove promising, additional techniques were required to reduce oxidation during their production. For example, solvent systems in which Compound 1 has limited solubility were chosen for formation of the HCl and sulfates salts to limit oxidation, while providing enough solubility to promote conversion to crystalline salts. However, this approach is time consuming and not favorable for large scale manufacturing methods. Also, the counterpart HBr salt was found to not require such approaches as it was stable under oxygen atmosphere and did not degrade during preparation or after air-drying.

Figure 8:
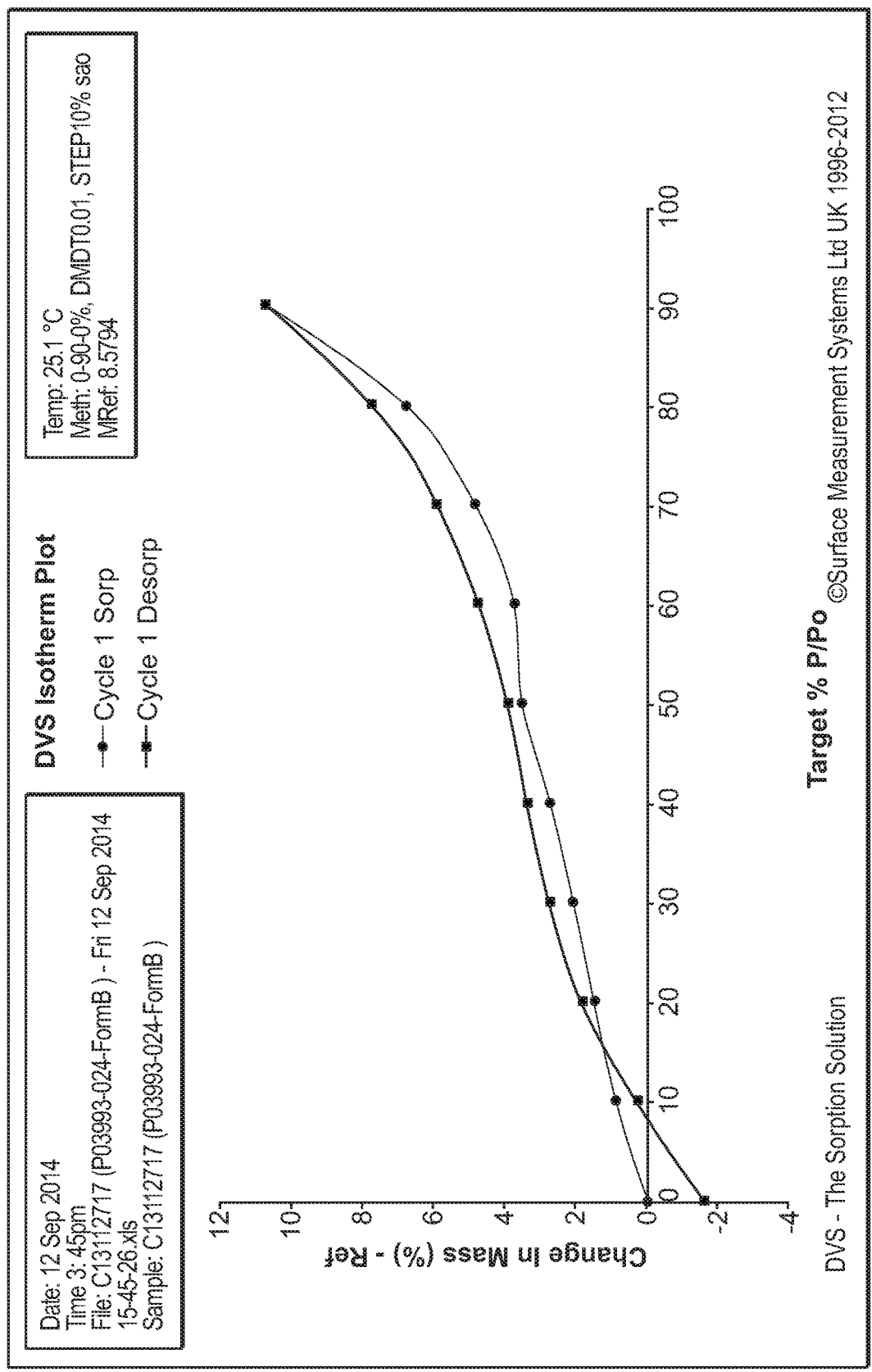
FIG. 8. depicts a Dynamic Vapor Sorption (DVS) isotherm plot for Form B of Compound 1.
Figure 16:
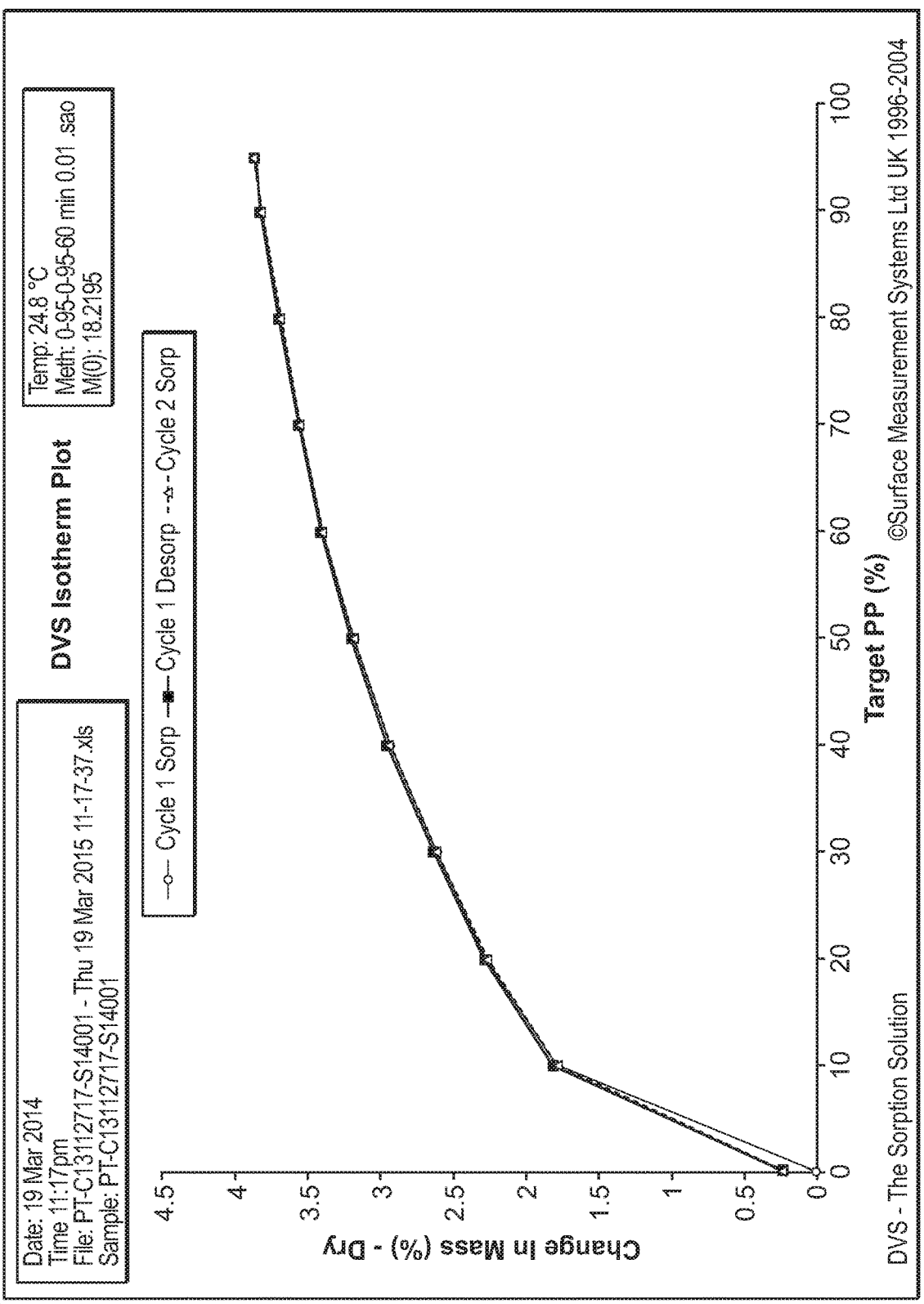
FIG. 16. depicts a Dynamic Vapor Sorption (DVS) isotherm plot for Form D of Compound 1.

During process, and as described in further detail below, both a mono- and bis-hydrogen bromide salt of Compound 1 were prepared. Although both of these forms did not degrade during preparation, the mono-hydrogen bromide salt absorbs about twice the amount of water than the corresponding bis-hydrogen bromide form. See e.g., FIGS. 8 and 16. Indeed, the bis-hydrogen bromide salt exhibits no more than a 5% weight change. This is a significant advantage because higher moisture uptake can lead to diminished shelf life and unwanted conversion to other forms and/or degradation.

Formation and Analysis of Crystalline Forms

Slurry experiments starting with amorphous hydrogen bromide salt of Compound 1 in various solvents with different water activities were conducted. A total of five crystalline hydrogen bromide salt forms (both mono and bis-HBr salts) were found and classified as Form A, Form B, Form C, Form D, and Form E. The summary of each of these five forms is discussed below. Amorphous hydrogen bromide salt of Compound 1 was prepared according to General Procedure B as described for Compound 2 in U.S. Pat. No. 9,266,886, the contents of which are incorporated herein by reference.

Figure 4:
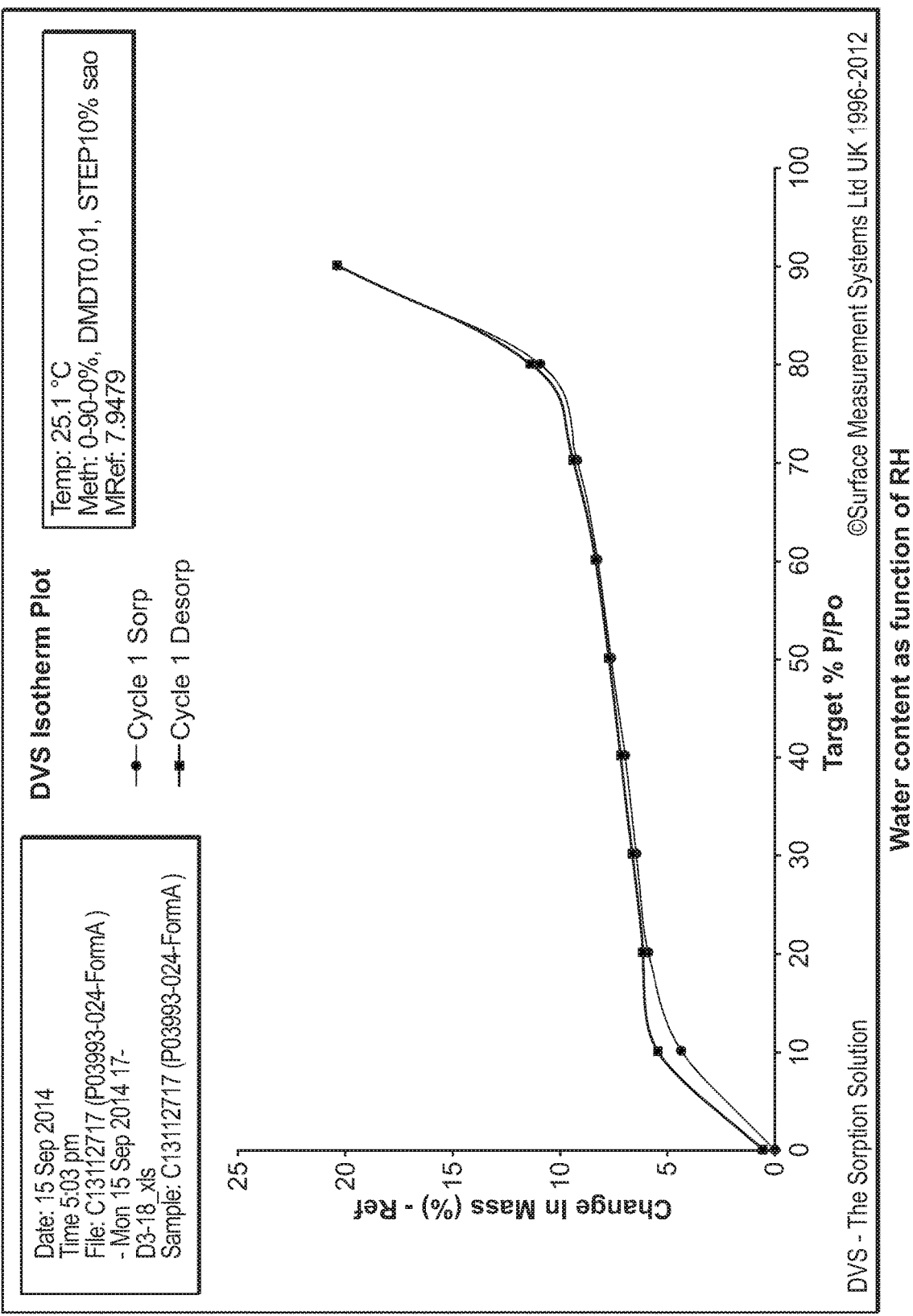
FIG. 4. depicts a Dynamic Vapor Sorption (DVS) isotherm plot for Form A of Compound 1.
Figure 12:
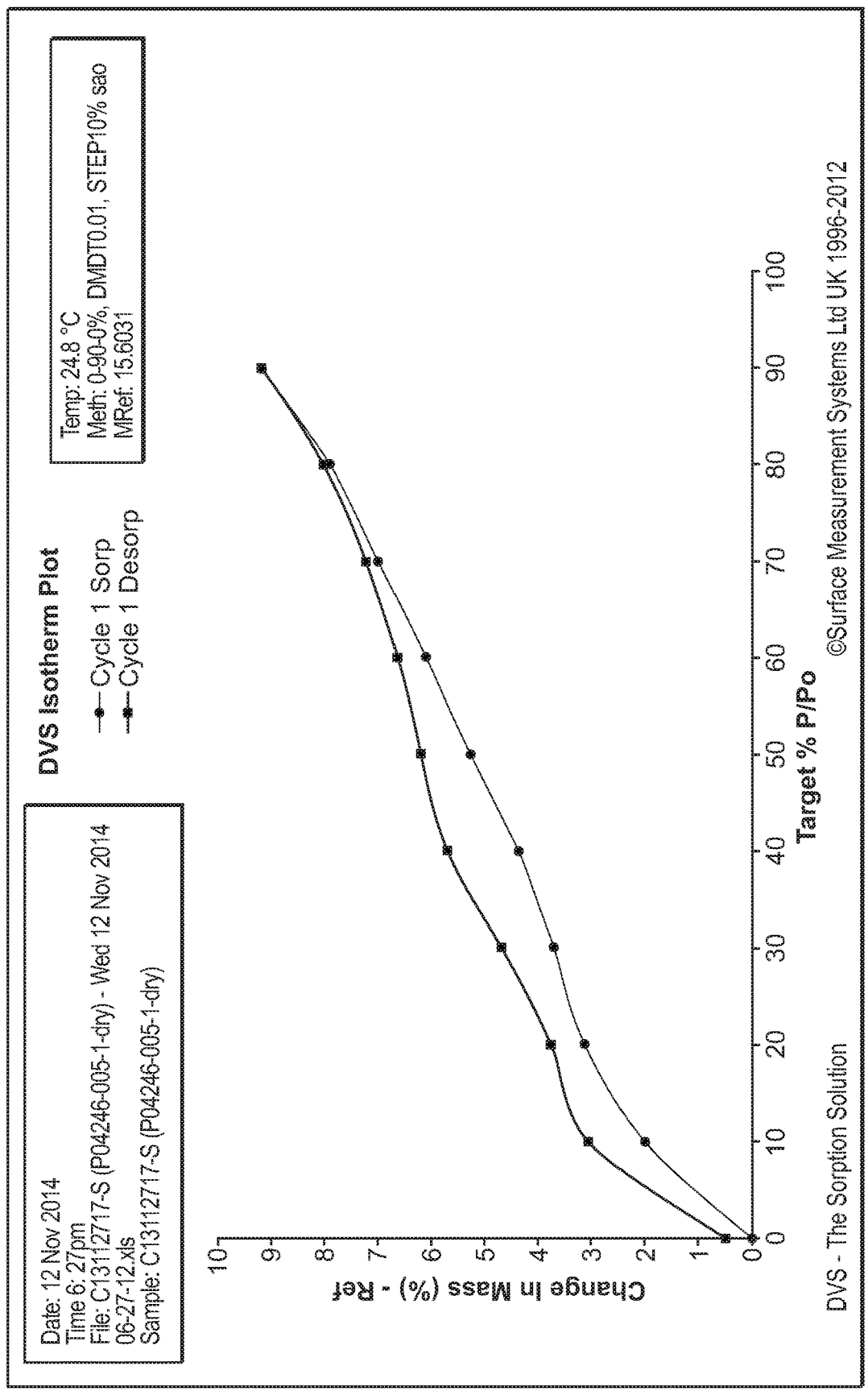
FIG. 12. depicts a Dynamic Vapor Sorption (DVS) isotherm plot for Form C of Compound 1

Out of these forms, the bis-hydrogen salt crystalline Form D of Compound 1 proved to be the most useful, particularly in view of its advantages over the other four forms. First, the moisture uptake of Form D is significantly less than the other forms. Compare e.g., the DVS isotherm plot of Form D (FIG. 16) with Form A (FIG. 4), Form B (FIG. 8), and Form C (FIG. 12).

Next, from a manufacturing perspective, Form D was found to be reproducible at large scale. For example, during preparation of Form A, the initial material produced was an oil. While this eventually converted to a solid, passing through an oil stage during plant operations could lead to problems with product formation on large scale. In addition, with respect to Forms C and E, these forms contained residual acetone which is not acceptable for plant API production.

Last, Form D has a high melting point. This allows for added stability during manufacturing, transport, and storage. More specific details for each of the five hydrogen bromide salt forms are as follows.

Form A and Form B

Amorphous HBr salt of Compound 1 was slurried in various solvents. 50 mg of the amorphous HBr salts were suspended in ethyl acetate (EA), ethanol (EtOH), methyl-tert-butyl-ether (MtBE or MTBE), isopropyl acetate (IPAc), methyl ethyl ketone (MEK), and methyl isobutyl ketone (MIBK) solvents (about 10 vol) at 10° C. for 20 hours. Samples were taken from the suspensions under nitrogen protection and dried at 50° C. for 10 minutes. All residual solids were still amorphous.

Mixed solvents of different water quantities were examined. 50 mg amorphous HBr salt was placed in the solvent/water systems and the suspensions were re-slurried at 10° C. for 2 days. The material was filtered and XRPD was run as wet. The material was then dried in an oven at 50° C. for 10 minutes the dry solid was analyzed via XRPD. Table 1a below shows the results of these studies. Isopropanol is IPA.

TABLE 1a

| Solvent | Form before drying | Form after drying |
|---|---|---|
| MtBE/water = 97/3 | Form A | Form A |
| MtBE/water = 94/6 | Form A | Form A |
| MtBE/water = 90/10 | Form A | Form A |
| EA/water = 97/3 | Form A | Form A |
| EA/water = 94/6 | Form A | Form A |
| EA/water = 90/10 | Form A | Form A |
| EtOH/water = 97/3 | Clear solution | Clear solution |
| EtOH/water = 94/6 | Clear solution | Clear solution |
| EtOH/water = 90/10 | Clear solution | Clear solution |
| IPA/water = 97/3 | Form B | Form B |
| IPA/water = 94/6 | Form B | Form B |
| IPA/water = 90/10 | Form B | Form B |
| IPAc/water = 97/3 | Form A | Form A |
| IPAc/water = 94/6 | Form A | Form A |
| IPAc/water = 90/10 | Form A | Form A |

Form A and Form B can also be prepared starting from amorphous Compound 1, i.e., the free-based form instead of an HBr salt form. In this instance, Form A was determined to be a bis-hydrogen bromide salt, and Form B was determined to be a mono-hydrogen bromide salt. Procedures for their formation as follows.

For Form A, identified as a bis-hydrogen bromide salt, 1 g of amorphous free base (i.e., Compound 1) was dissolved/suspended in 10 vol of ethyl acetate at RT. 40% HBr/water solution (0.66×; 2.00e.q.) was then added dropwise at RT. Seeds of Form A were added and the mixture was cooled to 10° C. and slurried overnight. The mixture was then filtered and dried at RT overnight.

In order to confirm the formation of Form A at larger scale, a 5 g scale up experiment was carried out. 5 g of Form B was charged to the reactor at RT. 10 vol of EA/water=97/3 was added at RT followed by 40% HBr/water solution (0.2×; 0.7 e.q.) dropwise at RT. Seeds of Form A were added and cooled to 10° C. The system was protected with $N_2$ and the mixture was stirred overnight. The mixture was filtered and dried at 40° C. with water in oven. Table 2 shows the analytical data of a typical sample of Form A. The bromine (Br) content is 21.1%, therefore indicating a bis-hydrogen bromide salt. The IPA and EA content confirms that Form A is not an IPA or EA solvate.

TABLE 2

| IPA Residual solvent | EA Residual solvent | Residual Br-(%) by IC | Purity |
|---|---|---|---|
| 13 ppm | N.D. | 21.1% | 96.3% |

When Form A (bis salt) is obtained directly from the amorphous free base, Compound 1, directly, purification was not satisfactory. Form A was therefore primarily produced from the mono-hydrogen bromide salt, Form B. DVS scan showed Form A absorbs around 20% water at 90% RH. Form A is chemically stable at RT and 50° C. under vacuum. However, some crystallinity was lost at 50° C. (XRPD pattern changed slightly). Also, during the salt formation procedure, the material transforms to an oil and then converts to solid (Form A).

For Form B, identified as a mono-hydrogen bromide salt, 1 g of amorphous free base (i.e., Compound 1) was dissolved/suspended in 10 vol of isopropanol at RT. 35% HBr/AcOH (0.48×, 1.15 eq) was added dropwise into the reactor at RT. Seeds of Form B were added and the mixture was cooled to 10° C. and slurried overnight. The mixture was then filtered and dried at RT overnight.

In order to confirm that the mono-hydrogen bromide salt Form B can be generated from free base Compound 1, a scale up experiment was carried out. 5 g of free base was dissolved/suspended in 10 vol of IPA/3% water at RT. 35% HBr/AcOH (0.48×, 1.15 eq) was added dropwise into the reactor at RT. Seeds of Form B were added and the mixture was cooled to 10° C. The mixture was protected with $N_2$ and slurried overnight. The mixture was filtered and dried at 50° C. for 5 hrs. Table 3 shows the analytical data of a typical sample of Form B. As shown in Table 3, the IPA content is around 4%. After drying the solid at 50° C., the solid converted to amorphous, and IPA content was reduced to 3800 pm. Form B is therefore a potential IPA solvate. The bromine content of Form B (or amorphous from conversion) solid is 12%. This confirms that Form B (or amorphous) solid is a mono salt and is not a stable structure (due to conversion). DVS scan showed Form B absorbs around 10% water at 90% RH.

TABLE 3

| IPA Residual solvent | Residual Br-(%) by IC | Purity | XRPD form |
|---|---|---|---|
| ~4% (as Form B) 3800 ppm (as amorphous) | 12.0% | 97.6% | Form B (wet) Amorphous (dry) |

Representative XRPD peaks for Form A and Form B are provided in Tables 4 and 5 below.

TABLE 4

Form A

| 2-Theta | d(A) | Height | I % |
|---|---|---|---|
| 7.541 | 11.714 | 26 | 25.2 |
| 8.04 | 10.9878 | 27 | 26.2 |
| 10.495 | 8.4226 | 20 | 19.4 |
| 13.061 | 6.773 | 22 | 21.4 |
| 14.242 | 6.2136 | 26 | 25.2 |
| 14.899 | 5.9413 | 55 | 53.4 |
| 16.317 | 5.428 | 32 | 31.1 |
| 17.72 | 5.001 | 11 | 10.7 |
| 17.94 | 4.9403 | 15 | 14.6 |
| 18.648 | 4.7543 | 9 | 8.7 |
| 19.405 | 4.5705 | 13 | 12.6 |
| 19.542 | 4.5387 | 13 | 12.6 |
| 20.28 | 4.3752 | 103 | 100 |
| 20.699 | 4.2876 | 61 | 59.2 |
| 22 | 4.037 | 69 | 67 |
| 22.8 | 3.897 | 7 | 6.8 |
| 23.182 | 3.8337 | 46 | 44.7 |
| 23.341 | 3.808 | 73 | 70.9 |
| 23.745 | 3.744 | 13 | 12.6 |
| 25.084 | 3.5472 | 21 | 20.4 |
| 25.242 | 3.5253 | 26 | 25.2 |
| 26.02 | 3.4216 | 9 | 8.7 |
| 26.459 | 3.3658 | 55 | 53.4 |
| 27.121 | 3.2852 | 26 | 25.2 |
| 27.5 | 3.2407 | 2 | 1.9 |
| 28.981 | 3.0785 | 27 | 26.2 |
| 29.161 | 3.0599 | 27 | 26.2 |
| 29.381 | 3.0374 | 29 | 28.2 |
| 30.52 | 2.9266 | 6 | 5.8 |
| 30.82 | 2.8988 | 8 | 7.8 |
| 31.444 | 2.8427 | 12 | 11.7 |
| 32.322 | 2.7675 | 16 | 15.5 |
| 32.501 | 2.7526 | 17 | 16.5 |
| 32.784 | 2.7295 | 16 | 15.5 |
| 33.823 | 2.648 | 14 | 13.6 |
| 34.203 | 2.6194 | 13 | 12.6 |
| 34.799 | 2.5759 | 17 | 16.5 |
| 35.23 | 2.5454 | 8 | 7.8 |
| 35.457 | 2.5296 | 12 | 11.7 |

TABLE 5

Form B

| 2-Theta | d(A) | Height | I % |
|---|---|---|---|
| 3.94 | 22.4078 | 151 | 74 |
| 5.24 | 16.8507 | 117 | 57.4 |
| 6.897 | 12.8053 | 20 | 9.8 |
| 7.98 | 11.0698 | 204 | 100 |
| 10.622 | 8.3222 | 46 | 22.5 |
| 11.182 | 7.9062 | 15 | 7.4 |
| 12.119 | 7.2968 | 130 | 63.7 |
| 13.462 | 6.5718 | 11 | 5.4 |
| 14.02 | 6.3114 | 52 | 25.5 |
| 14.42 | 6.1374 | 8 | 3.9 |
| 14.861 | 5.9564 | 41 | 20.1 |
| 15.24 | 5.8089 | 5 | 2.5 |
| 15.58 | 5.6831 | 47 | 23 |
| 16.1 | 5.5004 | 79 | 38.7 |
| 16.641 | 5.3229 | 132 | 64.7 |
| 17.62 | 5.0294 | 65 | 31.9 |
| 18.56 | 4.7767 | 9 | 4.4 |
| 19.04 | 4.6573 | 51 | 25 |
| 19.42 | 4.567 | 143 | 70.1 |
| 20.48 | 4.333 | 75 | 36.8 |
| 21.18 | 4.1914 | 111 | 54.4 |
| 21.518 | 4.1262 | 113 | 55.4 |
| 22.681 | 3.9172 | 46 | 22.5 |
| 23.159 | 3.8374 | 80 | 39.2 |
| 23.74 | 3.7448 | 8 | 3.9 |
| 24.101 | 3.6896 | 65 | 31.9 |
| 24.58 | 3.6187 | 68 | 33.3 |
| 24.938 | 3.5676 | 68 | 33.3 |
| 25.34 | 3.5119 | 21 | 10.3 |
| 25.641 | 3.4713 | 58 | 28.4 |
| 26.181 | 3.401 | 87 | 42.6 |
| 26.9 | 3.3117 | 46 | 22.5 |
| 27.8 | 3.2065 | 88 | 43.1 |
| 28.36 | 3.1444 | 28 | 13.7 |
| 28.782 | 3.0993 | 75 | 36.8 |
| 29.678 | 3.0077 | 50 | 24.5 |
| 30.602 | 2.919 | 27 | 13.2 |
| 30.824 | 2.8984 | 32 | 15.7 |
| 31.138 | 2.8699 | 36 | 17.6 |
| 32.295 | 2.7697 | 29 | 14.2 |
| 33.118 | 2.7027 | 52 | 25.5 |
| 34.122 | 2.6254 | 15 | 7.4 |

Form C and Form E

As explained above, during the crystallization experiments for Form A, the material initially converted to oil. After slurring the oil for several hours, the oil gradually converted to solid. Although it was not determined to be an issue here, passing through an oil stage for in plant operations could lead to problems in product formation on large scale. To overcome this potential problem, other solvent system were investigated which ultimately lead to the finding of a new form, Form C.

In these experiments, 100 mg of the mono-hydrogen bromide salt Form B was charged to a reactor at RT. 10 vol of acetone/water=97/3; DCM/water=97/3; EtOH/water=97/3; or ACN/water=97/3 was added to the reactor at RT. 40% HBr/water solution was added dropwise at RT (to make the total HBr amount as 2.0 e.q. mole). Seeds of the bis-hydrogen bromide salt Form A was added and the mixture was cooled to 5° C. and slurried overnight. The results are shown below in Table 6.

TABLE 6

| Solvent system | Form |
|---|---|
| Acetone/water | Form C |
| DCM/water | Form A |
| EtOH/water | Clear solution |
| Acetonitrile/water | Clear solution |

As shown above, no solid was generated from EtOH/water or acetonitrile/water system. DCM/water system produced bis salt (Form A), however, this experiment also passed through oil. Acetone/water system crystallized without oil out issue while produced a new form (called Form C). Once identified, formation of Form C was optimized as follows.

For Form C, 1 g of amorphous mono-hydrogen bromide salt Form B is charged to a reactor a RT. 10 vol acetone/water=97/3 is added followed by 40% HBr/water solution (to make the total HBr amount as 2.0 e.q. mole) dropwise at RT. Seeds of Form C are added, the mixture is cooled to 5° C., and slurried for 2-3 hours. The mixture is dried at 50° C. overnight.

For Form E, 1 g of amorphous mono-hydrogen bromide salt Form B is charged to a reactor. 10 vol acetone is added to the reactor at RT followed by 40% HBr/water solution (to make the total HBr amount as 2.0 e.q. mole) dropwise at RT.

Seeds of Form E are added, the mixture is cooled to 5° C., slurried overnight, and then dried at 50° C. overnight.

DVS scan of Form C showed the solid absorbs 9% water at 90% RH. After drying the wet cake of Forms C and E at 50° C., some brown/black particles were found on the surface of the dry cake. Although the brown/black particles can be avoided by optimization of drying procedure (lower drying temperature and protection of $N_2$), this drying procedure did not completely remove residual acetone (residual acetone in the solid >2.4%). See e.g., Table 7 below. Because of the brown/black particles and the residual acetone issue, Forms C or E (acetone/water system) were not selected as the final form for API production.

TABLE 7

| Observation of the dry cake | Br— content | Residual solvent |
|---|---|---|
| White solid | 20.8% | Acetone: 2.4% |
| White solid | 22.4% | Acetone: 2.7% |

Analytical data of a typical Form C sample is shown in Table 8. The bromine content of the solid is generally 17.8%-22.4%. Form C has a wide endotherm between 50-100° C. on DSC scan, and TGA scan shows 2.3% weight loss in this temperature range. DVS scan also showed the solid absorbs 9% water at 90% RH.

TABLE 8

| Residual solvent | Form | Br— content | Purity |
|---|---|---|---|
| Acetone: 1000 ppm IPA: N.D. KF: 2.8% | Form C | 17.8% | 99.2% |

Analytical data of a typical Form E sample is shown in Table 9.

TABLE 9

| Residual solvent | Form | Br— content | Recovery(by ML) | Purity |
|---|---|---|---|---|
| Acetone: 5800 ppm IPA: N.D. KF: 2.5% | Form E | n/a | 97% | 98.4% |

Representative XRPD peaks for Form E are provided in Table 10 below.

TABLE 10

Form E

| 2-Theta | d(A) | Height | I % |
|---|---|---|---|
| 4.1 | 21.5348 | 75 | 41 |
| 5.662 | 15.5969 | 17 | 9.3 |
| 5.801 | 15.2235 | 16 | 8.7 |
| 8.3 | 10.6434 | 157 | 85.8 |
| 11.781 | 7.5054 | 15 | 8.2 |
| 12.659 | 6.9866 | 183 | 100 |
| 14.008 | 6.3168 | 13 | 7.1 |
| 14.241 | 6.214 | 12 | 6.6 |
| 14.403 | 6.1446 | 13 | 7.1 |
| 14.677 | 6.0305 | 11 | 6 |
| 15.7 | 5.6398 | 16 | 8.7 |
| 16.34 | 5.4203 | 5 | 2.7 |
| 16.644 | 5.3219 | 26 | 14.2 |
| 16.98 | 5.2174 | 84 | 45.9 |
| 17.523 | 5.0569 | 12 | 6.6 |
| 18.388 | 4.8209 | 10 | 5.5 |
| 19.015 | 4.6635 | 9 | 4.9 |
| 19.16 | 4.6284 | 6 | 3.3 |
| 19.44 | 4.5624 | 5 | 2.7 |
| 20.02 | 4.4315 | 7 | 3.8 |
| 20.579 | 4.3123 | 17 | 9.3 |
| 21.323 | 4.1636 | 40 | 21.9 |
| 21.68 | 4.0957 | 30 | 16.4 |
| 21.9 | 4.0551 | 16 | 8.7 |
| 22.487 | 3.9506 | 10 | 5.5 |
| 22.914 | 3.8779 | 10 | 5.5 |
| 23.685 | 3.7535 | 11 | 6 |
| 24.18 | 3.6777 | 8 | 4.4 |
| 24.419 | 3.6422 | 22 | 12 |
| 24.779 | 3.5901 | 31 | 16.9 |
| 24.779 | 3.5901 | 31 | 16.9 |
| 25.72 | 3.4609 | 20 | 10.9 |
| 26.499 | 3.3608 | 10 | 5.5 |
| 27.041 | 3.2947 | 14 | 7.7 |
| 27.204 | 3.2753 | 17 | 9.3 |
| 28.14 | 3.1685 | 6 | 3.3 |
| 28.604 | 3.1181 | 13 | 7.1 |

Form D

To prepare Form D, 1 g of amorphous mono-hydrogen bromide salt Form B is charged to a reactor. 5 vol of MeOH at RT is added until the solid is fully dissolved. 40% HBr/Water solution (1.2 e.q.) at RT followed by 8-9 vol of MtBE, and seeded. The mixture is held for 30 min to 1 hr, cooled to 5° C. in 30 min/5 to 6 hrs (two separated experiments; fast/slow cooling rate), and slurried overnight. 14-15 vol of MtBE in 2 to 3 hrs is added, the mixture is slurried for 2 to 3 hours, filtered, and then dried at 45° C.

Scale up of Form D was performed as follows. 2 g amorphous mono salt Form B is charged to a reactor at RT. 5 vol MeOH was added and the solid was made sure to fully dissolve. 40% HBr/water solution (1.2 e.q.) was added dropwise at RT followed by 13 vol MtBE with seeding (first add 4 vol and seed, followed by 2 vol and seed, followed by 2 vol and seed, and so on). The mixture was slurried for half an hour, cooled to 5° C. in 2 hrs, slurried overnight, 10 vol MtBE was added in 2 to 3 hrs and the mixture was slurried over the weekend. The mixture was then filtered and dried at 60° C. and RT for 5 hrs. Results are shown in Table 11.

TABLE 11

| Batch | Form | purity |
|---|---|---|
| 1 | Form D | 99.5% |
| 2 | Form D | 99.5% |

Form D can also isolated from the amorphous bis-hydrogen bromide salt form of Compound 1 in a slurry experiment comprising acetone/water (1:1 v/v). For example, a saturated solution the amorphous bis-hydrogen bromide salt form om acetone/water (1:1 v/v) was slurried for one week at ambient and the solid was harvested to obtain Form D. The water activity ($a_w$) of an equal volume mixture of acetone and water is 0.91. See SSCI internal report, Water Activity Calculations using UNIFAC Calculator, SR-20150515.01, dated Jul. 23, 2015. When solvent-free polymorphs are considered, the relative thermodynamic stability of two polymorphs is determined by the Gibbs free energy difference at a given temperature and pressure. However, when hydrate forms are considered, the water activity in the solvent contributes to the relative physical stability and thus, the resulting form. See Qu H, Louhi-Kultanen M, Kallas J. Solubility and stability of anhydrate/hydrate in solvent mixtures. Int J Pharm. 2006; 321:101-107 and Zhu H, Grant D J W. Influence of water activity in organic solvent+water mixtures on the nature of the crystallizing drug phase. 2. Ampicillin. Int J Pharm. 1996; 139:33-43. This outcome is consistent with Form D as a hydrate and indicates that the hydrate is stable at $a_w$=0.91.

Representative XRPD peaks for Form D are provided in Table 12 below.

TABLE 12

| Form D | | | |
|---|---|---|---|
| 2-Theta | d(A) | Height | I % |
| 7.579 | 11.655 | 45 | 36 |
| 9.02 | 9.7963 | 64 | 51.2 |
| 13.403 | 6.6006 | 15 | 12 |
| 14.24 | 6.2147 | 85 | 68 |
| 14.562 | 6.0778 | 31 | 24.8 |
| 15.241 | 5.8087 | 125 | 100 |
| 15.9 | 5.5692 | 103 | 82.4 |
| 16.8 | 5.2729 | 22 | 17.6 |
| 17.162 | 5.1624 | 44 | 35.2 |
| 17.342 | 5.1092 | 26 | 20.8 |
| 18.54 | 4.7817 | 55 | 44 |
| 18.818 | 4.7117 | 53 | 42.4 |
| 19.279 | 4.6001 | 13 | 10.4 |
| 19.643 | 4.5157 | 20 | 16 |

TABLE 12-continued

| Form D | | | |
|---|---|---|---|
| 2-Theta | d(A) | Height | I % |
| 20.14 | 4.4054 | 48 | 38.4 |
| 20.7 | 4.2873 | 49 | 39.2 |
| 21.02 | 4.2229 | 42 | 33.6 |
| 21.699 | 4.0921 | 49 | 39.2 |
| 22.46 | 3.9553 | 88 | 70.4 |
| 23.362 | 3.8045 | 24 | 19.2 |
| 23.698 | 3.7513 | 17 | 13.6 |
| 24.362 | 3.6505 | 41 | 32.8 |
| 24.578 | 3.619 | 29 | 23.2 |
| 24.799 | 3.5873 | 11 | 8.8 |
| 25.237 | 3.526 | 35 | 28 |
| 25.406 | 3.503 | 18 | 14.4 |
| 25.659 | 3.4689 | 42 | 33.6 |
| 25.822 | 3.4474 | 59 | 47.2 |
| 26.102 | 3.411 | 25 | 20 |
| 26.506 | 3.36 | 27 | 21.6 |
| 26.82 | 3.3213 | 67 | 53.6 |
| 27.122 | 3.285 | 19 | 15.2 |
| 27.562 | 3.2336 | 10 | 8 |
| 28.004 | 3.1835 | 19 | 15.2 |
| 28.604 | 3.1182 | 20 | 16 |
| 29.679 | 3.0076 | 35 | 28 |
| 33.701 | 2.6573 | 48 | 38.4 |

Two-Step Formation

The two-step formation to arrive at Form D is shown below in Scheme 5. Intermediate 2 was prepared according to general procedure B in U.S. Pat. No. 9,266,886, the contents of which are incorporated herein by reference.

Scheme 5

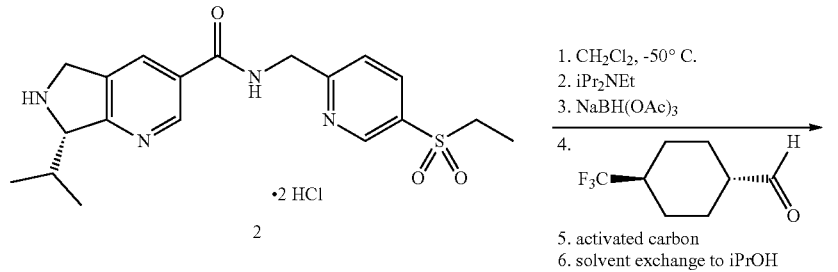

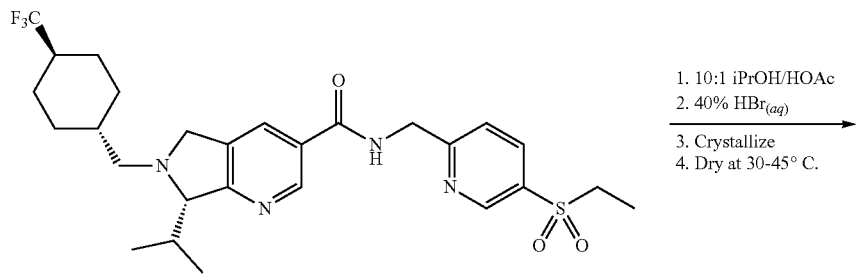

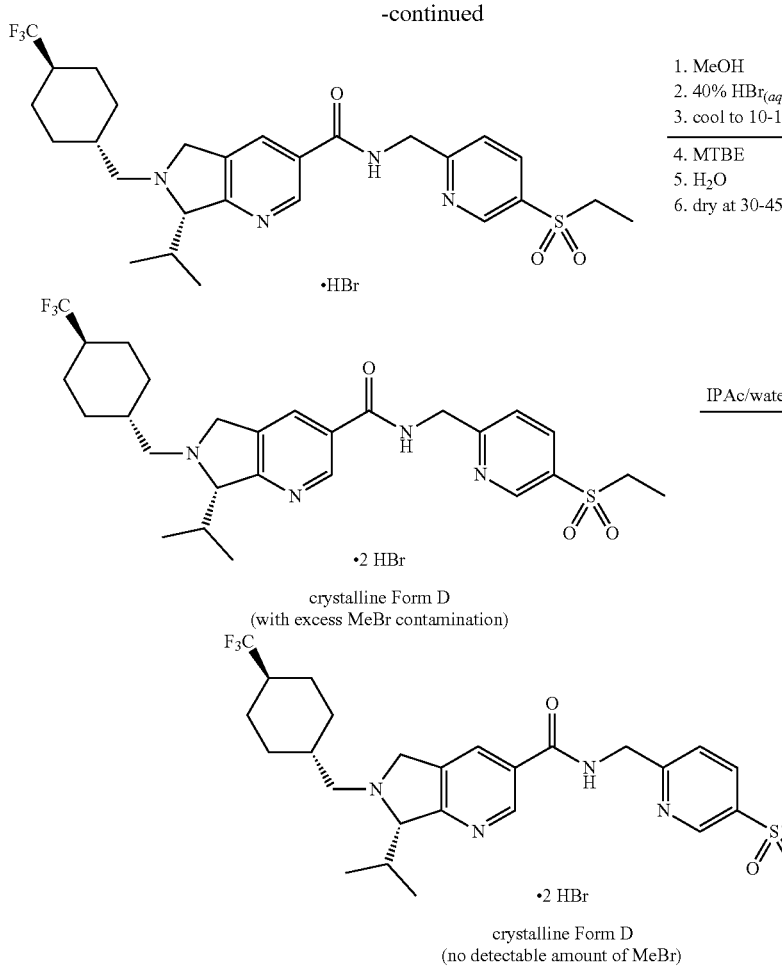

Intermediate 2 is suspended in dichloromethane and the amine liberated by treatment with diisopropylethylamine. The solution is cooled to −50° C. and subsequently treated with NaBH(OAc)$_3$ and the aldehyde. After the reductive amination reaction is complete, the bis-hydrogen bromide is isolated by the following sequence of operations. The dichloromethane solution of 3 is acidified with acetic acid, treated with active carbon and filtered. The solvent is switched to isopropanol. Addition of 40% aqueous HBr (1.4 equivalents), cooling to 10-15° C., seeding and continued aging affords the mono-HBr salt. This material was isolated by centrifugation and dried at 30-45° C. in vacuum. The mono-HBr salt is then converted to the bis-HBr salt by dissolving the mono salt in methanol, adding 1.1 equiv of 40% aqueous HBr, then seeding, followed by additions of MTBE and water. The bis-HBr salt is isolated by filtration and drying at 30-45° C. in vacuum. The final product is isolated as the bis-hydrogen bromide salt Form D with contamination from MeBr (approximately 40 ppm or more at laboratory scale and approximately 227 ppm or greater on plant production of 100 grams or greater).

After numerous attempts and various conditions, it was found that slurrying the bis-hydrogen bromide salt Form D from isopropyl acetate containing 1% water at room temperature effectively produced the bis-hydrogen bromide salt Form D free from detectable amounts of methyl bromide. A combination of heptane and water also removed the methyl bromide, but this combination was not pursued further. A summary of the experiments leading up to these conclusions is provided below.

Based on previous research, residual MeBr could be removed effectively by re-crystallizing from MeOH/MTBE/H$_2$O=1.75 V/12 V/0.15 V. However, considering the potential risk which MeOH may react with HBr contained in Compound 1, MTBE was tried as only re-slurry solvent. Two reactions were carried out under different N$_2$ atmosphere: Stirring at approximately 30 to 35° C. for 96 h, residual MeBr was 65 ppm and 40 ppm respectively. See Table 13. After re-slurry with 20 V of MTBE at approximately 30 to 35° C. for 116 h, residual MeBr in both reactions was decreased to less than 50 ppm.

TABLE 13

| Scale | Conditions | Residual MeBr (ppm) | Br content | Yield | Note |
|---|---|---|---|---|---|
| 40 g | Re-slurry with 20 V MTBE at 30~35° C. and stir with 180 rpm. Adjust to 20~25° C. Filter, and dry N$_2$ balloon | 164 (48 h) 65 (96 h) 34 (114 h) 17 (140 h) | 21.1% (Corrected by KF) | 94.1% | Residual MeOH: 0.07% MTBE: 0.23% |

TABLE 13-continued

| Scale | Conditions | Residual MeBr (ppm) | Br content | Yield | Note |
|---|---|---|---|---|---|
| | always | | | | |
| 40 g | Re-slurry with 20 V MTBE at 30~35° C. and stir with 180 rpm. Adjust to 20-25° C. Filter, and dry. N₂ flow after 48 h | 180 (48 h) 40 (96 h) 20 (116 h) N.D (140 h) | 21.4% (Corrected by KF) | 93.8% | Residual MeOH: 0.12% MTBE: 0.11% |

The developed purification process was then executed in pilot plant study but failed as the residual MeBr was 227 ppm (limitation: Residual MeBr ≤40 ppm). Because of this, other solvents (DCM, IPAc, and n-heptane) were tried. After investigation, it was found that DCM was not a good choice because the crystal form changed, whereas the crystal form remained consistent with Form D after stirring at approximately 20 to 30° C. for 3 days IPAc or n-heptane So studies about how to remove residual MeBr were carried out in IPAc and n-heptane. See Table 14. The effect of emoving MeBr was no different after stirring for 23 h (n-heptane: 148 ppm; IPAc: 153 ppm). However, since the solubility of the bis-hydrogen bromide salt Form D was slightly higher than that in n-heptane, IPAc was chosen as re-slurry solvent. NMR data for bis-hydrogen bromide crystalline Form D of Compound 1 is as follows: $^1$H NMR (500 MHz, CD$_3$OD): δ 9.12 (s, 1H), 9.11 (s, 1H), 8.57 (d, J=8.5 Hz, 1H), 8.37 (s, 1H), 7.97 (d, J=8.5 Hz, 1H), 5.22 (d, J=16 Hz, 1H), 4.89 (d, J=4.0 Hz, 1H), 4.85 (s, 2H), 4.77 (d, J=17.5 Hz, 1H), 3.42 (m, 2H), 3.37 (q, J=7.5 Hz, 2H), 2.54 (m, 1H), 2.17 (m, 1H), 2.04 (m, 5H), 1.45 (m, 2H), 1.33 (d, J=7.0 Hz, 3H), 1.28 (t, J=7.5 Hz, 3H), 1.23 (m, 3H), 1.11 (d, J=6.5 Hz, 3H).

TABLE 14

| | | | Residual MeBr | |
|---|---|---|---|---|
| Scale | Conditions | Time | Wet cake | Dried cake |
| 7 g | Re-slurry 7 g with 10 V IPAc at 20~25° C. under nitrogen balloon | 3 h 6 h 23 h | 117 140 121 | 201 216 153 |
| 7 g | Re-slurry 7 g with 10 V n-heptane at 20~25° C. under nitrogen balloon | 3 h 6 h 23 h | 120 115 110 | 201 227 148 |

To study the influence on the amount of water for the IPAc/water mixture, reactions with different content of water in IPAc were carried out (0.25%, 0.5%, 1.0%, 2.0%). It was found water could improve the efficiency of removing MeBr and that best results were obtained when 1.0% water was used (Table 15, Entry 3; residual MeBr was less than 40 ppm after stirred for 6 h). XRPD was consistent.

TABLE 15

| | | | | Residual MeBr (ppm) | | Br content | |
|---|---|---|---|---|---|---|---|
| Entry | Scale | Conditions | Time | Wet cake | Dried cake | corrected by KF | Note |
| 1 | 10 g | Re-slurry 10 g with 5 V IPAc containing 0.25% water at 20~25° C. with 150 rpm | 3 h 6 h 23 h | 102 44 <40 | 91 66 <40 | 20.95% KF: 5.5% | Residual MeOH: N.D IPAc: 0.025% |
| 2 | 10 g | Re-slurry 10 g of S with 5 V IPAc containing 0.5% water at 20~25° C. with 150 rpm | 3 h 6 h 23 h | 87 <40 ND | 66 51 ND | 21.88% KF: 5.85% | Residual MeOH: N.D IPAc: 0.029% |
| 3 | 10 g | Re-slurry 10 g of S with 5 V IPAc containing 1% water at 20~25° C. with 150 rpm | 3 h 6 h 23 h | <40 <40 ND | 42 <40 ND | 21.88% KF: 5.86% | Residual MeOH: N.D IPAc: 0.045% |
| 4 | 10 g | Re-slurry 10 g of S with 5 V IPAc containing 2% water at 20~25° C. with 150 rpm | 3 h 6 h 23 h | 42 <40 67 | 64 <40 ND | 22.34% KF: 5.99% | Residual MeOH: N.D IPAc: 0.016% |

With the excess methyl bromide problem solved, another drawback to the two-step process was solved. That is, the two-step process also employed methylene chloride as the solvent for the reductive amination procedure. On large manufacturing scale, this would require strict controls due to air and water quality regulations. To overcome these obstacles, a one-step approach to obtain the bis-hydrogen bromide salt Form D directly from the free base of Compound 1 was realized.

One-Step Formation

The one-step approach employing is shown below in Scheme 6. Intermediate 2 was again prepared according to general procedure B in U.S. Pat. No. 9,266,886.

Scheme 6

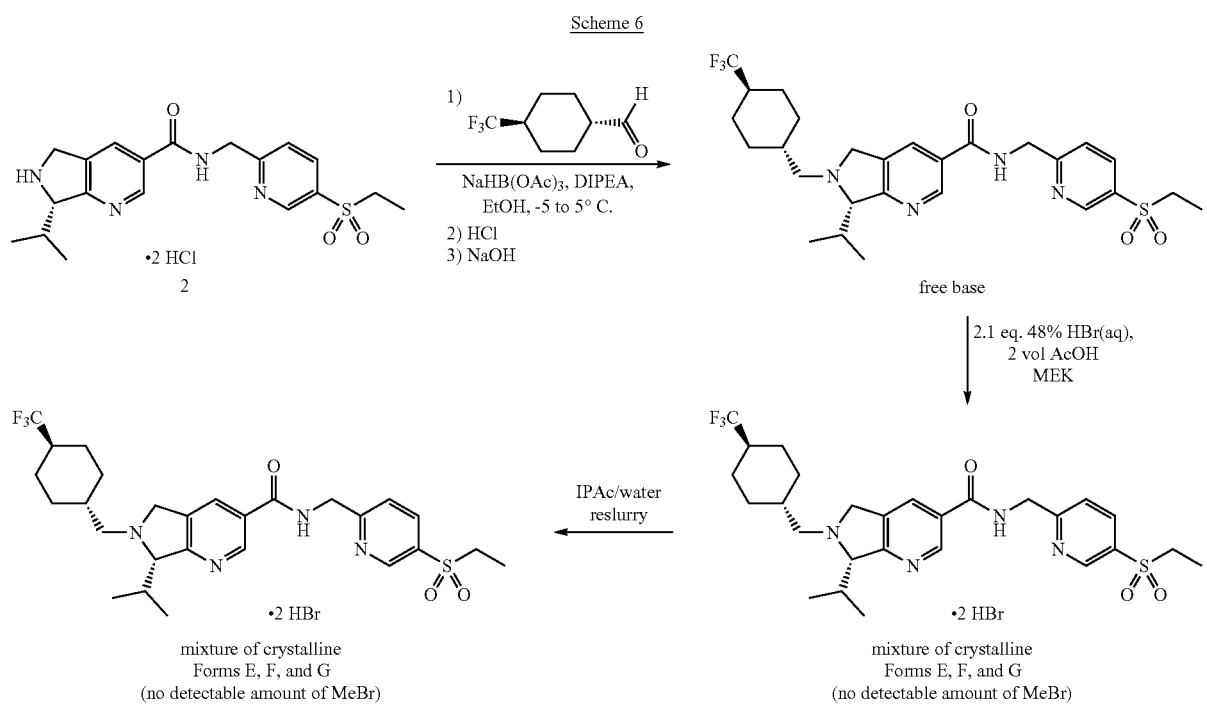

A typical reaction can proceed as follows. To the 30-gal reactor was added 2 (5.12 kg, 9.2 mol, 1.0 equiv). In a carboy was charged ethanol (27.3 L, 7 vol relative to sodium triacetoxyborohydride (STAB)) and DIPEA (3.57 kg, 27.6 mol, 3 equiv relative to 2). The solution of DIPEA/EtOH was added to the reactor with the 2 with no stirring. A cloud of amine hydrochloride formed in the reactor making it difficult to see the slurry, so the batch was allowed to sit without stirring until this cloud dissipated. After 35 min, the cloud dissipated and the mixture was gently stirred. In an hour, the solids had dissolved. The batch was stirred gently overnight at 10° C. and then the 2 was drained from the reactor into a carboy.

The reactor was charged with STAB (3.91 kg, 18.4 mol, 2 equiv) and pre-made solution of DIPEA (2.383 kg, 18.4 mol, 2 equiv) and ethanol (27.2 L, 7 vol relative to STAB) with the jacket at −5° C. The mixture was allowed to cool to 0° C. over 20 min. The solution of 2 in DIPEA/EtOH was added over 27 min followed by the free aldehyde solution in IPAc over 45 min. The maximum temperature during the aldehyde addition was 3.7° C. The mixture was stirred for 1 h and was sampled for reaction completion.

Figure 23:
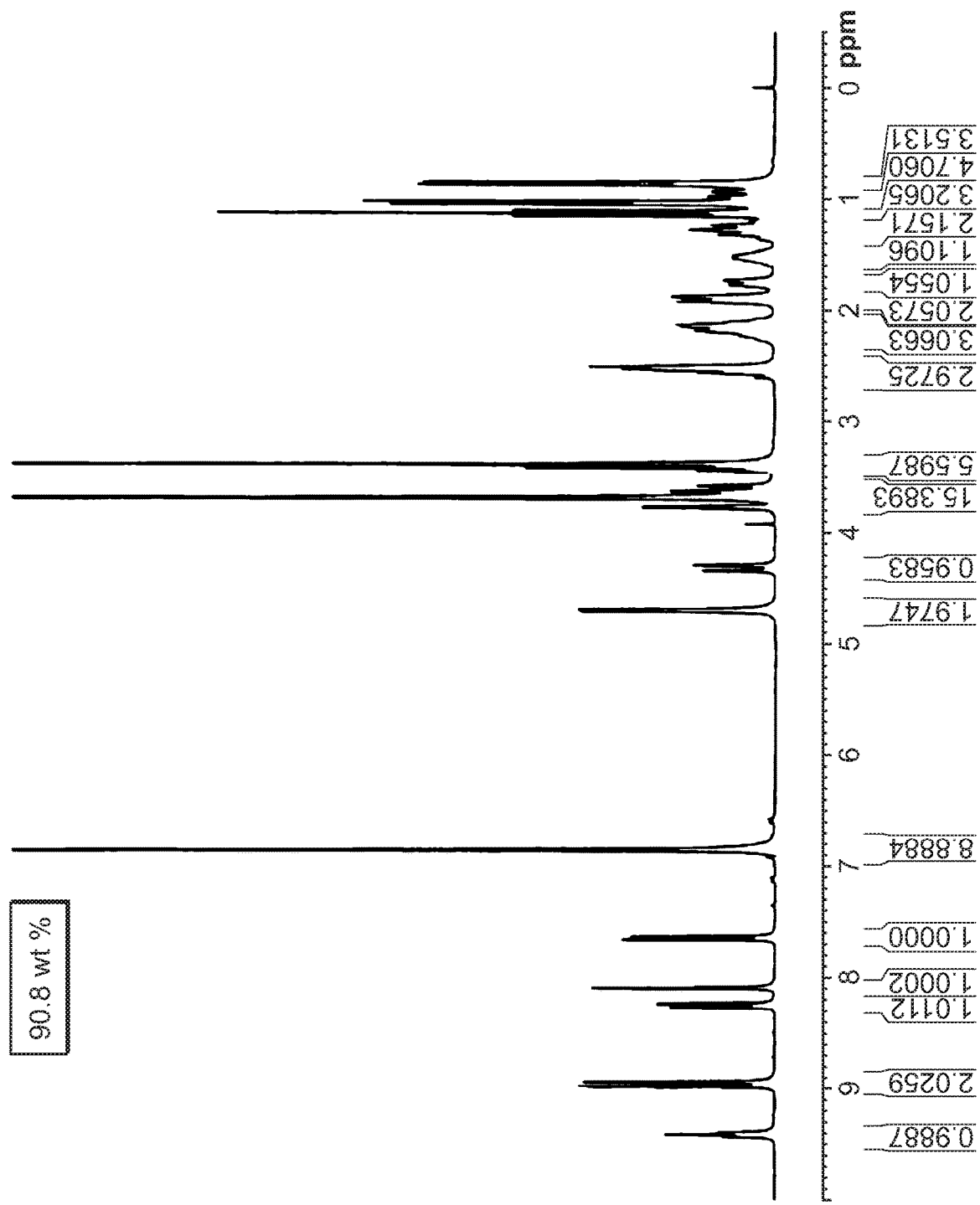
FIG. 23. depicts an 1H-NMR spectrum for Compound 1 made by conditions described herein.

The reaction was quenched by the addition of 1 N HCl (31.2 L, 8 vol relative to STAB) over 33 min. The temperature rose to 11° C. during this addition. The solids dissolved during this quench and the solution was stirred 1 h. The quenched reaction was transferred to a 100-gal. Pfaudler, glass-lined reactor with the jacket set to 10° C. To the 100-gal reactor was charged 1 N NaOH solution (31.2 L, 8 vol relative to STAB). After this addition, the pH rose from approximately 5 to approximately 6 and solids precipitated. The free base slurry was allowed to stir overnight at approximately 10° C. for convenience. The batch was then transferred to a pressure filter equipped with a tight weave cloth. The initial filtration was performed with occasional stirring and the batch de-liquored in about 4 h. The reactor and filter cake were washed with DI water (2×16 L) and 1:1 ethanol/DI water (16 L). The washes took approximately 30 min each. The wet cake was conditioned for 2 h under 8 psig of nitrogen and then was dried at a jacket temperature 35° C. The drying was monitored by KF analysis. The wet cake contained 21% water and the dried cake before off-loading was 5.4% water. The yield was 4.97 kg (98%). The HPLC analysis of the product was 99.7 area %. The NMR weight assay was 90.8 wt % (FIG. 23) and the final KF analysis was 4.7% water. Residue-on-ignition (ROI) analysis of the free base indicated it had 0.2% residual inorganic material.

The material can then be converted to the bis-hydrogen bromide salt by e.g., contacting the free base (0.8026 g) with acetic acid (2 vol, 1.6052 ml) and stirring the mixture at 250 RPM, heated 30° C. A 48% HBr solution is then added (0.3438 ml, 2.1 equiv) drop wise over 9 min. MEK (4.816 ml, 6 vol) is then added over 50 minutes and the reaction is seeded with bis-hydrogen bromide salt Form D. MEK (8.000 ml, 10 vol) is added at 2 ml slowly added every 5 min. The mixture is then chilled to 5° C. over 1 hour, filtered, rinsed w/MEK (2×3.21 ml), and dried in 40° C. vacuum oven/21 hrs to afford a mixture of bis-hydrogen bromide crystalline salt Forms E, D, and F. This procedure was also completed on a 2.5 kg scale. These forms were not characterized further. It should be noted that a mixture of acetic acid/MEK (or acetic acid/acetone) prevents the product from oiling out as well as the production of MeBr. To obtain a single crystalline form, the mixture of forms were slurried in isopropyl acetate with 1% water which gave the bis-hydrogen bromide salt Form D with 98% yield and in >99 area % purity.

Alternative Formation

As an alternative, parts from the one-step and two-step methods can also be combined. For example, the IPAc/water reslurry procedure to remove the residual methyl bromide can be used in the product formation of both the mono- and bis-hydrogen bromide salt forms from the two-step process. The solvent for the reductive amination may also be EtOH instead of methylene chloride and the base may be iPr₂Net. A representative approach is shown below in Scheme 3.

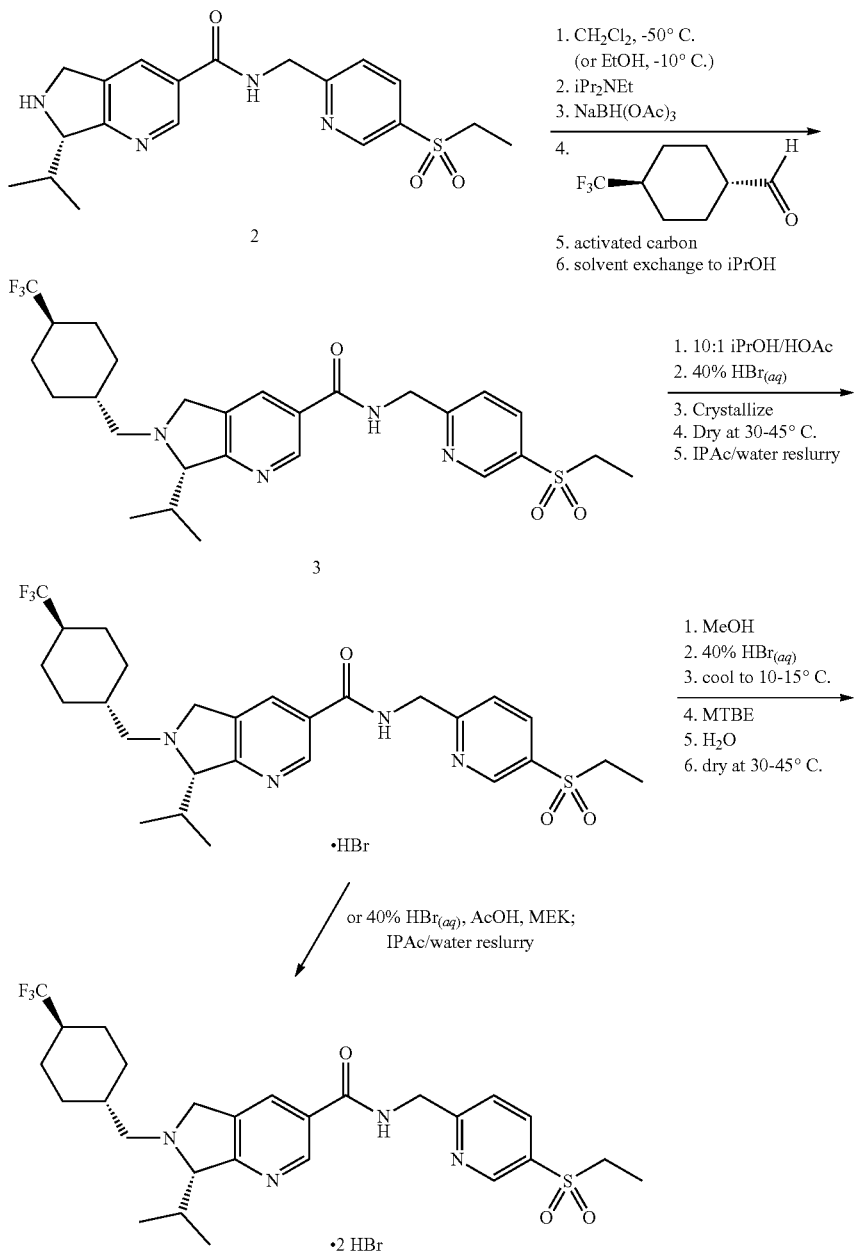

Figure 24:
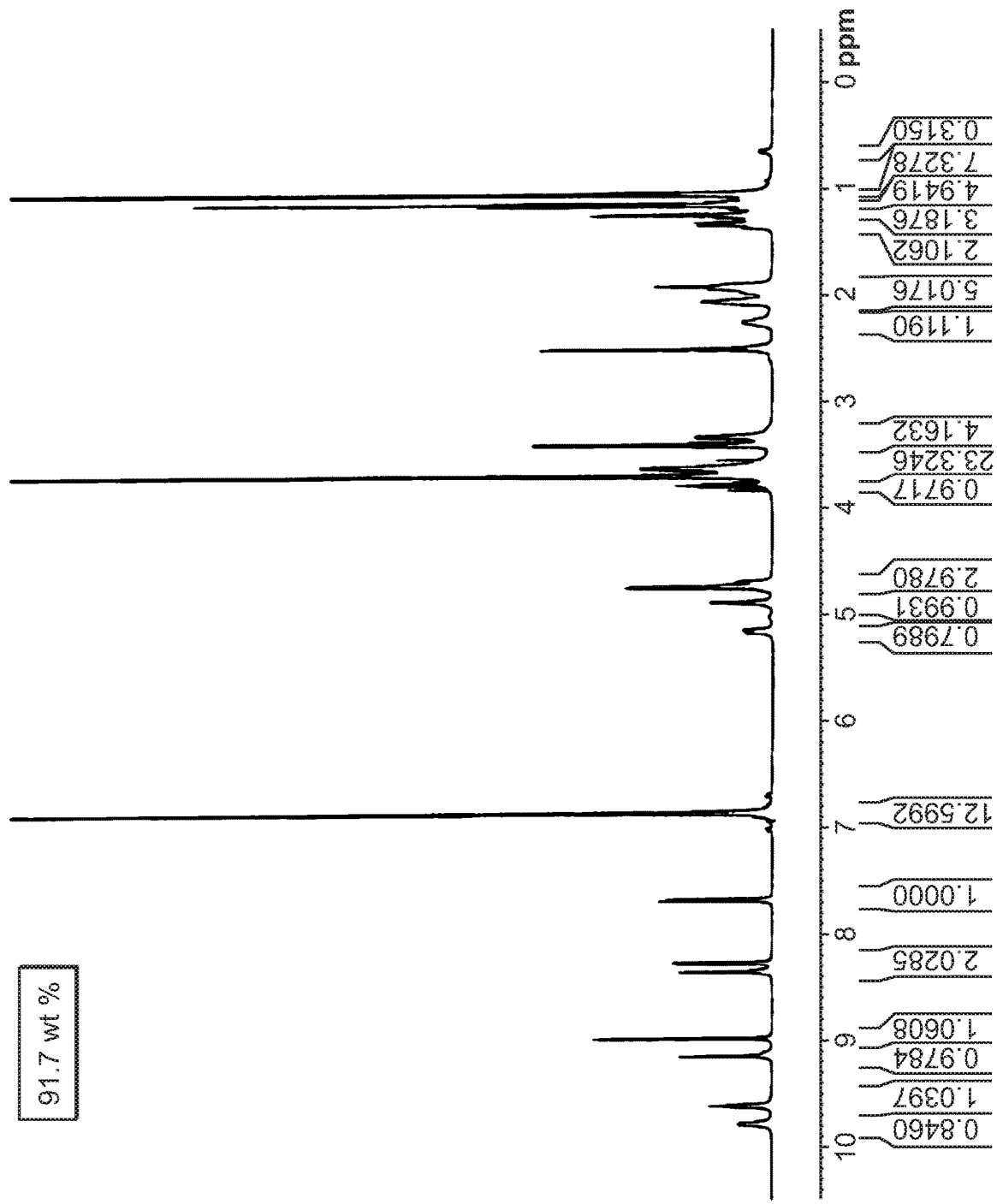
FIG. 24. depicts an 1H-NMR spectrum for a mono-hydrogen bromide salt Form B of Compound 1 made by conditions described herein.
Figure 25:
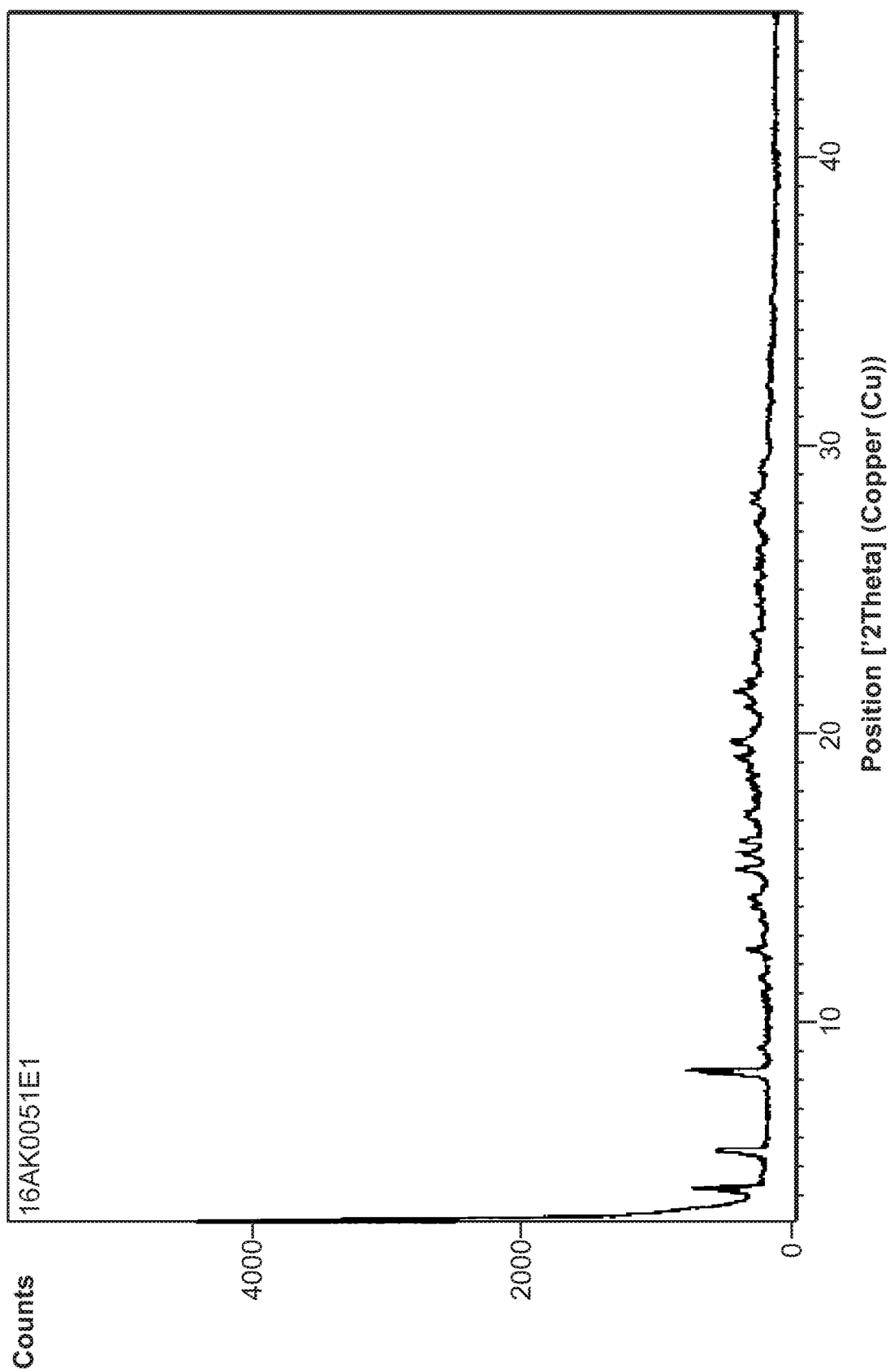
FIG. 25. depicts an XRPD spectrum for a mono-hydrogen bromide salt Form B of Compound 1 made by conditions described herein.

For example a large scale process to form the mono-hydrogen bromide product using the EtOH/DIPEA conditions was as follows. Compound 3 can be made according to the procedure set forth above. From there, a 30-gal, Pfaudler, glass-lined reactor was charged with 3 free base (4.959 kg, 8.97 mol, 1.0 equiv) and isopropanol (49.5 L, 10 vol). Acetic acid (1.49 L, 0.3 vol) was charged to the stirred mixture. Aqueous hydrobromic acid (48%, 1.664 kg, 9.87 mol, 1.1 equiv) was added to mixture over 16 min and the mixture was stirred at room temperature for 32 min. The batch was then warmed to 40° C. over 48 min. No solids were observed at this point. The batch was cooled to 6.7° C. over 5 h. Crystallization was noted at after 1.5 h of cooling (10.6° C.). The batch was stirred overnight at 5° C. for convenience. The thick slurry was transferred to a pressure filter equipped with regular weave cloth. The batch de-liquored in 1 h. The reactor and filter cake was washed with IPA (2×17.5 L). Stirring the wet cake caused it to ball up, so it was conditioned under nitrogen pressure overnight with the jacket at 30° C. Overnight some of the batch melted and passed the cloth. The filter was opened and the residue was scraped out of filter with some difficulty. The residue was tray dried in a vacuum oven at 35° C. The batch was completely dried in 22 h, but the material needed to be crushed with a pestle. The yield was 4.556 kg (80%). KF analysis showed the material had 2.97% water. Titration of the material showed that the HBr content was 11.4%. The HPLC analysis was 99.8 area % and the NMR weight assay was 91.7 wt % (FIG. 24). XRPD analysis was consistent with Form B observed in earlier batches. See FIG. 25. Conversion to the bis-hydrogen bromide salt can then occur following the procedures described above.

While have described a number of embodiments of this, it is apparent that our basic examples may be altered to provide other embodiments that utilize the compounds and methods of this disclosure. Therefore, it will be appreciated that the scope of this disclosure is to be defined by the appended claims rather than by the specific embodiments that have been represented by way of example.

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

What is claimed is:

1. A crystalline Form D bis-hydrogen bromide salt having the formula:

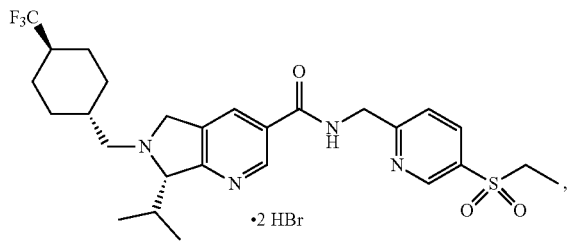 [SMILES: CCS(=O)(=O)c1ccc(CNC(=O)c2cnc3c(c2)CN(C[C@H]2CC[C@H](C(F)(F)F)CC2)[C@H]3C(C)C)nc1 ; "·2 HBr"]

·2 HBr wherein the crystalline Form D bis-hydrogen bromide salt is characterized by at least three x-ray powder diffraction peaks at 2Θ angles selected from 14.24°, 15.24°, 15.90°, 18.54°, 18.82°, and 22.46°; and wherein the crystalline Form D bis-hydrogen bromide salt has a purity of >95%.

2. The crystalline Form D bis-hydrogen bromide salt of claim 1, wherein the crystalline form is characterized by at least four x-ray powder diffraction peaks at 2Θ angles selected from 14.24°, 15.24°, 15.90°, 18.54°, 18.82°, and 22.46°.

3. The crystalline Form D bis-hydrogen bromide salt of claim 1, wherein the crystalline form is characterized by at least five x-ray powder diffraction peaks at 2Θ angles selected from 14.24°, 15.24°, 15.90°, 18.54°, 18.82°, and 22.46°.

4. The crystalline Form D bis-hydrogen bromide salt of any one of claim 1, wherein the crystalline form is characterized by x-ray powder diffraction peaks at 2Θ angles at 14.24°, 15.24°, 15.90°, 18.54°, 18.82°, and 22.46°.

5. The crystalline Form D bis-hydrogen bromide salt of claim 1, wherein the crystalline form is a solvate.

6. The crystalline Form D bis-hydrogen bromide salt of claim 1, wherein the crystalline form is a hydrate.

\* \* \* \* \*